(12) United States Patent
Kataoka et al.

(10) Patent No.: US 8,058,432 B2
(45) Date of Patent: Nov. 15, 2011

(54) METHOD FOR PREPARING PHENYLALANINE DERIVATIVES HAVING QUINAZOLINE-DIONE SKELETON AND INTERMEDIATES FOR USE IN THE PREPARATION OF DERIVATIVES

(75) Inventors: Noriyasu Kataoka, Kawasaki (JP); Kotaro Okado, Kawasaki (JP); Tatsuhiro Yamada, Kawasaki (JP); Koichi Fujita, Kawasaki (JP); Tamotsu Suzuki, Kawasaki (JP); Tatsuya Okuzumi, Kawasaki (JP); Masayuki Sugiki, Kawasaki (JP); Akinori Tatara, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/470,846

(22) Filed: May 22, 2009

(65) Prior Publication Data
US 2009/0318688 A1    Dec. 24, 2009

Related U.S. Application Data

(63) Continuation of application No. PCT/JP2007/072615, filed on Nov. 22, 2007.

(30) Foreign Application Priority Data

Nov. 22, 2006 (JP) .................................. 2006-315837

(51) Int. Cl.
C07D 239/96    (2006.01)
(52) U.S. Cl. ...................................................... 544/285
(58) Field of Classification Search ................... 544/285
See application file for complete search history.

(56) References Cited

U.S. PATENT DOCUMENTS

| | | | |
|---|---|---|---|
| 4,054,591 A | 10/1977 | Klaubert et al. | |
| 4,665,070 A | 5/1987 | Krantz et al. | |
| 6,380,189 B1 | 4/2002 | Abood et al. | |
| 7,153,963 B2 | 12/2006 | Makino et al. | |
| 7,345,049 B2 | 3/2008 | Sagi et al. | |
| 2003/0220268 A1 | 11/2003 | Makino et al. | |
| 2005/0222141 A1 | 10/2005 | Sagi et al. | |
| 2006/0009476 A1 | 1/2006 | Kataoka et al. | |
| 2006/0211689 A1 | 9/2006 | Aranyi et al. | |
| 2006/0223836 A1 | 10/2006 | Makino et al. | |
| 2007/0018172 A1 | 1/2007 | Takahashi et al. | |
| 2008/0108634 A1 | 5/2008 | Sagi et al. | |
| 2008/0108637 A1 | 5/2008 | Fujita et al. | |

FOREIGN PATENT DOCUMENTS

| CN | 1777591 | 5/2006 |
|---|---|---|
| EP | 1 595 870 A1 | 11/2005 |
| JP | 52-046040 | 4/1977 |
| JP | 62-030770 | 2/1987 |
| JP | 11-505849 | 5/1999 |
| WO | WO 96/37485 | 11/1996 |
| WO | WO 01/68586 | 9/2001 |
| WO | WO 02/16329 | 2/2002 |
| WO | WO 2004/074264 | 9/2004 |
| WO | WO 2005/009969 | 2/2005 |
| WO | WO 2005/046696 | 5/2005 |
| WO | WO 2005/046697 | 5/2005 |
| WO | WO 2005/051925 | 6/2005 |
| WO | WO 2005/061466 | 7/2005 |
| WO | WO 2006/137450 | 12/2006 |
| WO | WO 2007/038571 | 4/2007 |
| WO | WO 2007/141473 | 12/2007 |

OTHER PUBLICATIONS

U.S. Appl. No. 12/697,816, filed Feb. 1, 2010, Takahashi, et al.
H.A. Staab, et al., "1,1'-Carbonyldimidazole", Organic Syntheses Collective Volumne, vol. 5, 1973, pp. 201-204.
U.S. Appl. No. 12/766,178, filed Apr. 23, 2010, Katoaka, et al.
Yukuo Eguchi, et al., Studies on Hypotensive Agents. Synthesis of 1-Substituted 3-(2-Chlorophenyl)-6-ethoxycarbonyl-5,7-dimethyl-2,4(1H,3H)-quinazolinediones[1]), Chem. Pharm. Bull. 39 (7), XP-002105928, Jul. 1, 1991, pp. 1753-1759.
U.S. Appl. No. 12/885,936, filed Sep. 20, 2010, Fujita, et al.
Chinese Office Action issued Jun. 15, 2011.

*Primary Examiner* — James O Wilson
*Assistant Examiner* — Brian McDowell
(74) *Attorney, Agent, or Firm* — Oblon, Spivak, McClelland, Maier & Neustadt, L.L.P.

(57) ABSTRACT

The present invention releates to a method for preparing a phenylalanine compound having a quinazoline-dione ring represented by the following formula (1) or a pharmaceutically acceptable salt thereof:

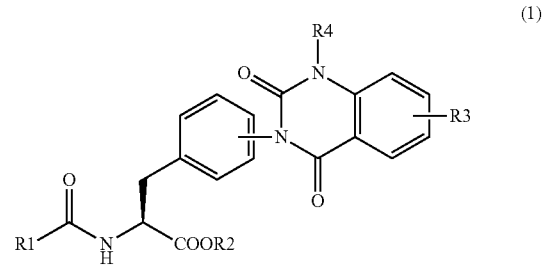

(1)

where R1-R4 are defined herein. The method involves reacting a specified acyl phenylalanine compound with a carbonyl group-introducing reagent and a specified anthranilic acid compound to form a carboxy-asymmetric urea compound which is converted to a quinazoline-dione compound in the presence of a carboxyl group-activating agent.

21 Claims, No Drawings

METHOD FOR PREPARING PHENYLALANINE DERIVATIVES HAVING QUINAZOLINE-DIONE SKELETON AND INTERMEDIATES FOR USE IN THE PREPARATION OF DERIVATIVES

TECHNICAL FIELD

The present invention relates to a method for the preparation of a phenylalanine derivative having a quinazoline-dione skeleton, which is a compound highly useful as a drug having an α-4-integrin-inhibitory activity and as an intermediate of the derivative.

BACKGROUND ART

Recently, there have been advanced studies of inflammatory diseases, in which the α-4-integrin-dependent adhesion process takes part in the pathology thereof, such as rheumatoid arthritis, inflammatory enteritis, systemic erythematosus, multiple sclerosis, Sjögren's syndrome, asthma, psoriasis, allergy, diabetes, cardiovascular diseases, arterial sclerosis, restenosis, tumorigenic hyperplasis, tumor metastasis, and implant-rejection and accordingly, it has been expected that a compound having an α-4-integrin-inhibitory action should be developed and used as a therapeutic agent or a prophylactic agent.

The applicant of this invention has developed an invention relating to a novel phenylalanine derivative which has an α-4-integrin-inhibitory activity and which would be considered to be highly useful as an agent for treating or preventing an inflammatory disease, in which the α-4-integrin-dependent adhesion process takes part in the pathology thereof and the applicant has already filed a patent application (see Patent Document 1 specified below). In this patent application, there has been reported, as a method for the preparation of such a phenylalanine derivative having a quinazoline-dione skeleton, one which comprises the steps of applying a phenylalanine derivative onto a solid phase of a resin to thus construct a quinazoline-dione skeleton through the use of an amide intermediate (see Patent Document 1 specified below).

Moreover, the applicant of this invention has likewise found out an industrially favorable production method of such a derivative and has already filed a patent application (see Patent Document 2 specified below). In this patent application, there has been reported a method comprising the steps of reacting an anthranilic acid derivative whose carboxyl group is protected through an ester bond with a phenylalanine derivative and finally deriving a phenylalanine derivative having a quinazoline-dione skeleton.

Moreover, the applicant of this invention have found out a phenylalanine derivative having a novel quinazoline-dione skeleton, which shows an α-4-integrin-inhibitory action and has already filed a patent application (Patent Document 3 specified below). In this patent application, there has been reported, as a production method, a linear liquid-phase synthetic method for constituting its skeleton in succession.

However, there has still been desired for the development of a method for the preparation of a phenylalanine derivative having a quinazoline-dione skeleton, which is industrially favorable as well as a further synthetic route which has not yet been known. More specifically, there has been desired for the development of a method for preparing the same while accomplishing a variety of merits, for instance, the synthetic route being convergent; the method requiring a small number of steps for the preparation of a final compound starting from a raw material; the method requiring a short period time for the formation of the final product; and the method permitting the production of the final compound in a higher yield; and the resulting final compound being highly pure.

Patent Document 1: WO 02/16329;
Patent Document 2: WO 2004/74264;
Patent Document 3: WO 2005/61466

DISCLOSURE OF THE INVENTION

Accordingly, it is an object of the present invention to provide a method for the preparation of a phenylalanine derivative having a quinazoline-dione skeleton, which can industrially favorably produce the intended compound in a higher yield.

It is another object of the present invention to provide a method for the preparation of a phenylalanine derivative having a quinazoline-dione skeleton, which has not yet been known and which can advantageously be industrialized.

It is a still further object of the present invention to provide an intermediate for use in the preparation of a phenylalanine derivative having a quinazoline-dione skeleton.

The present invention thus provides a method (a first production method) for preparing a phenylalanine derivative having a quinazoline-dione ring represented by the following formula (1) or a pharmaceutically acceptable salt thereof, which comprises the following steps (a), (b) and (c):

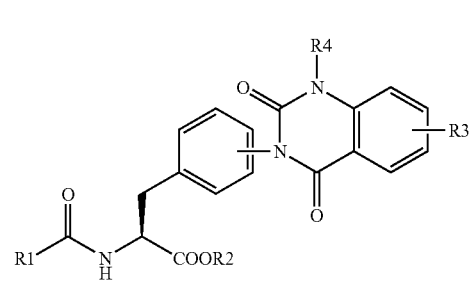

(1)

wherein R1 represents either a phenyl group which may have a substituent or a pyridyl group which may have a substituent; R2 represents an alkyl group which may have a substituent; R3 represents an alkyl group substituted with a di-alkylamino group, an alkyl group substituted with a mono-alkylamino group or an alkyl group substituted with an amino group; and R4 represents a hydrogen atom, an alkyl group or a benzyl group which may have a substituent;

(a) reacting an acyl phenylalanine derivative represented by the following formula (2) or a chemically acceptable salt thereof:

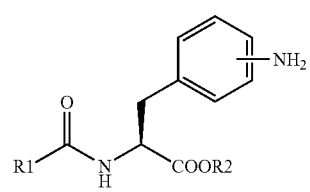

(2)

wherein R1 and R2 are the same as those defined above, with a carbonyl group-introducing reagent and an anthranilic acid derivative represented by the following formula (3) or a chemically acceptable salt thereof:

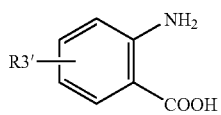
(3)

wherein R3' represents an alkyl group substituted with a dialkylamino group, an alkyl group substituted with a mono-alkylamino group which may have a protective group or an alkyl group substituted with an amino group which may have a protective group, to thus form a carboxy-asymmetric urea derivative represented by the following formula (4) or a chemically acceptable salt thereof:

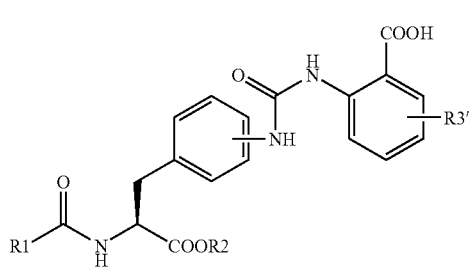
(4)

wherein R1, R2 and R3' are the same as those defined above;

(b) converting the carboxy-asymmetric urea derivative of Formula (4) into a quinazoline-dione derivative represented by the following formula (5) or a pharmaceutically acceptable salt thereof, in the presence of a carboxyl group-activating agent:

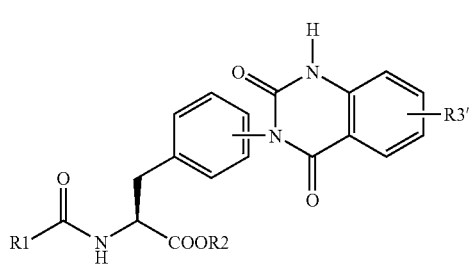
(5)

wherein R1 to R3' are the same as those defined above; and (c) if desired, substituting an N-alkyl group for the hydrogen atom attached to the nitrogen atom present in the quinazoline-dione ring of the quinazoline-dione derivative of Formula (5) using an N-alkylation agent and then deprotecting the resulting product, when the substituent R3' is protected.

Moreover, the present invention further provides a method (a second production method) for the preparation of a phenylalanine derivative having a quinazoline-dione ring represented by the following formula (1-2) or a pharmaceutically acceptable salt thereof, which comprises the following steps (a), (b), (c) and (d):

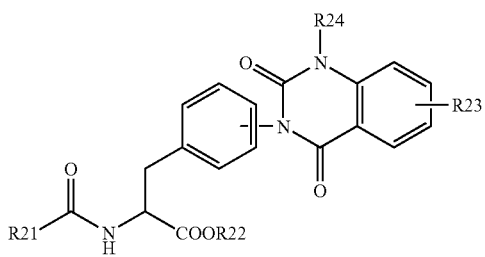
(1-2)

wherein R21 represents either a phenyl group which may have a substituent or a pyridyl group which may have a substituent; R22 represents an alkyl group which may have a substituent; R23 represents a dialkylamino group, a mono-alkylamino group, an amino group, a hydrogen atom, a halogen atom, an alkyl group, a perfluoroalkyl group, an alkoxy group, a nitro group, an alkyl group substituted with a dialkylamino group, an alkyl group substituted with a mono-alkylamino group, an alkyl group substituted with an amino group, an alkyl group substituted with an alkenyl group, an alkyl group substituted with an alkynyl group, a carboxyl group, an alkoxy-carbonyl group, an alkylthio group, or an arylthio group; R24 represents a hydrogen atom, an alkyl group, or a benzyl group which may have a substituent;

(a) converting an acyl phenylalanine derivative represented by the following formula (2-2) or a chemically acceptable salt thereof:

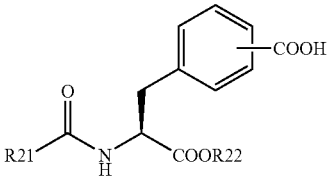
(2-2)

wherein R21 and R22 are the same as those defined above, into an isocyanate derivative ad then converting carboxyl group thereof into an isocyanyl group;

(b) reacting the resulting compound represented by the following formula (3-2) or a chemically acceptable salt thereof:

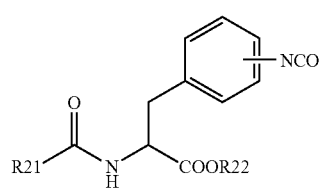
(3-2)

wherein R21 and R22 are the same as those defined above, with an anthranilic acid derivative represented by the following formula (4-2) or a chemically acceptable salt thereof:

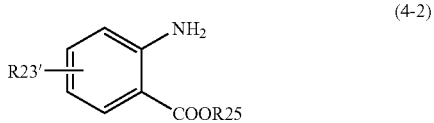

wherein R23' represents a dialkylamino group, a mono-alkylamino group, an amino group which may have a protective group, a hydrogen atom, a halogen atom, an alkyl group, a perfluoroalkyl group, an alkoxy group, a nitro group, an alkyl group substituted with a dialkylamino group, an alkyl group substituted with a mono-alkylamino group which may have a protective group, an alkyl group substituted with an amino group which may have a protective group, an alkyl group substituted with an alkenyl group, an alkyl group substituted with an alkynyl group, a carboxyl group, an alkoxy-carbonyl group, an alkylthio group, or an arylthio group; and R25 represents a hydrogen atom, or an alkyl group which may have a substituent;

(c) converting the resulting asymmetric urea derivative represented by the following formula (5-2) or a chemically acceptable salt thereof:

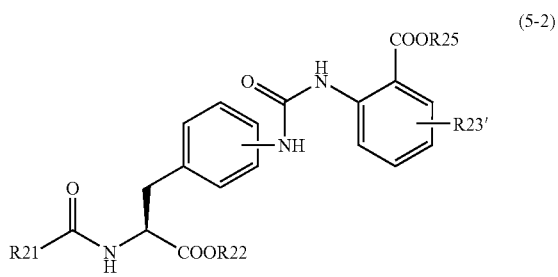

wherein R21, R22, R23' and R25 are the same as those defined above,
into a quinazoline-dione derivative represented by the following formula (6-2) or a chemically acceptable salt thereof:

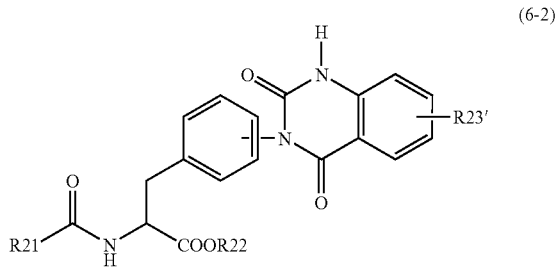

wherein R21 to R23' are the same as those defined above,
in the presence of a carboxyl group-activating agent when R25 is a hydrogen atom, or in the presence of a base when R25 is an alkyl group;

(d) if desired, substituting an N-alkyl group for the hydrogen atom attached to the nitrogen atom present in the quinazoline-dione ring of the quinazoline-dione derivative of Formula (6-2) using an N-alkylation agent and then deprotecting the resulting product, when the substituent R23' is protected.

According to the present invention, there is further provided a method (a third production method) for the preparation of a phenylalanine derivative having a quinazoline-dione ring, represented by the following formula (1-3) or a pharmaceutically acceptable salt thereof, which comprises the following steps (a), (b) and (c):

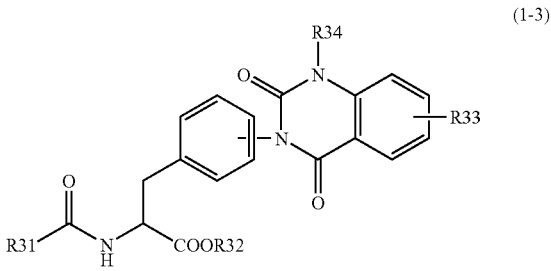

wherein R31 represents either a phenyl group which may have a substituent or a pyridyl group which may have a substituent; R32 represents an alkyl group which may have a substituent; R33 represents a dialkylamino group, a mono-alkylamino group, an amino group, a hydrogen atom, a halogen atom, an alkyl group, a perfluoroalkyl group, an alkoxy group, a nitro group, an alkyl group substituted with a dialkylamino group, an alkyl group substituted with a mono-alkylamino group, an alkyl group substituted with an amino group, an alkyl group substituted with an alkenyl group, an alkyl group substituted with an alkynyl group, a carboxyl group, an alkoxy-carbonyl group, an alkylthio group, or an arylthio group; R34 represents a hydrogen atom, an alkyl group, or a benzyl group which may have a substituent;

(a) reacting a derivative of an isatoic anhydride represented by the following formula (2-3) or a chemically acceptable salt thereof:

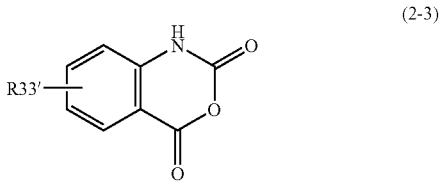

wherein R33' represents a dialkylamino group, a mono-alkylamino group, an amino group which may have a protective group, a hydrogen atom, a halogen atom, an alkyl group, a perfluoroalkyl group, an alkoxy group, a nitro group, an alkyl group substituted with a dialkylamino group, an alkyl group substituted with a mono-alkylamino group which may have a protective group, an alkyl group substituted with an amino group which may have a protective group, an alkyl group substituted with an alkenyl group, an alkyl group substituted with an alkynyl group, a carboxyl group, an alkoxy-carbonyl group, an alkylthio group, or an arylthio group, with an acyl-phenylalanine derivative represented by the following formula (3-3) or a chemically acceptable salt thereof:

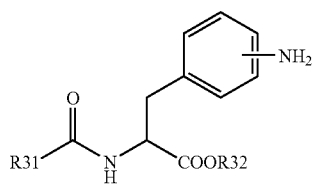

(3-3)

wherein R31 and R32 are the same as those defined above;

(b) reacting the resulting amide derivative represented by the following formula (4-3):

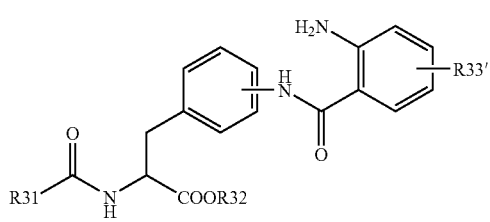

(4-3)

wherein R31, R32 and R33' are the same as those defined above, with a carbonyl group-introducing reagent to thus form a quinazoline-dione derivative represented by the following formula (5-3):

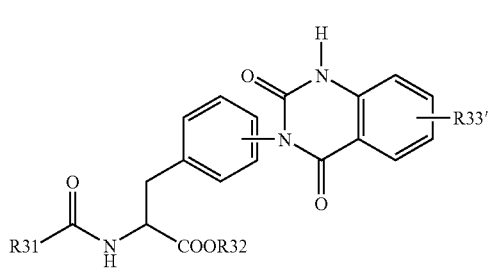

(5-3)

wherein R31 to R33' are the same as those defined above; and (c) if desired, substituting an N-alkyl group for the hydrogen atom attached to the nitrogen atom present in the quinazoline-dione ring of the quinazoline-dione derivative of Formula (5-3) using an N-alkylation agent and then deprotecting the resulting product, when the substituent R33' is protected.

According to the present invention, there is further provided a method (a fourth production method) for preparing phenylalanine derivative having a quinazoline-dione ring represented by the following formula (1-4) or a pharmaceutically acceptable salt thereof, which comprises the following steps (a), (b) and (c):

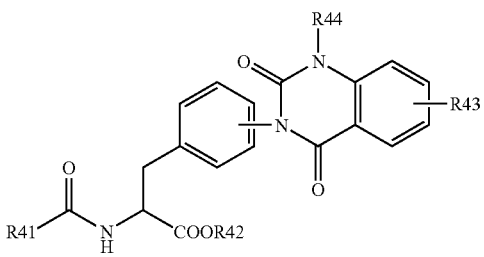

(1-4)

wherein R41 represents either a phenyl group which may have a substituent or a pyridyl group which may have a substituent; R42 represents an alkyl group which may have a substituent; R43 represents a dialkylamino group, a mono-alkylamino group, an amino group, a hydrogen atom, a halogen atom, an alkyl group, a perfluoroalkyl group, an alkoxy group, a nitro group, an alkyl group substituted with a dialkylamino group, an alkyl group substituted with a mono-alkylamino group, an alkyl group substituted with an amino group, an alkyl group substituted with an alkenyl group, an alkyl group substituted with an alkynyl group, a carboxyl group, an alkoxy-carbonyl group, an alkylthio group, or an arylthio group; R44 represents a hydrogen atom, an alkyl group, or a benzyl group which may have a substituent;

(a) reacting a benzoxazine derivative represented by the following formula (2-4):

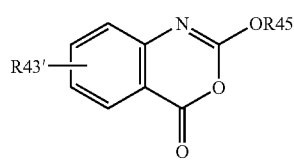

(2-4)

wherein R43' represents a dialkylamino group, a mono-alkylamino group, an amino group which may have a protective group, a hydrogen atom, a halogen atom, an alkyl group, a perfluoroalkyl group, an alkoxy group, a nitro group, an alkyl group substituted with a dialkylamino group, an alkyl group substituted with a mono-alkylamino group which may have a protective group, an alkyl group substituted with an amino group which may have a protective group, an alkyl group substituted with an alkenyl group, an alkyl group substituted with an alkynyl group, a carboxyl group, an alkoxy-carbonyl group, an alkylthio group, or an arylthio group; and R45 represents an alkyl group or a phenyl group which may have a substituent, with an acyl-phenylalanine derivative represented by the following formula (3-4) or a chemically acceptable salt thereof:

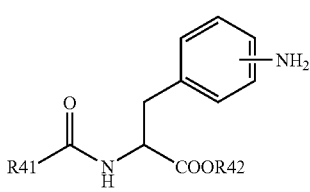

(3-4)

wherein R41 and R42 are the same as those defined above;

(b) converting the resulting amide-carbamate derivative represented by the following formula (4-4) or a chemically acceptable salt thereof:

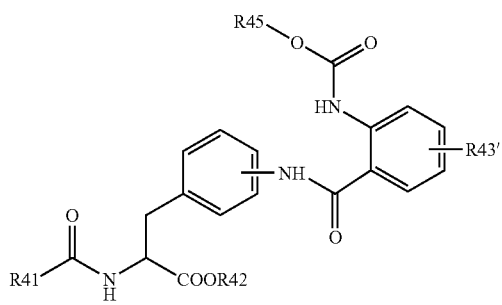

(4-4)

wherein R41, R42, R43' and R45 are the same as those defined above;
into a quinazoline-dione derivative represented by the following formula (5-4) in the presence of a base:

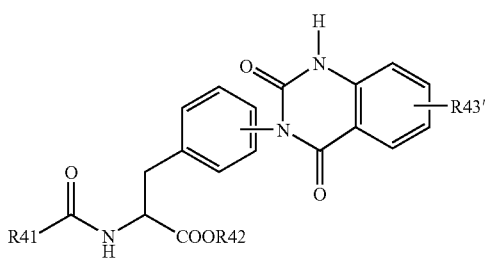

(5-4)

wherein R41 to R43' are the same as those defined above; and
(c) if desired, substituting an N-alkyl group for the hydrogen atom attached to the nitrogen atom present in the quinazoline-dione ring of the quinazoline-dione derivative of Formula (5-4) using an N-alkylation agent and then deprotecting the resulting product, when the substituent R43' is protected.

BEST MODE FOR CARRYING OUT THE INVENTION

In the present invention, the quinazoline-dione ring group appearing in the formula s (1), (1-2), (1-3), and (1-4) may be positioned at o-, m- or p-position on the benzene ring of the phenylalanine, but the ring group is preferably present at p-position among others.

In the present invention, the substituents of the phenyl group which may have a substituent and those of the pyridyl group which may have a substituent, represented by R1, R21, R31 and R41 may be, for instance, halogen atoms, alkyl groups, halogenoalkyl groups (including perfluoroalkyl groups), alkoxy groups, halogenoalkoxy groups (including perfluoro-alkoxy groups), alkylthio groups, nitro group, alkyl-sulfonylamino groups, and tetrazolyl group. In this respect, the alkyl groups as the components of these substituents are preferably those having 1 to 6 carbon atoms and particularly preferably 1 to 3 carbon atoms. Further, the number of the foregoing substituents ranges from 1 to 5, preferably 1 to 3 and they may be the same or different. Preferably used herein as the substituents R1, R21, R31 and R41 are phenyl groups substituted with halogen atoms and/or alkyl groups and specific examples thereof include 2,6-dichlorophenyl group, 2,6-dimethylphenyl group, 2-chloro-6-methyl phenyl group, 2-chlorophenyl group, 2-methylphenyl group, 2,4,6-tri-chlorophenyl group, 2,4,6-trimethyl phenyl group, and 2,6-dichloro-4-methyl phenyl group.

In the present invention, the alkyl groups of the foregoing substituted or unsubstituted alkyl groups represented by R2, R22, R32 and R42 are preferably those having 1 to 6 carbon atoms and particularly preferably those having 1 to 3 carbon atoms.

In R2, R22, R32 and R42 each having a substituent, the substituents may be, for instance, substituted or unsubstituted lower alkyl-carbonyloxy groups, substituted or unsubstituted lower alkoxy-carbonyloxy groups, substituted or unsubstituted amino groups, lower alkoxy groups, halogen atoms, substituted or unsubstituted aryl groups, substituted or unsubstituted heteroaryl groups and substituted or unsubstituted carbamoyl groups.

In this respect, when the substituents are lower alkyl-carbonyloxy groups, lower alkoxy-carbonyloxy groups, and lower alkoxy groups, the alkyl and alkoxy groups thereof are preferably those having 1 to 6 carbon atoms and they include chain-like, cyclic, linear, and branched ones.

Moreover, when the substituents are aryl groups, the aryl group may be a monocyclic to dicyclic aromatic hydrocarbon group having 6 to 10 carbon atoms. Examples thereof include phenyl groups and naphthyl groups. In addition, when the substituents are heteroaryl groups, they may be 5- to 8-membered monocyclic to tricyclic aromatic hetero ring groups including 1 to 4 hetero atoms, as the ring-forming atoms, selected from oxygen atom, sulfur atom and nitrogen atom. Specific examples thereof include pyridyl group, pyridazinyl group, pyrimidyl group, pyrazinyl group, furyl group, thienyl group, pyrrolyl group, isoxazolyl group, oxazolyl group, isothiazolyl group, thiazolyl group, pyrazolyl group, imidazolyl group, tetrazolyl group, indolyl group, benzimidazolyl group, quinolyl group, and isoquinolyl group. In this regard, the substituents for the aryl and heteroaryl groups may be, for instance, halogen atoms, alkoxy groups, alkyl groups, hydroxyl group, halogenoalkyl groups, and halogeno-alkoxy groups. Among them, preferably used herein are pyridyl group, furyl group and thienyl group.

In the meantime, if the substituents of R2, R22, R32 and R42 are lower alkyl-carbonyloxy groups or lower alkoxy-carbonyloxy groups, the substituents thereof may be, for instance, lower alkyl groups, lower alkenyl groups, lower alkoxy groups, hydroxyl group, amino groups, and amino groups each substituted with a lower alkyl group (including mono- and di-substituted ones). Preferably used in the present invention are methyl group and ethyl group among others.

Moreover, if the substituents of R2, R22, R32 and R42 are amino groups, the substituents thereof may be, for instance, lower alkyl groups, lower alkoxycarbonyl groups, and lower alkylsulfonyl groups. Among them, preferred are methyl group and ethyl group. Alternatively, two substituents may be bonded to form a ring and these two groups may be interrupted by oxygen, nitrogen and/or sulfur atoms when they form a ring. For instance, the substituted amino group includes a ring-like amino group such as 1-piperidinyl group or 4-morpholinyl group; a ring-like amide group such as 2-oxo-1-pyrrolidinyl group; and a ring-like urea group such as 2-oxoimidazolin-1-yl group or 2-oxoimidazolidin-1-yl group.

In addition, if the substituents of R2, R22, R32 and R42 are aryl or heteroaryl groups, the substituents thereof may be, for instance, halogen atoms, alkoxy groups, alkyl groups, hydroxyl group, halogenoalkyl groups, and halogenoalkoxy groups.

Further, if the substituents of R2, R22, R32 and R42 are carbamoyl groups, the substituents thereof may be, for instance, lower alkyl groups, and phenyl group, and they include mono- and di-substituted ones.

Moreover, if R2, R22, R32 and R42 have substituents, such substituents preferably used herein may be, for instance, lower alkyl-carbonyloxy groups, chlorine atom, pyridyl group, furyl group, thienyl group, and di-lower alkyl-carbamoyl groups.

In the present invention, R3 is preferably a monoalkyl-aminoalkyl group; R23, R33 and R43 are preferably dialkylamino groups, hydrogen atom, halogen atoms, mono-alkylamino groups, alkyl groups substituted with dialkylamino groups, alkyl groups substituted with mono-alkylamino groups, alkyl groups substituted with alkynyl groups, alkyl groups substituted with amino groups, carboxyl group, alkoxycarbonyl groups, and alkylthio groups and particularly preferred R23, R33 and R43 are dialkylamino groups, mono-alkylamino groups, alkyl groups substituted with dialkylamino groups, alkyl groups substituted with mono-alkylamino groups, alkyl groups substituted with amino groups, alkyl groups substituted with alkynyl groups, carboxyl group, alkoxycarbonyl groups, and alkylthio groups.

Moreover, in the present invention, R3', R23', R33' and R43' are the same as those represented by R3, R23, R33 and R43, respectively or groups capable of being converted into the same as those represented by the latter during the production processes, respectively. The protective groups present in R3', R23', R33' and R43' are preferably those currently used for the protection of amino groups (Protective Groups in Organic Synthesis ($3^{rd}$ edition), T. W Green, P. G. M. Wootz, JOHN WILEY & SONS, INC., 1999), formyl groups, alkylcarbonyl groups, and alkoxycarbonyl groups, in which the alkyl groups and alkoxy groups are preferably those having 1 to 3 carbon atoms. Preferably used herein include those resistant to the basic conditions and capable of being easily deprotected under acidic conditions and more specifically formyl groups and t-butoxycarbonyl group are preferably used herein.

The dialkylamino group herein means an amino group substituted with two alkyl groups each having 1 to 6 carbon atoms (inclusive of cyclic amino groups), preferably an amino group or a cyclic amino group having 2 to 6 carbon atoms, which is substituted with two alkyl groups each having 1 to 3 carbon atoms and specific examples thereof are di-methylamino group, di-ethylamino group, methylethylamino group, pyrrolidinyl group, piperidinyl group, di-propylamino group, methyl-propyl-amino group, and ethyl-propylamino group.

The mono-alkylamino group herein means an amino group substituted with a single alkyl group having 1 to 6 carbon atoms (inclusive of amino groups carrying a cyclic alkyl group), preferably an amino group substituted with one alkyl group having 1 to 4 carbon atoms and specific examples thereof include methylamino group, ethylamino group, propylamino group, isopropyl-amino group, butylamino group, and cyclopropyl-methylamino group.

The alkyl group substituted with a dialkylamino group herein used means an alkyl group having 1 to 6 carbon atoms and substituted with the same dialkylamino group described above, preferably an alkyl group having 1 to 3 carbon atoms and substituted with the same dialkylamino group described above, and specific examples thereof are methyl, ethyl and propyl groups each substituted with a dimethyl-amino group, a diethylamino group, a methylethylamino group, a pyrrolidinyl group, a piperidinyl group, a di-propylamino group, a methyl-propylamino group, or an ethyl-propylamino group. Particularly preferably used herein are dimethylamino-methyl group, diethyl-aminomethyl group, and methylethyl-aminomethyl group.

The alkyl group substituted with a mono-alkylamino group herein used means an alkyl group having 1 to 6 carbon atoms and substituted with the same mono-alkylamino group described above, preferably an alkyl group having 1 to 3 carbon atoms and substituted with the same mono-alkylamino group described above, and specific examples thereof are methyl, ethyl and propyl groups each substituted with a methylamino group, an ethylamino group, a propylamino group, an isopropyl-amino group, a butylamino group, or a cyclopropyl-methylamino group. Particularly preferably used herein are methylamino-methyl group, ethylamino-methyl group, methylamino-ethyl group, and ethylamino-ethyl group.

The alkyl group substituted with an amino group herein used means an alkyl group having 1 to 6 carbon atoms and substituted with an amino group, preferably an alkyl group having 1 to 3 carbon atoms and substituted with an amino group, and specific examples thereof are aminomethyl group, aminoethyl group and aminopropyl group.

The alkyl group substituted with an alkenyl group herein used means an alkyl group having 1 to 6 carbon atoms and substituted with an alkenyl group having 2 to 6 carbon atoms, preferably an alkyl group having 1 to 3 carbon atoms and substituted with an alkenyl group having 2 to 4 carbon atoms, and specific examples thereof are —$CH_2CH=CH_2$ and —$CH_2CH_2CH=CH_2$.

The alkyl group substituted with an alkynyl group herein used means an alkyl group having 1 to 6 carbon atoms and substituted with an alkynyl group having 2 to 6 carbon atoms, preferably an alkyl group having 1 to 3 carbon atoms and substituted with an alkynyl group having 2 to 4 carbon atoms, and specific examples thereof are —$CH_2C\equiv CH$ and —$CH_2CH_2C\equiv CH$.

The alkoxycarbonyl group herein used means an alkoxycarbonyl group having 2 to 7 carbon atoms, preferably an alkoxycarbonyl group having 2 to 4 carbon atoms, and specific examples thereof include methoxycarbonyl group, ethoxycarbonyl group, and propyloxy-carbonyl group.

The alkylthio group herein used means a thio group substituted with an alkyl group having 1 to 6 carbon atoms, preferably a thio group substituted with an alkyl group having 1 to 3 carbon atoms and specific examples thereof include methylthio group, ethylthio group and propylthio group.

The arylthio group herein used includes, for instance, phenylthio and naphthylthio groups.

More specifically, R3 preferably represents methyl-aminomethyl and ethyl-aminomethyl groups; R23, R33 and R43 preferably represent dimethylamino, diethylamino, methylethylamino, pyrrolidinyl, piperidinyl, methylamino, ethylamino, propylamino, cyclopropyl-methylamino, dimethyl-aminomethyl, diethyl-aminomethyl, dimethyl-aminoethyl, diethyl-aminoethyl, methyl-aminomethyl, ethyl-aminomethyl, propyl-aminomethyl, methyl-aminoethyl, ethyl-aminoethyl, propyl-aminoethyl, HC$\equiv$C$CH_2$, carboxyl, methoxycarbonyl, ethoxycarbonyl, methylthio and ethylthio groups, among others.

In addition, in the present invention, R3, R23, R33, R43, R3', R23', R33' and R43' are preferably situated at the p-position with respect to the nitrogen atom corresponding to the amino group of the anthranilic acid.

In the present invention, R4, R24, R34 and R44 each preferably represent a hydrogen atom or an alkyl group. In this respect, the alkyl group is preferably one having 1 to 3 carbon atoms. Further, the substituents for the benzyl group may be, for instance, alkyl groups, alkoxy groups and halogen atoms, but preferred is a benzyl group free of any substituent.

The substituent R25 preferably represents an alkyl group among others. In this connection, the alkyl group preferably represents one having 1 to 3 carbon atoms.

The substituent R45 may be, for instance, an alkyl group and a phenyl group which may have a substituent, but preferably used herein include alkyl groups each having 1 to 3 carbon atoms, among others. In this respect, the substituents present on the phenyl group may be, for instance, alkyl groups, alkoxy groups and halogen atoms, but preferred is a phenyl group free of any substituent.

According to the present invention, there is provided, in the first production method, a compound represented by the following formula (3-1) as an intermediate for use in the preparation of phenylalanine derivative having a quinazoline-dione skeleton:

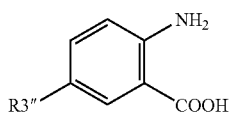
(3-1)

wherein R3" represents a member selected from the group consisting of dialkylamino groups, alkyl groups each substituted with a mono-alkylamino group, N-alkyl-N-formyl-aminoalkyl groups, N-alkyl-N-alkylcarbonyl-aminoalkyl groups, and N-alkyl-N-alkoxycarbonyl-aminoalkyl groups].

Moreover, there are provided, in the first production method, the compounds represented by the following formulas or chemically acceptable salts thereof, as intermediates for use in the preparation of phenylalanine derivatives each having a quinazoline-dione skeleton:

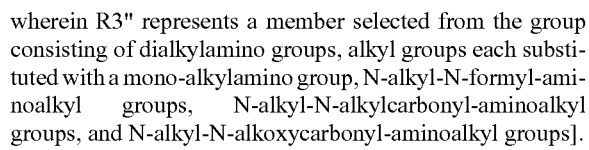

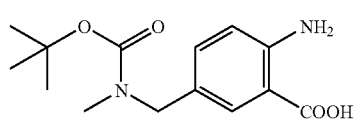

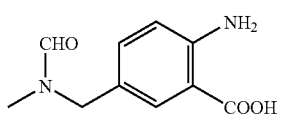

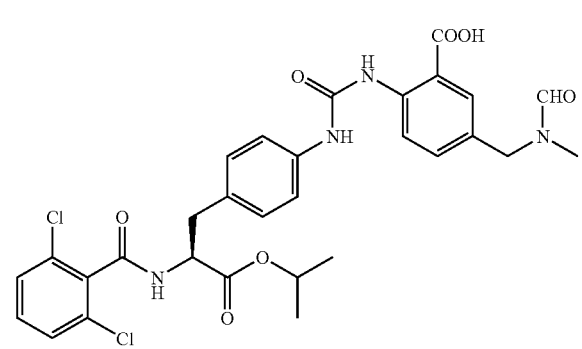

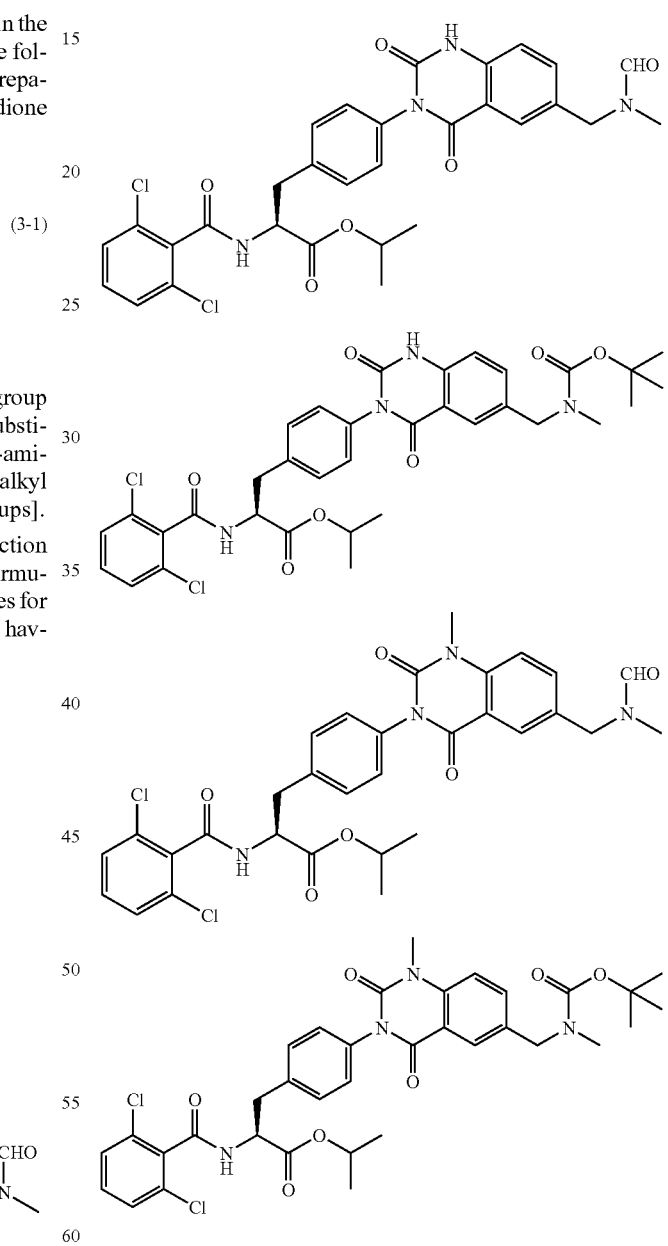

In addition, according to the present invention, there are provided, in the second to forth production methods, the compounds represented by a group of the following formulas or chemically acceptable salts thereof, as intermediates for use in the preparation of phenylalanine derivatives each having a quinazoline-dione skeleton:

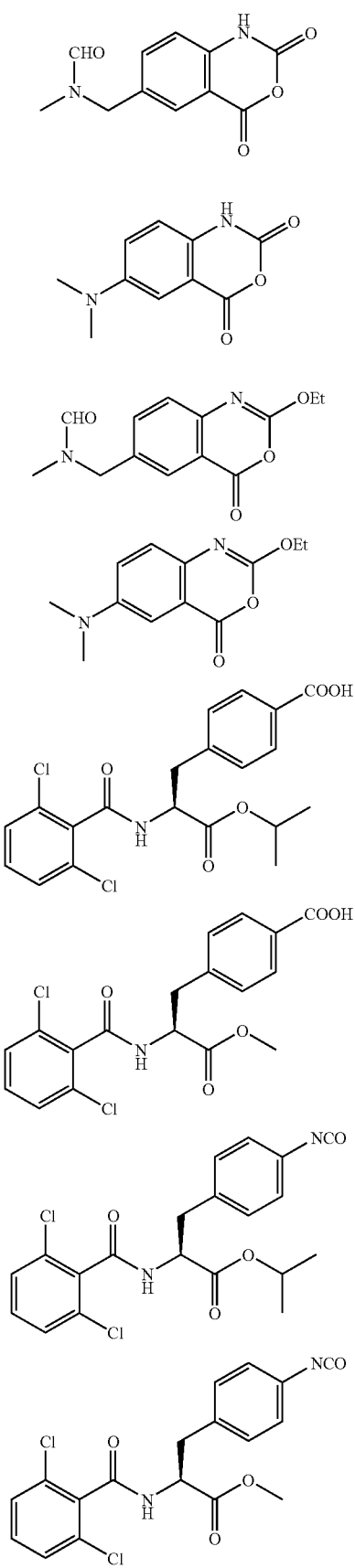

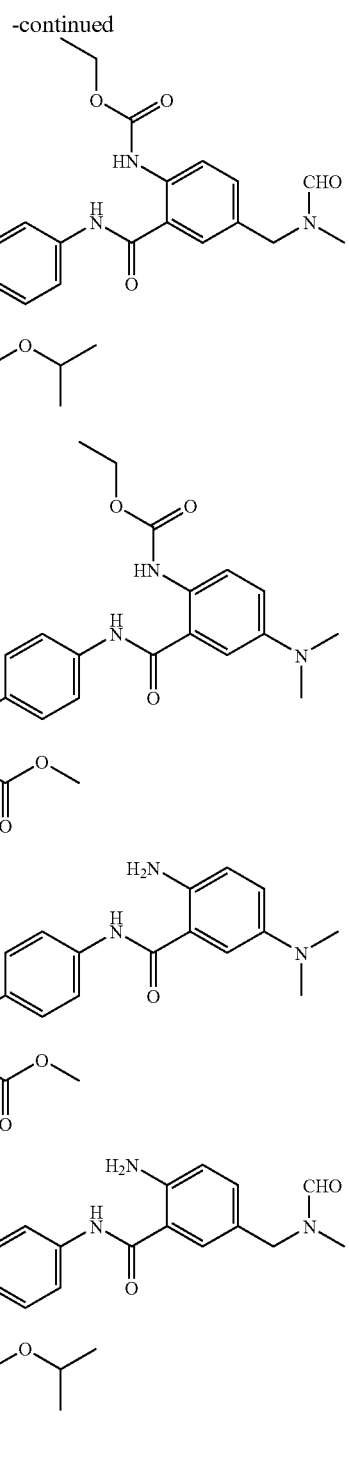

Next, the first production method according to the present invention will hereunder be described in more detail.

The first production method according to the present invention has been completed on the basis of the following finding: If a compound having a carboxyl group (COOH group) free of any ester bond is used as a starting material for the preparation of an anthranilic acid derivative represented by Formula (3) or a chemically acceptable salt thereof, in which R3' represents an alkyl group substituted with a dialkylamino group, an alkyl group substituted with a mono-alkylamino group which may have a protective group, or an alkyl group substituted with an amino group which may have a protective group, the yield of the reaction can significantly be improved as compared with that accomplished when using a compound whose terminal carboxyl group forms an ester bond as a starting material.

According to the first production method, an acyl phenylalanine derivative represented by Formula (2) or a chemically acceptable salt thereof is first reacted with a carbonyl group-introducing reagent and an anthranilic acid derivative represented by Formula (3) or a chemically acceptable salt thereof, in the step (a). In this respect, the acyl phenylalanine derivative represented by Formula (2) or a chemically acceptable salt thereof can be, for instance, prepared according to the method disclosed in Patent Document 2 or 3, while the anthranilic acid derivative represented by Formula (3) or a chemically acceptable salt thereof can likewise be obtained by, for instance, the hydrolyzation of an ester derivative disclosed in Patent Document 2.

In this connection, the term "carbonyl group-introducing reagent" means one from which only the carbonyl group in the atomic group of the quinazoline-dione ring is derived. Examples thereof include 1,1'-carbonyl-diimidazole (a synthetic example thereof is disclosed in Organic Syntheses Collective Volume V, pp. 201-204, Wiley, New York, 1973), and a chloroformate ester. These compounds are both known and put on the market and accordingly they are commercially available.

Moreover, it is also possible to use ones each obtained by substituting another heteroaryl leaving group for the imidazolyl group of 1,1'-carbonyl-diimidazole such as 1,1'-carbonyl-di-(1,2,4-triazole) (in this reagent, an imidazolyl group is substituted with a triazoyl and the reagent may be commercially available). The substituents are not restricted to imidazolyl and triazoyl groups and any heteroaryl leaving group other than those specified above can be used.

Furthermore, also usable in the present invention includes N,N'-disuccinimidyl carbonate (DSC) (this reagent is a carbonyl group-introducing reagent in which N-hydroxy-succinimide group serves as a leaving group and which may be commercially available).

Examples of such chloroformate esters include, but are not limited to, those having 2 to 10 carbon atoms such as phenyl chloroformate, nitrophenyl chloroformate, methoxy-phenyl chloroformate, methyl chloroformate, ethyl chloroformate, isobutyl chloroformate, octyl chloroformate, and benzyl chloroformate.

Moreover, usable herein as the carbonyl group-introducing reagents also include, for instance, phosgene and phosgene analogues (such as tri-phosgene).

The carbonyl group-introducing reagent particularly preferably used herein is 1,1'-carbonyl-diimidazole. In particular, when using 1,1'-carbonyl-diimidazole, by-products are produced during the reaction only in a small amount and the use thereof is excellent in that the reaction would provide an intended asymmetric urea derivative at a high yield.

In the meantime, the carbonyl group-introducing reagent is preferably used in an amount ranging from 0.8 to 1.5 mole equivalents per unit mole of the compound of Formula (2).

The concentration of the reagent in the foregoing reaction is suitably one applicable to an industrial process, for instance, in the range of from 0.1 to 10M and desirably around 1.3M when using DMF as a reaction solvent, while taking into consideration the flow properties of the reaction solution and the recrystallization solution encountered when stirring them.

The reaction of the compound of Formula (2) with a carbonyl group-introducing reagent (such as 1,1'-carbonyl-di-imidazole) to form an imidazo-carbonyl derivative is carried out at a temperature preferably ranging from about −40° C. to the boiling point of the reaction solvent used and the reaction temperature more preferably ranges from about 0° C. to 20° C., from the industrial standpoint. Moreover, when forming an alkoxycarbonyl derivative using a chloroformate ester, the reaction is preferably carried out at a temperature ranging from about −40° C. to the boiling point of the reaction solvent used and the reaction is more preferably carried out at a temperature ranging from about 0° C. to 40° C., from the industrial standpoint. In this case, the amount of the reagent to be used preferably ranges from 1.0 to 1.1 equivalents.

In addition, it is preferred to use the compound of Formula (3) in an amount ranging from 0.8 to 1.2 mole equivalents per unit mole of the compound of Formula (2).

Further, when using a chloroformate ester as the carbonyl group-introducing reagent, the reaction is preferably carried out in the coexistence of an organic base. Examples of such organic bases preferably used herein are triethylamine, diisopropyl-ethylamine and pyridine.

The reaction solvents used in this reaction are, for instance, organic solvents which have an appropriate ability of solubilizing the compound of Formula (2) (for instance, $N^{\alpha}$-(2,6-dichlorobenzoyl)-4-amino-L-phenylalanine methyl ester) and examples thereof usable herein include N,N-dimethyl-formamide (DMF), dimethoxy-ethane (DME), dimethyl sulfoxide (DMSO), dimethyl acetamide (DMA), acetonitrile, tetrahydrofuran (THF) or mixed solvents thereof. The use of N,N-dimethylformamide is particularly preferred. The reaction time preferably ranges from about 1 to 5 hours.

The subsequent condensation reaction of the compound of Formula (2) converted into an imidazo-carbonyl derivative or an alkoxycarbonyl derivative with a substituted 2-aminobenzoic acid of Formula (3) is carried out at a temperature preferably ranging from 0 to the boiling point of the reaction solvent used. In particular, the reaction is preferably carried out at a temperature near 50° C., since the urea-forming reaction can be completed within a reaction time ranging from about 2 to 3 hours to thus give a carboxyl asymmetric urea derivative of Formula (4) at a high yield.

In this respect, however, the reaction temperature and the reaction time are not restricted to these specific ranges specified above, the reaction time is determined in correlation with the reaction temperature and it is thus preferred to manage or control the reaction solution by an analytical means such as HPLC technique, from the industrial standpoint.

In the foregoing reaction, the order of the introduction of the starting material and the reagent is not restricted to any specific one, but it is preferred that the compound of Formula (2) is first reacted with a carbonyl group-introducing reagent to thus convert the former into the imidazo-carbonyl derivative or the alkoxycarbonyl derivative thereof and that the latter is then reacted with a compound of Formula (3), since this method permits the achievement of a higher yield of the intended product and the reduction of the amount of by-products, as compared with the method in which the compound of Formula (3) is first converted into its imidazo-carbonyl derivative or its alkoxycarbonyl derivative. In the production method according to the present invention, however, the compound of Formula (3) may first be converted into its imidazo-carbonyl derivative, or the compound of Formula (2), a carbonyl group-introducing reagent and the compound of Formula (3) may be reacted simultaneously.

In the subsequent step (b), the resulting carboxy asymmetric urea derivative of Formula (4) is treated with a carboxyl group-activating agent in a proper reaction solvent to thus form a quinazoline-dione ring and to thus form a quinazoline-dione derivative of Formula (5).

The term "carboxyl group-activating agent" used herein means an agent for activating the carboxyl group derived from anthranilic acid to such an extent, or a higher extent, that the carboxyl group can react with the intramolecular urea-derived nitrogen atom to thus form a quinazoline-dione ring. More specifically, examples of such "carboxyl group-activating agents" include the reagents listed above, with 1,1'-carbonyl-diimidazole being preferably used herein.

Further, the foregoing step (b) can likewise be carried out after once isolating the carboxy asymmetric urea derivative represented by Formula (4) from the reaction solution through the usual separation technique such as crystallization, but it is preferred from the industrial standpoint to continuously carry out these steps (or the step (b) is carried out without isolating the intermediate of Formula (4)).

After the completion of the foregoing quinazoline-dione ring-forming reaction, an alcohol solvent may be added to the reaction system to thus decompose the excess 1,1'-carbonyl-diimidazole (CDI) or chloroformate ester or the like. As such an alcohol solvent to be added, methanol and isopropyl alcohol are preferably used. Moreover, in case of the product having an ester moiety in the molecule, the addition of an alcohol solvent may induce the occurrence of a trans-esterification reaction and therefore, the alcohol solvent should preferably be selected in consideration of the kind of the ester.

Then, in the step (c), the hydrogen atom bonded to the nitrogen atom present in the quinazoline-dione ring of a quinazoline-dione derivative of Formula (5) is, if desired, replaced with an N-alkyl group using an N-alkylation agent and when R3' is protected, the protective group is removed.

In other words, a quinazoline-dione derivative in which R4 in Formula (1) is an alkyl group or a substituted or unsubstituted benzyl group can be derived by acting an N-alkylation agent on the quinazoline-dione derivative of Formula (5) in the presence of a base.

In this specification, the term "N-alkylation agent" means a reagent which can introduce an alkyl group into a compound on its nitrogen atom and examples thereof include a halo-alkane, alkyl sulfonate, a benzyl halide which may have a substituent.

In this respect, such halo-alkanes and alkyl sulfonates are preferably those having 1 to 10 carbon atoms. Further, they are more preferably those having 1 to 6 carbon atoms and, in particular, those having 1 to 3 carbon atoms are preferred. Examples of halo-alkanes are methyl iodide, and ethyl iodide; and examples of alkyl sulfonates are methyl methane-sulfonate, ethyl methane-sulfonate, methyl ethane-sulfonate, ethyl ethane-sulfonate, methyl p-toluene-sulfonate, and ethyl p-toluene-sulfonate. In addition, examples of benzyl halides are benzyl chloride, and benzyl bromide and the substituents thereof may be, for instance, alkyl groups, alkoxy groups and halogen atoms. More preferably, the N-alkylation agent is a member selected from the group consisting of methyl p-toluene-sulfonate, methyl methane-sulfonate, methyl iodide, methyl bromide and methyl chloride.

For instance, when preparing a compound of Formula (1) in which R4 represents a methyl group, methyl p-toluene-sulfonate is suitably used as the N-alkylation agent from the industrial standpoint. In other words, methyl p-toluene-sulfonate has a high boiling point as compared with volatile methyl iodide and accordingly, it can easily be handled at room temperature. Moreover, methyl p-toluene-sulfonate is preferred from the viewpoint of the flow properties of the resulting reaction solution as compared with methyl methane-sulfonate and accordingly, it is favorable in the industrial processes which is accompanied by the liquid-transporting operations.

It is sufficient that the reaction solvent used in this step can dissolve the compound represented by Formula (5) and that it is an organic solvent which is stable during the reaction. Examples of such solvents include N,N-dimethylformamide, and mixed solvent systems comprising N,N-dimethylformamide and alcohols, with N,N-dimethylformamide being preferably used herein.

The amount of the N-alkylation agent to be used suitably ranges from 1 to 2 mole equivalents and preferably 1.0 to 1.2 mole equivalents on the basis of the compound of Formula (4) or Formula (5), but the amount of the reagent to be added may be increased or decreased in consideration of the progress of the reaction.

Examples of the foregoing bases include inorganic bases and organic bases. In this connection, such inorganic bases may be, for instance, alkali metal salts (such as potassium carbonate, sodium carbonate, cesium carbonate, sodium methoxide and sodium ethoxide) and alkaline earth metal salts (such as calcium carbonate, and magnesium carbonate). In addition, examples of organic bases include triethylamine, ethanolamine, morpholine, piperidine, dicyclo-hexylamine, 1,8-diazabicyclo[5.4.0]-undeca-7-ene (DBU), and N,N-di-isopropyl-N-ethylamine (DIPEA). Preferably, the base is an inorganic base, potassium carbonate being preferably used herein, among others.

The amount of the base to be used preferably ranges from 1 to 2 mole equivalents and more preferably about 1.5 mole equivalents, but the amount thereof is not restricted to such a specific range and it may be increased or decreased in consideration of the progress of the reaction.

Moreover, if R3' is protected, the deprotection thereof can easily be carried out according to the usual method such as a method which makes use of acidic conditions or the catalytic reduction technique.

If the protective group is a formyl group, a t-butoxycarbonyl group, or an acyl group (such as an acetyl or a benzoyl group), such a protective group can be removed under acidic conditions. Formyl group and t-butoxycarbonyl group can immediately be removed under acidic conditions and accordingly, they are preferably used as protective groups. Examples of such acids usable herein include hydrochloric acid, hydrogen chloride, sulfuric acid, methane-sulfonic acid, p-toluene-sulfonic acid, hydrobromic acid, and hydrogen bromide. Any appropriate acid can be selected depending on the salt of the compound finally prepared. For instance, if the salt of the intended final compound is hydrochloride, it is preferred to use hydrochloric acid or hydrogen chloride as such an acid. The reaction solvents usable herein include, for instance, dimethylformamide, isopropyl acetate, methyl acetate, isopropyl alcohol and methanol, but a trans-esterification reaction may be induced at the ester moiety of an original drug and therefore, the corresponding alcohol or an alkyl acetate solvent is preferably used.

Moreover, in case of such groups as benzyloxy group, benzyl group and benzyloxy-carbonyl group, the deprotection thereof can be carried out according to, for instance, the catalytic reduction technique.

The resulting phenylalanine derivative represented by Formula (1) or a pharmaceutically acceptable salt thereof can be isolated by the usual separation technique.

In the first production method, the substituent R3 appearing in Formula (1) is preferably a methyl-aminomethyl group, an ethyl-aminomethyl group, a dimethyl-aminomethyl group or a diethyl-aminomethyl group and R3' appearing in Formulas (3) to (5) is preferably a methyl group substituted with a methylamino group carrying a protective group, a methyl group substituted with an ethylamino group carrying a protective group, a dimethyl-aminomethyl group or a diethyl-aminomethyl group.

In addition, it is also preferred that R1 appearing in Formulas (1) to (5) represents a 2,6-dichlorophenyl group, a 2-chloro-6-methylphenyl group, a 2-chloro-6-fluorophenyl group, a 2,6-difluorophenyl group, or a 2-fluoro-6-methylphenyl group; R4 represents a methyl group, or an ethyl group; and the substituent on the benzene ring of phenylalanine is positioned at p-position.

Furthermore, it is preferred that a compound of Formula (2) in which R1 of Formula (2) is a 2,6-dichlorophenyl group and R2 is an isopropyl group, is reacted with 1,1'-carbonyl-diimidazole as a carbonyl group-introducing agent and a compound of Formula (3) in which R3' is an N-formyl-N-methyl-aminomethyl group to thus form 2-(3-{4-[2(S)-2-(2,6-dichlorobenzoylamino)-2-isopropoxycarbonylethyl]phenyl}ureido)-5-(N-formyl-N-methyl-aminomethyl) benzoic acid of Formula (4) in which R1 is a 2,6-dichlorophenyl group, R2 is an isopropyl group, and R3' is an N-formyl-N-methyl-aminomethyl group; then the resulting compound is reacted with 1,1'-carbonyl-diimidazole as a carboxyl group-activating agent to thus convert the former into $N^\alpha$-(2,6-dichlorobenzoyl)-4-{6-(N-formyl-N-methylaminomethyl)quinazoline-2,4[1H,3H]-dion-3-yl}-L-phenylalanine isopropyl ester of Formula (5) in which R1 is a 2,6-dichlorophenyl group, R2 is an isopropyl group and R3' is an N-formyl-N-methyl-aminomethyl group; subsequently N-alkylation of the resulting product is carried out using methyl p-toluene-sulfonate to thus convert the product into $N^\alpha$-(2,6-dichlorobenzoyl)-4-{1-methyl-6-(N-formyl-N-methylaminomethyl)quinazoline-2,4[1H,3H]-dion-3-yl}-L-phenylalanine isopropyl ester; and finally the N-alkylated product is treated with hydrogen chloride to thus deprotect the formyl group thereof to thus give $N^\alpha$-(2,6-dichlorobenzoyl)-4-{1-methyl-6-(N-methylaminomethyl) quinazoline-2,4[1H,3H]-dion-3-yl}-L-phenylalanine isopropyl ester of Formula (1) or a hydrochloride thereof, in which R1 is a 2,6-dichlorophenyl group, R2 is an isopropyl group, R3' is an N-methyl-aminomethyl group and R4 is a methyl group.

In this respect, the foregoing N-alkylation with methyl p-toluene-sulfonate is preferably carried out under basic conditions.

Then the second production method of the present invention will be described below in detail.

The second method of the present invention for the preparation of a phenylalanine derivative having a quinazoline-dione ring represented by Formula (1-2) or a pharmaceutically acceptable salt thereof has been completed on the basis of such a finding that an asymmetric urea derivative can easily and simply be derived without using any carbonyl group-introducing reagent by converting, into an isocyanate, an acyl phenylalanine derivative in which a carboxyl group is linked to the phenyl group thereof and represented by Formula (2-2) or a chemically acceptable salt thereof as a starting material instead of an acyl phenylalanine derivative having an amino group bonded to the phenyl group thereof, followed by converting the carboxyl group into an isocyanyl group and then reacting the resulting isocyanyl derivative with an anthranilic acid derivative having an alkyl ester group and represented by Formula (4-2) or a chemically acceptable salt thereof.

In the second production method, an acyl phenylalanine derivative represented by Formula (2-2) or a chemically acceptable salt thereof is, in the step (a), first subjected to an isocyanate-conversion reaction for the conversion of the carboxyl group into its isocyanyl group to thus form a compound of Formula (3-2) or a chemically acceptable salt thereof, then the resulting compound of Formula (3-2) or a chemically acceptable salt thereof is, in the step (b), reacted with an anthranilic acid derivative of Formula (4-2) or a chemically acceptable salt thereof to thus give an asymmetric urea derivative of Formula (5-2) or a chemically acceptable salt thereof; further in the step (c), the resulting asymmetric urea derivative of Formula (5-2) or a chemically acceptable salt thereof is treated with a carboxyl group-activating agent when R25 is a hydrogen atom or with a base when R25 is an alkyl group to give a quinazoline-dione derivative of Formula (6-2) or a chemically acceptable salt thereof, then in the step (d), the hydrogen atom linked to the nitrogen atom in the quinazoline-dione ring of the quinazoline-dione derivative of Formula (6-2) is, if desired, replaced with an N-alkyl group using an N-alkylation reagent; and in case where R23' is protected, the substituent is deprotected.

In this connection, the foregoing N-alkylation with an N-alkylation reagent is preferably carried out under basic conditions.

In this respect, the acyl phenylalanine derivative represented by Formula (2-2) or a chemically acceptable salt thereof can easily be synthesized, for instance, by reacting a halogenated phenylalanine (preferably 4-iodo-L-phenylalanine) with, for instance, 2,6-dichlorobenzoyl chloride under an alkaline condition to thus form $N^\alpha$-(2,6-dichloro-benzoyl)-halogenated phenylalanine, subsequently converting it into an alkyl ester according to the usual method, and then converting the halogen in the halogenated phenylalanine into a carboxyl group according to the usual method. Then this compound can be reacted with an isocyanate-conversion agent such as an azide compound (preferably diphenyl-phosphoryl azide (DPPA)) for the conversion of the carboxyl group in the compound of Formula (2-2) into an isocyanyl group to thus give a compound of Formula (3-2) or a chemically acceptable salt thereof. At this stage, it is preferred that the isocyanate-conversion agent is used in an amount of 1 to 2 moles per unit mole of the acyl phenylalanine derivative represented by Formula (2-2) or a chemically acceptable salt thereof and the latter compound is subjected to an isocyanate-conversion reaction in an organic solvent such as 1,2-dimethoxy-ethane in the coexistence of an amine such as triethylamine at a temperature ranging from 70 to 95° C. for about one to 5 hours to thus convert the carboxyl group in the compound of Formula (2-2) into an isocyanyl group. Moreover, in place of this method, it is also possible to adopt such a method in which the carboxyl group present in the compound of Formula (2-2) into an acid chloride and then the acid chloride is reacted with sodium azide to thus carry out a desired isocyanate-conversion reaction.

On the other hand, usable herein as the anthranilic acid derivative represented by Formula (4-2) or a chemically acceptable salt thereof include, for instance, ester derivatives such as those disclosed in Patent Document 2.

In the present invention, a compound of Formula (3-2) or a chemically acceptable salt thereof is then reacted with an anthranilic acid derivative represented by Formula (4-2) or a chemically acceptable salt thereof. At this stage, the compound of Formula (4-2) is desirably used in an amount ranging from 0.8 to 1.2 mole equivalent per unit mole of the compound of Formula (3-2).

This reaction is preferably carried out in an organic solvent having an appropriate ability of dissolving the compound of Formula (3-2), such as N,N-dimethyl-formamide (DMF), dimethoxy-ethane (DME), dimethyl sulfoxide (DMSO), dimethyl-acetamide (DMA), acetonitrile, tetrahydrofuran (THF) or a mixed solvent thereof. Dimethoxy-ethane is particularly preferred as such an organic solvent. This reaction is preferably carried out in the presence of an organic base such as triethylamine, diisopropyl-ethylamine or pyridine, or an azide compound (preferably diphenyl-phosphoryl azide (DPPA)). The reaction is preferably carried out for a reaction time ranging from about 1 to 5 hours at a reaction temperature ranging from 70 to 95° C.

In the present invention, the step (b) may be carried out after once isolating the compound of Formula (3-2) from the reaction solution according to the currently used separation technique such as the crystallization, but it is preferred from the industrial standpoint to continuously carry out these steps (or the step (b) is carried out without isolating the intermediate of Formula (3-2)).

Then, in the step (c), the resulting asymmetric urea derivative of Formula (5-2) or a chemically acceptable salt thereof is treated in the presence of a carboxyl group-activating agent in case where R25 is a hydrogen atom or in the presence of a base in case where R25 is an alkyl group to form a quinazoline-dione ring and to thus derive a quinazoline-dione derivative of Formula (6-2) or a chemically acceptable salt thereof. In this respect, the carboxyl group-activating agent and the base usable in this reaction step may be the same as those listed above in connection with the first production method. Among them, preferably used as such carboxyl group-activating agents include, for instance, 1,1'-carbonyl-diimidazole, chloroformate esters, alkylsulfonic acid chlorides, N,N'-dicyclohexyl-carbodiimide (DCC), and 1-ethyl-3-(3-dimethyl-aminopropyl)carbodiimide. In addition, preferably used herein as such bases include, for instance, potassium carbonate and sodium methoxide. The amounts of the carboxyl group-activating agent and the base as well as the conditions for using them described above in connection with the first production method can likewise be adopted in this second production method.

In the present invention, the step (c) may be carried out after once isolating the compound of Formula (5-2) from the reaction solution according to the currently used separation technique such as the crystallization, but it is preferred from the industrial standpoint to continuously carry out these steps (or the step (c) is carried out without isolating the intermediate of Formula (5-2)).

After the foregoing reaction for forming the quinazoline-dione ring, an alcohol solvent may be added to the reaction system to thus decompose the excess carboxyl group-activating agent present therein. Examples of preferred alcohol solvent to be added include, for instance, methanol or isopropyl alcohol. Moreover, in case of the product having an ester moiety in the molecule, the addition of an alcohol solvent may induce the occurrence of a trans-esterification reaction and therefore, the alcohol solvent should preferably be selected in consideration of the kind of the ester.

Then, in the step (d), the hydrogen atom bonded to the nitrogen atom present in the quinazoline-dione ring of the quinazoline-dione derivative of Formula (6-2) can, if desired, be replaced with an N-alkyl group using an N-alkylation agent and when R23' is protected, the protective group can be removed. These steps may be carried out according to the same procedures used in the step (c) of the first production method. At this stage, preferably used herein as the N-alkylation agent include methyl p-toluene-sulfonate, methyl methane sulfonate, methyl iodide, methyl bromide, and methyl chloride.

In this regard, the N-alkyl-substitution with an N-alkylation agent is preferably carried out under a basic condition.

In the second production method, R23 appearing in Formula (1-2) is preferably either a dimethylamino group or a methyl-aminomethyl group; and R23' appearing in Formulas (4-2) to (6-2) is preferably one of N-formyl-N-methyl-aminomethyl group, N-(tert-butoxycarbonyl)-N-methyl-aminomethyl group, N-acetyl-N-methylamino-methyl group and dimethylamino group.

Moreover, it is preferred in the second production method that 2-(3-{4-[2(S)-2-(2,6-dichlorobenzoylamino)-2-isopropoxycarbonylethyl]phenyl} ureido)-5-(N-formyl-N-methylaminomethyl)benzoic acid of Formula (5-2) in which R21 is a 2,6-dichlorophenyl group, R22 is an isopropyl group, R23' is an N-formyl-N-methyl-aminomethyl group, and R25 is a hydrogen atom is prepared by reacting a compound of Formula (3-2), in which R21 is a 2,6-dichlorophenyl group and R22 is an isopropyl group, with a compound of Formula (4-2), in which R23' is an N-formyl-N-methyl-aminomethyl group and R25 is a hydrogen atom; the resulting benzoic acid is reacted with 1,1'-carbonyldiimidazole as a carboxyl group-activating agent to thus convert the benzoic acid into an $N^\alpha$-(2,6-dichlorobenzoyl)-4-{6-(N-formyl-N-methyl-aminomethyl)-quinazoline-2,4[1H,3H]-dion-3-yl}-L-phenylalanine isopropyl ester represented by Formula (6-2) in which R21 is a 2,6-dichlorophenyl group, R22 is an isopropyl group and R23' is an N-formyl-N-methyl-aminomethyl group; then the isopropyl ester is subjected to N-alkylation using methyl p-toluene-sulfonate to thus convert the same into $N^\alpha$-(2,6-dichlorobenzoyl)-4-{1-methyl-6-(N-formyl-N-methyl-aminomethyl)-quinazoline-2,4[1H,3H]-dion-3-yl}-L-phenylalanine isopropyl ester; and the formyl group of the phenylalanine isopropyl ester is deprotected under an acidic condition using hydrochloric acid to thus give $N^\alpha$-(2,6-dichlorobenzoyl)-4-{1-methyl-6-(N-methyl-aminomethyl)-quinazoline-2,4[1H,3H]-dion-3-yl}-L-phenylalanine isopropyl ester of Formula (1-2) in which R21 is a 2,6-dichlorophenyl group, R22 is an isopropyl group, R23 is an N-methyl-aminomethyl group and R24 is a methyl group, or a hydrochloride thereof.

In this respect, the foregoing N-alkylation with methyl p-toluene-sulfonate is preferably carried out under a basic condition.

Moreover, it is preferred in the second production method that 2-(3-{4-[2(S)-2-(2,6-dichlorobenzoylamino)-2-methylcarbonylethyl]phenyl} ureido)-5-(dimethylamino)-benzoic acid methyl ester of Formula (5-2) in which R21 is a 2,6-dichlorophenyl group, R22 is a methyl group, R23' is a dimethylamino group, and R25 is a methyl group is prepared by reacting a compound of Formula (3-2), in which R21 is a 2,6-dichloro-phenyl group and R22 is a methyl group, with a compound of Formula (4-2), in which R23' is a dimethylamino group and R25 is a methyl group; the resulting benzoic acid methyl ester is reacted with potassium carbonate to thus convert the benzoic acid methyl ester into methyl ester of $N^\alpha$-(2,6-dichlorobenzoyl)-4-{6-dimethylamino-quinazoline-2,4[1H,3H]-dion-3-yl}-L-phenylalanine of Formula (6-2) in which R21 is a 2,6-dichlorophenyl group, R22 is a methyl group, R23 is a dimethylamino group; then the N-alkylation of the resulting methyl ester is carried out using methyl p-toluene-sulfonate to thus give methyl ester of $N^\alpha$-(2,6-dichlorobenzoyl)-4-{1-methyl-6-dimethylamino-quinazoline-2,4[1H,3H]-dion-3-yl}-L-phenylalanine of Formula (1-2) in which R21 is a 2,6-dichlorophenyl group, R22 is a methyl group, R23 is a dimethylamino group and R24 is a methyl group.

In this respect, the foregoing N-alkylation with methyl p-toluene-sulfonate is preferably carried out under a basic condition.

Then the third production method according to the present invention will be described below in more detail.

The third production method according to the present invention has been completed on the basis of such a finding that the amount of the by-product peculiar to and sometimes produced by the first production method can be reduced when a derivative of an isatoic anhydride represented by Formula (2-3) or a chemically acceptable salt thereof as a starting material is reacted with an acyl phenylalanine derivative represented by Formula (3-3) or a chemically acceptable salt thereof to thus obtain an amide derivative of Formula (4-3), followed by preparing a phenylalanine derivative having a quinazoline-dione ring represented by Formula (1-3) or a pharmaceutically acceptable salt thereof as a final target compound, through the amide derivative.

It has commonly been known that the condensation reaction between isatoic anhydride and an amine results in the formation of a corresponding amide derivative thereof (see Science of Synthesis, Vol. 16, p. 658). In the present invention, however, such an amide derivative of Formula (4-3) is synthesized by the reaction of a specific derivative of isatoic anhydride represented by Formula (2-3) or a chemically acceptable salt thereof as a starting material with an acyl phenylalanine derivative represented by Formula (3-3) or a chemically acceptable salt thereof.

In this respect, the derivative of isatoic anhydride represented by Formula (2-3) or a chemically acceptable salt thereof can be prepared by the reaction of an anthranilic acid derivative represented by the following formula (6-3) and carrying an unprotected carboxyl group and an amino group or a chemically acceptable salt thereof with a carbonyl group-introducing reagent:

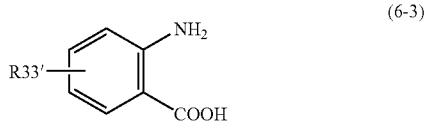

(6-3)

wherein R33' is the same as that defined above.

In this respect, the isatoic anhydride represented by Formula (2-3) can be derived through the reaction of an anthranilic acid derivative of Formula (6-3) or a chemically acceptable salt thereof with N,N'-carbonyl-diimidazole (CDI) or an equivalent thereof (represented by the formula: R—CO—R', in which R and R' represent leaving groups and may be the same or different, and each of R and R' represents, for instance, an imidazole, triazole, succinimidyl group or a halogen atom). At this stage, it is more preferred to use N,N'-carbonyl-diimidazole (CDI).

In this connection, the carboxyl group-activating agent and the conditions for using the same described above in connection with the first production method can be adopted in this third production method, but it is preferred, in the third method, to use 1,1'-carbonyl-diimidazole, 1,1'-carbonyl-triazole or a chloroformate ester.

The protective groups for the substituent of R33' appearing in Formula (6-3) are desirably those capable of withstanding the basic condition and capable of being deprotected under an acidic condition and more preferably used herein are, for instance, formyl group and t-butoxycarbonyl group. Moreover, the dialkylamino group usable herein is more preferably dimethylamino group.

The organic solvent usable in the third production method includes, for instance, N,N-dimethylformamide (DMF), dimethoxyethane (DME), dimethyl sulfoxide (DMSO), dimethyl-acetamide (DMA), acetonitrile, and tetrahydrofuran (THF) and it is selected from organic solvents which are very weakly reactive with N,N'-carbonyl-diimidazole (CDI), with DMF being more preferred among others.

The reaction for forming isatoic anhydride of Formula (2-3) is desirably carried out at a temperature ranging from 0 to 40° C. and particularly preferably 0 to 20° C.

The isatoic anhydride of Formula (2-3) may be isolated from the reaction solution and in this case, the isatoic anhydride can be isolated according to the usual separation technique, for instance, by the extraction with an organic solvent and the subsequent concentration of the extract to dryness. The reaction solution can directly be used in the subsequent condensation reaction without isolating the isatoic anhydride and, for instance, an acyl phenylalanine derivative represented by Formula (3-3) is added to the reaction solution containing the isatoic anhydride of Formula (2-3) and then the resulting mixture is heated to thus give an amide derivative represented by Formula (4-3).

From the industrial standpoint, these steps are preferably continuously carried out without isolating the isatoic anhydride to thus reduce the number of steps required, but the present invention is not restricted to this specific embodiment at all.

The amide derivative represented by Formula (4-3) can also be isolated from the reaction solution according to the currently used separation technique, but the reaction solution containing the amide derivative of Formula (4-3) is directly reacted with a carbonyl group-introducing reagent to thus derive a quinazoline-dione derivative represented by Formula (5-3). From the industrial standpoint, these steps are preferably continuously carried out, but the present invention is not restricted to this specific embodiment at all.

In the condensation reaction of the isatoic anhydride of Formula (2-3) with the acyl phenylalanine derivative of Formula (3-3), examples of reaction solvents used therein are N,N-dimethylformamide (DMF), dimethoxy-ethane (DME), dimethyl sulfoxide (DMSO), dimethyl-acetamide (DMA), acetonitrile, and tetrahydrofuran (THF) as has been described above and it is selected from organic solvents which are very weakly reactive with N,N'-carbonyl-diimidazole (CDI), with DMF being more preferred among others. The reaction temperature desirably ranges from 10 to 100° C. and particularly preferably 50 to 80° C. In this respect, however, the reaction temperature should be determined while taking into consideration the rate of production of the target product (the rate of the disappearance of the raw material) and the formation of by-products and accordingly, the reaction temperature is not restricted to the foregoing specific range. The reaction time in general ranges from about 1 to 12 hours, but the degree of the progress of the reaction is managed or controlled by the usually employed HPLC technique to thus determine the reaction time while taking into consideration the rate of condensate-production and the rate of the consumption of the starting material and accordingly, the reaction time is not restricted to the foregoing specific range.

In this respect, as has been described above in connection with the first production method, the carbonyl group-introducing reagent is preferably 1,1'-carbonyl-diimidazole (CDI), methyl chloroformate, ethyl chloroformate, or phenyl chloroformate and particularly preferred carbonyl group-introducing reagent is 1,1'-carbonyl-diimidazole (CDI).

Then, in the step (c), the hydrogen atom attached to the nitrogen atom present in the quinazoline-dione ring of the resulting quinazoline-dione derivative of Formula (5-3) can, if desired, be replaced with an N-alkyl group using an N-alkylation agent and when R33' is protected, the protective group can be removed. These steps may be carried out according to the same procedures used in the step (c) of the first production method. At this stage, preferably used herein as the N-alkylation agents include methyl p-toluene-sulfonate, methyl methane sulfonate, methyl iodide, methyl bromide, and methyl chloride.

In the third production method, R33 appearing in Formula (1-3) is preferably either a methyl-aminomethyl group or a dimethylamino group; and R33' appearing in Formulas (2-3), (4-3) and (5-3) is preferably one of N-formyl-N-methyl-aminomethyl group, N-(tert-butoxycarbonyl)-N-methyl-aminomethyl group, N-acetyl-N-methyl-aminomethyl group and dimethylamino group.

Moreover, it is preferred in the invention that a compound of Formula (3-3) in which R31 appearing in Formula (3-3) is 2,6-dichlorophenyl group and R32 is an isopropyl group is reacted with a compound of Formula (2-3) in which R33' is an N-formyl-N-methyl-aminomethyl group to thus form 4-{2-amino-5-(N-formyl-N-methyl-aminomethyl)-benzoylamino}-N$^\alpha$-(2,6-dichlorobenzoyl)-L-phenylalanine isopropyl ester of Formula (4-3) in which R31 is 2,6-dichlorophenyl group, R32 is an isopropyl group, and R33' is an N-formyl-N-methyl-aminomethyl group; the resulting isopropyl ester is reacted with 1,1'-carbonyl-diimidazole as a carbonyl group-introducing reagent to thus convert the isopropyl ester into N$^\alpha$-(2,6-dichlorobenzoyl)-4-{6-(N-formyl-N-methyl-aminomethyl)-quinazoline-2,4[1H,3H]-dion-3-yl}-L-phenyl-alanine isopropyl ester of Formula (5-3) in which R31 is a 2,6-dichlorophenyl group, R32 is an isopropyl group and R33' is an N-formyl-N-methyl-aminomethyl group; subsequently the isopropyl ester of Formula (5-3) is subjected to N-alkylation using methyl p-toluene-sulfonate to thus convert the ester into N$^\alpha$-(2,6-dichlorobenzoyl)-4-{1-methyl-6-(N-formyl-N-methylamino-methyl)-quinazoline-2,4[1H,3H]-dion-3-yl}-L-phenylalanine isopropyl ester; and then the formyl group is subjected to a deprotection operation using hydrogen chloride to thus give N$^\alpha$-(2,6-dichlorobenzoyl)-4-{1-methyl-6-(N-methylaminomethyl)quinazoline-2,4[1H,3H]-dion-3-yl}-L-phenylalanine isopropyl ester of Formula (1-3) or the hydrochloride thereof, in which R31 is a 2,6-dichloro-phenyl group, R32 is an isopropyl group and R33 is an N-methyl-aminomethyl group and R34 is a methyl group.

In this respect, the foregoing N-alkylation with methyl p-toluene-sulfonate is preferably carried out under a basic condition.

Moreover, it is preferred, in the present invention, that a compound of Formula (3-3) in which R31 appearing in Formula (3-3) is a 2,6-dichlorophenyl group, and R32 is a methyl group is reacted with a compound of Formula (2-3) in which R33' is a dimethylamino group to thus give 4-{2-amino-5-dimethylamino-benzoylamino}-N$^\alpha$-(2,6-dichlorobenzoyl)-L-phenylalanine methyl ester of Formula (4-3) in which R31 is a 2,6-dichlorophenyl group, R32 is a methyl group and R33' is a dimethylamino group; the resulting methyl ester is reacted with 1,1'-carbonyl-diimidazole as a carbonyl group-introducing reagent to thus convert the methyl ester into N$^\alpha$-(2,6-dichlorobenzoyl)-4-{6-dimethylamino-quinazoline-2,4[1H,3H]-dion-3-yl}-L-phenyl-alanine methyl ester of Formula (5-3) in which R31 is a 2,6-dichlorophenyl group, R32 is a methyl group and R33' is a dimethylamino group; then the resulting methyl ester of Formula (5-3) is subjected to N-alkylation with methyl p-toluene-sulfonate to thus give N$^\alpha$-(2,6-dichlorobenzoyl)-4-{1-methyl-6-dimethylamino-quinazoline-2,4[1H,3H]-dion-3-yl}-L-phenylalanine methyl ester of Formula (1-3) in which R31 is a 2,6-di-chlorophenyl group, R32 is a methyl group, R33 is a dimethylamino group and R34 is a methyl group.

In this respect, the foregoing N-alkylation with methyl p-toluene-sulfonate is preferably carried out under a basic condition.

Then the fourth production method according to the present invention will be described below in more detail.

The fourth production method according to the present invention has been completed on the basis of such a finding that the amount of the by-product peculiar to and sometimes produced by the first production method can be reduced when a benzoxazine derivative represented by Formula (2-4) as a starting material is reacted with an acyl phenylalanine derivative represented by Formula (3-4) or a chemically acceptable salt thereof, then a base is acted on the resulting amide carbamate derivative of Formula (4-4) or a chemically acceptable salt thereof to thus give a quinazoline-dione derivative represented by Formula (5-4), followed by preparing a phenylalanine derivative having a quinazoline-dione ring and represented by Formula (1-4) or a pharmaceutically acceptable salt thereof as a final target compound, through the quinazoline-dione derivative of Formula (5-4).

The benzoxazine derivative represented by Formula (2-4) as the starting material can easily be prepared by the reaction of an anthranilic acid derivative represented by the following formula (6-4) or a chemically acceptable salt thereof with an alkyl haloformate or a phenyl haloformate which may have a substituent according to the method disclosed in a literature (Heterocycle, 1999, 51(7): 1543-1561):

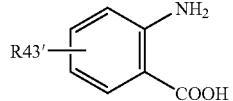

(6-4)

wherein R43' is the same as that defined above.

Preferably used herein as such an alkyl haloformate is chloroformate esters and specific examples thereof usable herein are methyl chloroformate, ethyl chloroformate, phenyl chloroformate, isopropyl chloroformate and benzyl chloroformate, with ethyl chloroformate being more preferably used herein. Moreover, preferably used herein are chloroformate esters which are never accompanied by any side reaction such as trans-esterification. As the substituent on the phenyl group of the phenyl haloformate which may have a substituent, there may be listed, for instance, alkyl groups, alkoxy groups and halogen atoms, but preferably used herein is a phenyl group free of any substituent. The phenyl haloformate which may have a substituent is preferably phenyl chloroformate.

The reaction solvents suitably used herein include, for instance, pyridine, N-methyl-morpholine, N,N-dimethylformamide (DMF) and acetonitrile and more preferably a pyridine solvent. Moreover, when using DMF or acetonitrile as such a solvent, it is also possible to use a mixed solvent to which an organic base or pyridine is added as a base.

The benzoxazine derivative of Formula (2-4) prepared by the reaction of an anthranilic acid derivative of Formula (6-4) or a chemically acceptable salt thereof with an alkyl haloformate can be used in the subsequent step without isolating the benzoxazine derivative from the reaction solution, but the derivative can be isolated according to the usual separation technique. From the industrial standpoint, these steps are advantageously carried out continuously.

In the condensation reaction of a benzoxazine derivative of Formula (2-4) with an acyl phenylalanine derivative of Formula (3-4), the acyl phenylalanine derivative of Formula (3-4) can be added to the reaction solution containing the benzoxazine derivative of Formula (2-4) to thus form a corresponding amide carbamate derivative of Formula (4-4).

Usable herein as reaction solvents are, for instance, DMF, acetonitrile, and pyridine. The reaction temperature preferably ranges from 0 to 80° C. and more preferably about 10 to 30° C., but it is not restricted to the range specified above in the present invention. After the progress of the reaction is confirmed by, for instance, the HPLC technique, the product or the amide carbamate derivative of Formula (4-4) can be isolated according to the commonly used separation technique such as the addition of a poor solvent.

A quinazoline-dione ring can be formed by treating the amide carbamate derivative of Formula (4-4) under a basic condition to thus derive a quinazoline-dione derivative of Formula (5-4). The reaction solvents usable herein include, for instance, DMF, N-methyl-pyrrolidone, acetonitrile, and a DMF/alcohol mixed solvent. As such bases usable herein, there may be listed, for instance, organic bases such as triethylamine and diisopropyl-ethylamine, carbonic acid salts of alkali metals such as potassium carbonate, sodium carbonate, potassium hydrogen carbonate, sodium hydrogen carbonate. Among them, preferably used herein as such a base includes potassium carbonate or sodium methoxide.

The reaction temperature preferably ranges from 10 to 80° C. and more preferably about 20 to 40° C., but the reaction temperature should be determined while taking into consideration the rate of production of the target product (the rate of the disappearance of the raw material) and the formation of by-products and accordingly, the reaction temperature is not restricted to the foregoing specific range.

Then, in the step (c), the hydrogen atom bonded to the nitrogen atom present in the quinazoline-dione ring of the quinazoline-dione derivative of Formula (5-4) is, if desired, replaced with an N-alkyl group using an N-alkylation agent and when R43' is protected, the protective group may be removed. These steps may be carried out according to the same procedures used in the step (c) of the first production method. At this stage, preferably used herein as the N-alkylation agents include methyl p-toluene-sulfonate, methyl methane sulfonate, methyl iodide, methyl bromide, and methyl chloride.

In the fourth production method according to the present invention, it is preferred that, R43 appearing in Formula (1-4) is either a methyl-aminomethyl group or a dimethylamino group, and R43' appearing in Formulas (2-4), (4-4) and (5-4) is an N-formyl-N-methyl-aminomethyl group, an N-(t-butoxycarbonyl)-N-methylamino-methyl group, an N-acetyl-N-methyl-aminomethyl group or a dimethylamino group. In this respect, the foregoing N-alkyl-substitution with methyl p-toluene-sulfonate is preferably carried out under a basic condition.

In addition, it is preferred that a compound of Formula (3-4), in which R41 is a 2,6-dichlorophenyl group and R42 is an isopropyl group, is reacted with a compound of Formula (2-4) in which R43' is an N-formyl-N-methyl-aminomethyl group and R45 is an ethyl group to thus form Nα-(2,6-dichlorobenzoyl)-4-{2-ethoxycarbonyl-amino-5-(N-formyl-N-methylaminomethyl)benzoylamino}-L-phenylalanine isopropyl ester of Formula (4-4) in which R41 is a 2,6-dichlorophenyl group, R42 is an isopropyl group, R43' is an N-formyl-N-methyl-aminomethyl group and R45 is an ethyl group; then the isopropyl ester of Formula (4-4) is reacted with potassium carbonate to thus convert the ester into Nα-(2,6-dichlorobenzoyl)-4-{6-(N-formyl-N-methyl-aminomethyl)quinazoline-2,4[1H,3H]-dion-3-yl}-L-phenylalanine isopropyl ester of Formula (5-4) in which R41 is a 2,6-dichlorophenyl group, R42 is an isopropyl group and R43' is an N-formyl-N-methyl-aminomethyl group; subsequently the isopropyl ester is subjected to N-alkylation using methyl p-toluene-sulfonate to thus convert the ester into Nα-(2,6-dichlorobenzoyl)-4-{1-methyl-6-(N-formyl-N-methyl-aminomethyl)-quinazoline-2,4[1H,3H]-dion-3-yl}-L-phenylalanine isopropyl ester; and finally the formyl group of the resulting isopropyl ester is deprotected with hydrogen chloride to give Nα-(2,6-dichlorobenzoyl)-4-{1-methyl-6-(N-methyl-aminomethyl)-quinazoline-2,4[1H,3H]-dion-3-yl}-L-phenylalanine isopropyl ester or hydrochloride thereof, in which R41 is a 2,6-dichlorophenyl group, R42 is an isopropyl group, R43 is an N-methyl-aminomethyl group and R44 is a methyl group.

In this respect, the foregoing N-alkylation with methyl p-toluene-sulfonate is preferably carried out under a basic condition.

It is also preferred in the invention that a compound of Formula (3-4), in which R41 is a 2,6-dichlorophenyl group and R42 is a methyl group, is reacted with a compound of Formula (2-4) in which R43' is a dimethylamino group and R45 is an ethyl group to thus form Nα-(2,6-dichlorobenzoyl)-4-{2-ethoxycarbonyl-amino-4-dimethyl-amino-benzoylamino}-L-phenylalanine methyl ester of Formula (4-4) in which R41 is a 2,6-dichlorophenyl group, R42 is a methyl group, R43' is a dimethylamino group and R45 is an ethyl group; the resulting methyl ester is reacted with potassium carbonate to thus convert the ester into Nα-(2,6-dichlorobenzoyl)-4-{6-dimethyl-amino-quinazoline-2,4[1H,3H]-dion-3-yl}-L-phenylalanine methyl ester of Formula (4-5) in which R41 is a 2,6-dichlorophenyl group, R42 is a methyl group and R43' is a dimethylamino group; and then the methyl ester is subjected to N-alkylation using methyl p-toluene-sulfonate to thus give Nα-(2,6-dichlorobenzoyl)-4-{1-methyl-6-dimethyl-amino-quinazoline-2,4[1H,3H]-dion-3-yl}-L-phenylalanine methyl ester of Formula (1-4) in which R41 is a 2,6-dichlorophenyl group, R42 is a methyl group, R43 is a dimethyl-aminomethyl group and R44 is a methyl group.

In this respect, the foregoing N-alkylation with methyl p-toluene-sulfonate is preferably carried out under a basic condition.

The present invention will hereunder be described in more detail with reference to the following Examples.

EXAMPLE

First of all, the following is the explanation of the analysis methods adopted in the following Examples and starting materials used therein.
1. Conditions for Analysis or the Like
(1) $^1$H and $^{13}$C NMR spectroscopic analyses were carried out using AVANCE 400 MHz NMR Analysis Device available from Bruker Company or GEMINI 300 MHz NMR Analysis Device available from Varian Company, while using the peak observed for the solvent used for the measurement as a reference.
(2) The HPLC analysis was carried out using LC Series device available from Shimadzu Corporation and the data were processed using software for chromatographic analyses. The following are conditions for HPLC analysis:

Eluting solution: Solution A: 0.1% trifluoroacetic acid-containing aqueous solution; Solution B: 0.1% trifluoroacetic acid-containing acetonitrile solution;
Gradient Conditions: (Solution A/Solution B)=Initially (90/10)–After 25 minutes (10/90)–After 30 minutes (10/90);
Flow Rate: 1.0 mL/min;
Column Used: Reversed phase ODS silica gel column (ODS-2 available from GL Science Company); Column size: φ 4.6 mm (inner diameter)×150 mm (in length);
Column Temperature: 40° C.; Amount of injected sample: 10 μl.
(3) The ion exchange chromatography was carried out using DIONEX (DX-120) available from Dionex Company, and the data were analyzed using software for chromatographic analyses. The eluting solution used was a 1M $Na_2CO_3$/1M $NaHCO_3$=9/1 mixed solution.
(4) The melting point was determined using a differential scanning calorimetric analyzer (DSC) (DSC6200 available from Seiko-Epolead Company). The container used was an SUS sealable container or a simplified sealable container of an aluminum pan.
(5) In the mass spectroscopic (MS) measurement, there was used Thermo Quest TSQ700 available from Seiko-Epolead Company.
(6) The high resolution mass spectroscopic analysis (HRMS) was carried out using MS700V available from JEOL Ltd.
2. Starting Materials or the Like:
The solvents and starting materials used in the following Examples were commercially available ones and they were used without any pre-treatment, unless otherwise specified.
4-Amino-Nα-(2,6-dichlorobenzoyl)-L-phenylalanine methyl ester was synthesized according to the method disclosed in Patent Document 2.

Example 1

Synthesis of 2-amino-5-(N-formyl-N-methyl-aminomethyl)-benzoic acid

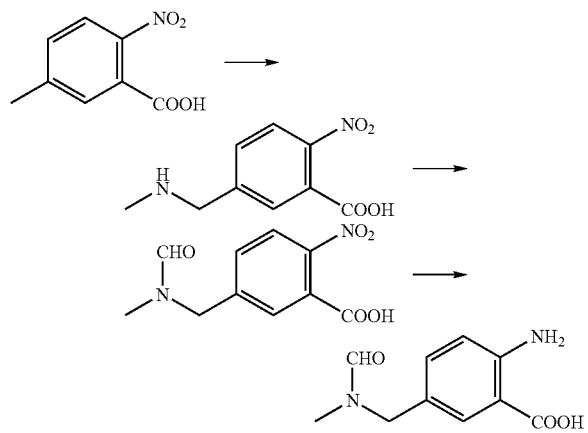

Step 1: Synthesis of 5-(N-methyl-aminomethyl)-2-nitrobenzoic acid (Method 1): Synthesis of 5-(N-methyl-aminomethyl)-2-nitrobenzoic acid using DBH/AIBN and Isolation by Crystallization Through the Addition of 2-Propanol To 100 mL of chlorobenzene, there were added 50 g of 5-methyl-2-nitrobenzoic acid and 36.66 g of 1,3-dibromo-5,5-dimethyl-hydantoin (DBH) to thus form a suspension. The resulting suspension was heated to 40° C. in an argon gas atmosphere, 1.263 g of azobis(2-methylpropionitrile) (AIBN) was added to the suspension and then the mixture was heated to 80° C. After the elapse of one hour, the reaction liquid was once cooled to 40° C., there were again added, to the reaction liquid, 18.33 g of 1,3-di-bromo-5,5-dimethyl-hydantoin and 1.263 g of azobis (2-methylpropionitrile), and the resulting mixture was again heated to 80° C. After 2 hours, the reaction liquid was cooled to 10° C., while stirring the same overnight, the insoluble solid thus separated was filtered off and the latter was washed with 40 mL of chlorobenzene. The filtrate and the washing liquid were combined and the resulting mixture was dropwise added to 260 mL of a 40% methylamine/methanol solution previously cooled to 10° C. over 80 minutes while taking care to prevent the occurrence of any excess heat-generation. Subsequently, the temperature of the reaction liquid was raised up to 25° C., followed by stirring. After the confirmation of the progress of the reaction according to HPLC, the resulting reaction liquid was subjected to distillation under reduced pressure (water bath temperature: 50° C.) to thus concentrate the liquid to half and 150 mL of 2-propanol and seed crystals were added to the concentrated liquid. The mixture was continuously stirred at 50° C. and 100 mL of 2-propanol was added thereto after the desired product was separated. The resulting slurry was again subjected to distillation under reduced pressure to thus concentrate the slurry, the concentrated slurry was stirred at 50° C. for one hour, cooled to 9° C. and then matured for 4 hours. The crystals thus formed were filtered off from the slurry and the crystals in its wet state were washed with 100 mL of 2-propanol. The crystals in its wet state were then dried at 60° C. under reduced pressure to thus give 42.18 g of the title compound as a white crystalline solid (yield: 52%).
$^1$H-NMR (400 MHz, $D_2O$): δ 7.98 (1H, d, J=8.4 Hz), 7.50 (1H, dd, J=8.4, 1.9 Hz), 7.44 (d, 1H, J=1.7 Hz), 4.20 (s, 2H), 2.66 (s, 3H); $^{13}$C-NMR (100 MHz, $D_2O$): δ 173.89, 145.56, 137.84, 136.83, 130.64, 129.07, 125.37, 51.56, 32.92; Melting Point (DSC): Any melting point was not observed, but the compound was decomposed (decomposition-initiation temperature: 239.6° C.); MS (ESI+): m/z 210.8 ($MH^+$), 421.1 (2 $MH^+$); HRMS (FAB): Calculated for $C_9H_{11}N_2O_4$, m/z 211.0719 ($MH^+$), Found m/z: 211.0723 ($MH^+$).

(Method 2): Synthesis of 5-(N-methyl-Aminomethyl)-2-nitrobenzoic Acid by bromination through the use of NBS/BPO and Crystal-Separation Through the Addition of Hydrogen Chloride/Eathyl acetate:

There was suspended, in 25 mL of benzene, 6.12 g of 5-methyl-2-nitrobenzoic acid and then 6.72 g of N-bromo-succinimide (NBS) and 280 mg of a 25% water-containing benzoyl peroxide (BPO) were added to the suspension. The atmosphere of the reaction system was replaced with an argon gas atmosphere and then the resulting mixture was stirred at 80° C. for 3 hours. Thereafter, the reaction liquid was cooled to 10° C., the reaction liquid was dropwise added to 32 mL of a 40% methylamine solution in methanol and the mixture was stirred at room temperature overnight. The reaction liquid was subjected to distillation under reduced pressure to reduce the reaction liquid to about half, and then 23.5 mL of hydrogen chloride/ethyl acetate (3M) was added to the reaction liquid. The solid precipitated out was filtered off and washed with 50 mL of ethyl acetate. Then the solid was dried under reduced pressure to thus give 8.08 g of the title compound as a crystalline solid (as a mixture with methylamine hydrochloride). The physical properties determined were almost identical to those observed for the same compound prepared in the foregoing synthesis Example. Step 2: Synthesis of 5-(N-formyl-N-methyl-aminomethyl)-2-nitrobenzoic acid To a 100 mL volume egg plant-shaped flask, there were added 4.0 mL of formic acid and 2.7 mL of acetic anhydride and the mixture was stirred at room temperature. Subsequent to this, 0.65 g of sodium formate and 5.58 g (content: 71.7 wt %) of 5-(N-methyl-aminomethyl)-2-nitrobenzoic acid were added to the foregoing mixture in two portions and then the resulting mixture was stirred at room temperature for one hour. After the confirmation of the progress of the reaction by HPLC, 32 mL of water was added thereto to separate out crystals and to form a slurry and then cooled to 9° C. and stirred overnight. The solid separated out of the reaction liquid was filtered off, washed with water, dried under reduced pressure to thus obtain 3.95 g of the title compound as a white crystalline solid (yield: 87%).

$^1$H-NMR (400 MHz, DMSO-$d_6$): δ 8.32 and 8.19 (two s, 1H), 8.02 and 7.99 (two d, 1H, J=8.3 Hz), 7.74 and 7.67 (two d, 1H, J=1.8 Hz), 7.65 and 7.59 (two dd, 1H, J=8.3, 1.9 Hz), 4.62 and 4.58 (two s, 2H), 2.90 and 2.66 (two s, 3H); $^{13}$C-NMR (100 MHz, DMSO-$d_6$): δ 166.11, 166.05, 163.39, 163.32, 147.63, 147.33, 143.18, 143.01, 131.37, 131.23, 128.99, 128.85, 128.08, 128.06, 124.50, 124.41, 51.31, 46.26, 34.18, 29.18; Melting Point (DSC): 174.8° C.; MS (ESI+): m/z 239 (MH$^+$), 477.1 (2 MH$^+$); HRMS (FAB): Calculated for $C_{10}H_{11}N_2O_5$, m/z 239.0688 (MH$^+$), Found m/z: 239.0667 (MH$^+$).

Step 3: Synthesis of 2-amino-5-(N-formyl-N-methyl-aminomethyl)benzoic acid

To two-necked 100 mL volume egg plant-shaped flask, there were added 6.98 g (content: 85.9%) of 5-(N-formyl-N-methyl-aminomethyl)-2-nitrobenzoic acid and 48 mL of methanol at room temperature to thus give a suspension and then 3.5 mL of a 6M sodium hydroxide aqueous solution was added to the suspension to thus form a solution (pH: 5.6). After the addition of 1.028 g (0.9 mole % relative to the starting material) of 5% palladium on carbon (wet product) was added to the solution in an argon gas atmosphere, the gas phase was replaced with hydrogen gas and the mixture was heated to 40° C. After 5 hours, the progress of the reaction was confirmed by HPLC (the disappearance of the starting material), the catalyst was filtered off and the catalyst remaining on the filter was washed with 18 mL of methanol. The resulting filtrate and the wash liquid were combined, the solvent was distilled off under reduced pressure at 40° C. till the concentration reached 2 L/kg and then 48 mL of water was added. To the resulting concentrate, there was added 11.0 mL of a 2M hydrochloric acid aqueous solution at room temperature to thus separate out crystals (pH: 2 to 3). The resulting slurry was cooled to 9° C., the crystals were filtered off after stirring the slurry overnight and then the crystals were washed with 24 mL of water. The resulting crystals were dried under reduced pressure at 60° C. to thus give 4.84 g of the title compound as a white crystalline solid (yield: 92%).

$^1$H-NMR (400 MHz, DMSO-$d_6$): δ 8.49 (bs, 2H), 8.25 and 8.08 (two s, 1H), 7.60 and 7.59 (two d, 1H, J=2.1 Hz), 7.14 and 7.10 (two dd, 1H, J=8.5, 2.3 Hz), 6.76 and 6.72 (two d, 1H, J=8.4 Hz), 4.27 (s, 2H), 2.77 and 2.58 (two s, 3H); $^{13}$C-NMR (100 MHz, DMSO-$d_6$): δ 169.55, 169.52, 162.67, 162.62, 151.24, 151.00, 134.03, 133.65, 131.01, 130.76, 122.60, 122.54, 117.01, 116.88, 109.49, 109.48, 51.75, 46.14, 33.48, 28.60; Melting Point (DSC): 174.2° C.; MS (ESI+): m/z 231.3 (MH$^+$), 417.2 (2 MH$^+$); HRMS (FAB): Calculated for $C_{10}H_{13}N_2O_3$, m/z 209.0926 (MH$^+$), Found m/z: 209.0950 (MH$^+$).

Example 2

Synthesis of 2-amino-5-dimethylamino-benzoic acid (Method 1): Synthesis of the Title Compound Starting from 5-Dimethylamino-2-nitrobenzoic acid under Basic Conditions According to the Catalytic Reduction

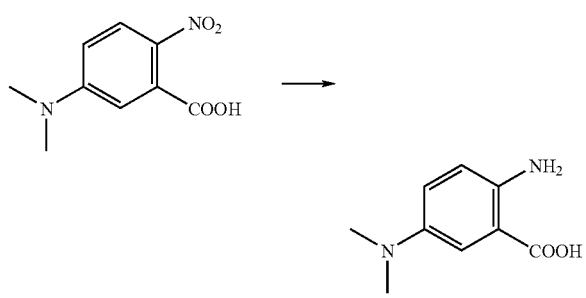

To 1.0 g of 5-dimethylamino-2-nitrobenzoic acid, there were added 16 mL of methanol and 0.79 mL of a 6M sodium hydroxide aqueous solution, then the mixture was heated to 40° C. to give a uniform solution. Subsequently, 0.21 g of 5% palladium on carbon (wet product) was added to the solution in an argon gas atmosphere, and hydrogen gas was introduced into the mixture to thus react with them. After the elapse of 5 hours, the progress of the reaction was confirmed by HPLC, then the catalyst was filtered off under reduced pressure and washed with 10 mL of methanol. The combined filtrate and wash liquid was neutralized by the addition of 0.79 mL of a 6M aqueous solution of hydrochloric acid (pH: 5.5), and then the solvent was distilled off under reduced pressure to thus precipitate out solid. To the resulting suspension, there was added 10 mL of water and the mixture was stirred at 10° C. for one hour. The crystals thus formed were separated through the filtration under reduced pressure, washed with 10 mL of water, and then dried at 60° C. for 12 hours under reduced pressure to thus give 0.56 g of the title compound as a solid.

$^1$H-NMR (400 MHz, DMSO-$d_6$): δ 8.21 (bs, 3H), 7.10 (d, 1H, J=2.8 Hz), 6.97 (dd, 1H, J=9.1, 2.8 Hz), 6.70 (d, 1H, J=9.1 Hz), 2.72 (s, 6H); $^{13}$C-NMR (100 MHz, DMSO-$d_6$): δ 168.89, 144.55, 141.61, 123.29, 117.90, 114.78, 110.11, 41.95; MS (ESI+): m/z 181.3 (MH$^+$), (ESI−): m/z 179.2 (M−H$^-$).

(Method 2): The title compound was prepared starting from 2-amino-5-dimethylamino-benzoic acid methyl ester.di-hydrochloride through the hydrolysis under a basic condition

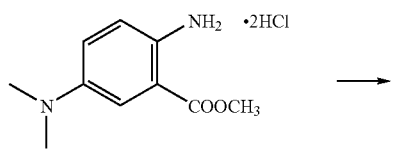

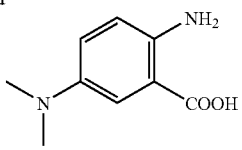

To 5.0 g of 2-amino-5-dimethylamino-benzoic acid methyl ester-di-hydro-chloride, there were added 15 mL of water and 15.6 mL of a 6M aqueous solution of sodium hydroxide and the resulting mixture was heated to 40° C. for 2 hours. After the confirmation of the progress of the reaction according to HPLC, the reaction system was cooled to room temperature, a 6M hydrochloric acid aqueous solution was dropwise added to the reaction system to thus neutralize the same and to separate out crystals (pH 4.9) and then the reaction system was stirred at 10° C. for 2 hours. The solid thus obtained was isolated through the filtration under reduced pressure, washed with 30 mL of water and then dried under reduced pressure at 60° C. for 14 hours to thus obtain 3.14 g of the title compound as a gray-colored solid. The physical properties determined were almost identical to those observed for the same compound prepared in the foregoing synthesis Example.

Example 3

Synthesis of 2-amino-5-(N-tert-butoxycarbonyl-N-methyl-aminomethyl)benzoic acid

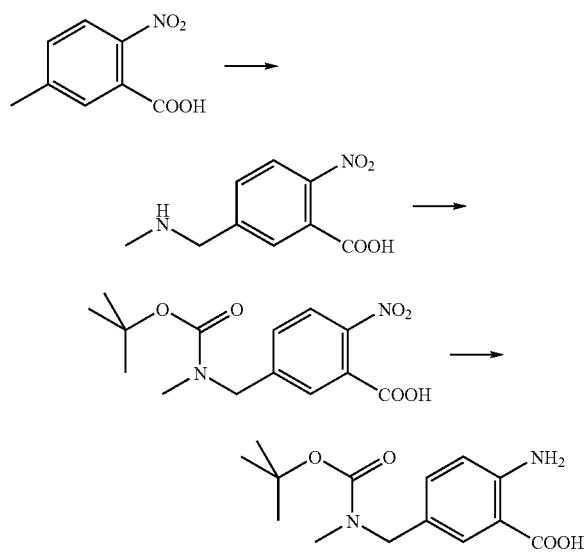

Step 1: Synthesis of 5-methyl-aminomethyl-2-nitrobenzoic acid.hydrochloride

To 260 mL of benzene, there were added 29.52 g of 5-methyl-2-nitrobenzoic acid, 31.10 g of N-bromo-succinimide and 1.00 g of benzoyl peroxide and the resulting mixture was heated, with stirring, at 70° C. overnight. After the confirmation of the progress of the reaction according to HPLC, the reaction solution was cooled to a temperature near room temperature and then concentrated using an evaporator. To the residue remaining after the concentration, there were added 300 mL of water and 300 mL of ethyl acetate to thus extract the product into the organic phase. The organic phase was washed three times with 200 mL of water, a small amount of magnesium sulfate was added to the organic phase to dehydrate the same and then the organic phase was concentrated by an evaporator. The resulting oily product was dissolved in 200 mL of an acetonitrile solution and the solution was dropwise added to 400 mL of a 2M methylamine solution in THF in an ice-bath. After the completion of the dropwise addition, the mixture was concentrated by an evaporator, 300 mL of ethyl acetate was added to the resulting residue and then 250 mL of a 4M hydrogen chloride solution in ethyl acetate was added thereto. The resulting crystals were filtered off and then dried under reduced pressure to thus give 33.57 g of a mixture of the title compound and methylamine hydrochloride (ratio=1:3). This mixture was added to 500 mL of 2-propanol, heated to 70° C. with stirring, then gradually cooled from room temperature to 10° C. and the resulting precipitates were collected.

Step 2: Synthesis of 5-(N-tert-butoxycarbonyl-N-methyl-aminomethyl)-2-nitrobenzoic acid To 25 mL of acetonitrile, there were added 2.46 g of 5-methyl-aminomethyl-2-nitrobenzoic acid.hydrochloride prepared in the foregoing Step 1 and 2.40 g of di-tert-butyl dicarbonate and then 3.5 mL of triethylamine was added and the resulting mixture was stirred for 3 hours at room temperature. After the confirmation of the progress of the reaction, the mixture was concentrated by an evaporator, the resulting residue was diluted by the addition of 100 mL of ethyl acetate and there were then added, to the diluted residue, 100 mL of water and 10 mL of a 2M sodium hydroxide solution. The intended product was extracted with water, the water phase was weakly acidified by the addition of ethyl acetate and a 2M hydrochloric acid solution to thus extract the desired product in the organic phase. After the organic phase was washed with a saturated common salt aqueous solution, the organic phase was subjected to a dehydration treatment with sodium sulfate, then concentrated to dryness using an evaporator and dried under reduced pressure to thus give 2.214 g of the title compound as a pale yellow solid (yield: 71%).

$^1$H-NMR (300 MHz, DMSO-$d_6$): δ 10.76 (bs, 1H), 7.89 (d, 1H, J=8.4 Hz), 7.68 (s, 1H), 7.51 (d, 1H, J=7.5 Hz), 4.55 (s, 2H), 2.90 (bs, 3H), 1.48 (s, 9H).

Step 3: Synthesis of 2-amino-5-(N-tert-butoxycarbonyl-N-methyl-aminomethyl)-benzoic acid To 80 mL of methanol, there were added 8.3 g of 5-(N-tert-butoxycarbonyl-N-methyl-aminomethyl)-2-nitrobenzoic acid prepared in the foregoing Step 2 and 500 mg of 10% Pd/C (wet product), then hydrogen gas was introduced into the resulting dispersion and the mixture was then stirred at room temperature. After 1.5 hours, additional 500 mg of 10% Pd/C was further added to the mixture and the latter was stirred over 7 hours in a hydrogen gas atmosphere. The catalyst was removed by the filtration through Celite and the Celite was washed with methanol. The filtrate was concentrated to dryness to thus give the title compound.

$^1$H-NMR (300 MHz, DMSO-d$_6$): δ 7.62 (bs, 1H), 7.11 (d, 1H, J=6.6 Hz), 6.80 (d, 1H, J=8.1 Hz), 4.18 (s, 2H), 2.69 (s, 3H), 1.41 (s, 9H); MS (ES+): m/z 281.0 (MH$^+$).

Example 4

Synthesis of 4-amino-N$^α$-(2,6-dichlorobenzoyl)-L-phenylalanine isopropyl ester

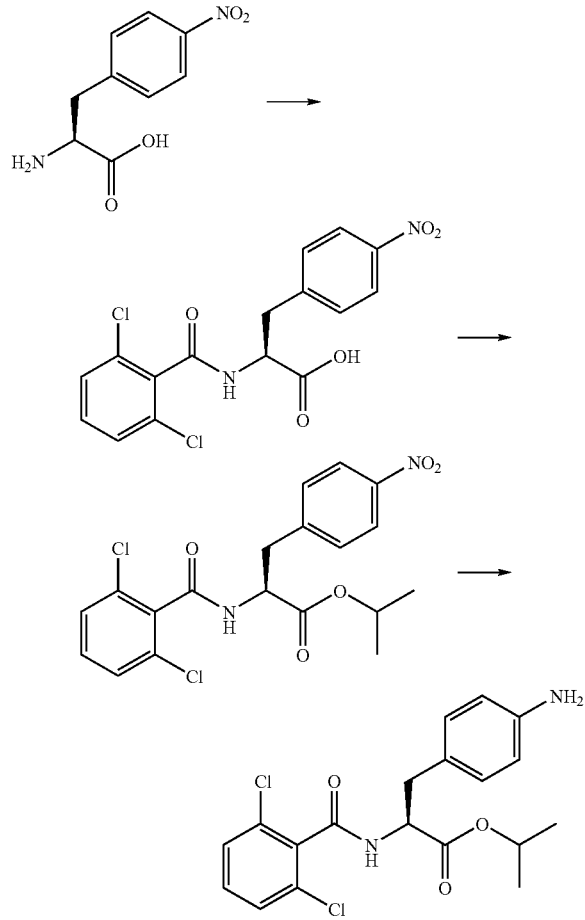

Step 1: Synthesis of N$^α$-(2,6-dichlorobenzoyl)-4-nitro-L-phenylalanine

To 13 mL of acetone, there were added 10.04 g of p-nitro-L-phenylalanine and 28 mL of water to thus form a suspension and the latter was cooled in an ice-bath. To this suspension, there were alternatively dropwise added 18.4 mL of a 6M sodium hydroxide solution and 10.05 g of 2,6-dichlorobenzoyl chloride in such a manner that the pH value of the suspension was maintained at a level of not less than 13 at a temperature of not more than 15° C. After the completion of the dropwise addition, the suspension was further stirred for 2 hours with cooling in an ice-bath, then the progress of the reaction was confirmed by HPLC and 36 mL of a 2M hydrochloric acid solution was dropwise added while taking care to prevent any excess generation of heat. The suspension containing separated solid matter was stirred at 10° C. overnight, the precipitates were isolated through filtration and then dried under reduced pressure at 60° C. to thus obtain 17.32 g of the title compound as a white crystalline solid (yield: 95%).

$^1$H-NMR (400 MHz, DMSO-d$_6$): δ 9.13 (d, 1H, J=8.3 Hz), 8.16 (m, 2H), 7.59 (d, 2H, J=8.4 Hz), 7.42 (m, 3H), 4.79 (m, 1H), 3.30 (m, 1H), 3.06 (m, 1H); $^{13}$C-NMR (100 MHz, DMSO-d$_6$): δ 172.08, 163.56, 146.50, 146.00, 136.18, 131.33, 131.19, 130.88, 128.19, 123.37, 93.39, 52.98, 36.55; Melting Point (DSC): 220.6° C.; MS (ESI+, m/z): 383.0 (MH$^+$), 385.1 (MH$^+$).

Step 2: Synthesis of N$^α$-(2,6-dichlorobenzoyl)-4-nitro-L-phenylalanine isopropyl ester (Method 1): Esterification Reaction with Methane-Sulfonic Acid and Isolation/Drying To 359 mL of 2-propanol, there was suspended 35.90 g of N$^α$-(2,6-dichlorobenzoyl)-4-nitro-L-phenylalanine prepared in the foregoing method and 6.0 mL of methane-sulfonic acid was added to the suspension. After stirring the suspension at 60° C. for 19 hours, it was cooled to room temperature and the resulting crystals were recovered through filtration. The resulting wet crystals were dried under reduced pressure at 60° C. to thus give 38.29 g of the title compound as a white crystalline solid (yield: 96%).

$^1$H-NMR (400 MHz, DMSO-d$_6$): δ 9.21 (d, 1H, J=8.1 Hz), 8.16 (d, 2H, J=8.7 Hz), 7.60 (d, 2H, J=8.7 Hz), 7.46-7.38 (m, 3H), 4.95 (m, 1H), 4.82 (m, 1H), 3.27 (m, 1H), 3.08 (m, 1H), 1.22 (d, 3H, J=6.2 Hz), 1.18 (d, 3H, J=6.2 Hz); $^{13}$C-NMR (100 MHz, DMSO-d$_6$): δ 170.05, 163.50, 146.54, 145.63, 136.03, 131.31, 131.28, 130.91, 128.22, 123.38, 68.67, 53.13, 36.38, 21.71, 21.65; Melting Point (DSC): 188.2° C.; MS (ESI+, m/z): 425.1 (MH$^+$), 427.0 (MH$^+$).

(Method 2): Connection of Esterification Reaction with Methane-Sulfonic Acid with Subsequent Step through Elimination of Drying Step To 150 mL of 2-propanol, there was added 14.92 g of N$^α$-(2,6-dichlorobenzoyl)-4-nitro-L-phenylalanine at room temperature to thus give a suspension. To the suspension, there was added 2.5 mL of methane-sulfonic acid, the resulting mixture was heated, with stirring, to 65° C. over 16 hours. After the confirmation of the progress of the reaction according to HPLC, the reaction solution was cooled to room temperature and the precipitated solid was isolated through filtration. The crystals were washed with 75 mL of 2-propanol to thus give the title compound as white wet crystals. The wet crystals were used in the subsequent step (a reducing reaction of the nitro group) without drying the same.

Step 3: Synthesis of 4-amino-N$^α$-(2,6-dichlorobenzoyl)-L-phenylalanine isopropyl ester To 80 mL of tetrahydrofuran, there was added 31.3 g (content: about 50 wt %) of the wet crystals of N$^α$-(2,6-dichlorobenzoyl)-4-nitro-L-phenylalanine isopropyl ester at room temperature in a nitrogen gas atmosphere and the mixture was then stirred. To the mixture, there were added 80 mL of 2-propanol and 0.86 g of 3% Pt—S/C (wet product, obtained by applying platinum onto carbon and then poisoning the same with sulfur), hydrogen gas was then introduced into the reaction system and the reaction system was stirred at ordinary pressure. The reaction system was stirred at room temperature overnight as it was, and then the catalyst was removed from the reaction solution by filtration through Celite after the confirmation of the progress of the reaction according to HPLC. The resulting filtrate (initial amount of 178 g) was concentrated by distilling the solvent off under reduced pressure till the amount of the filtrate reached 91 g and 40 mL of 2-propanol was added to the concentrate to thus adjust the concentration of the condensate. To this liquid whose concentration had been adjusted, there was dropwise added 150 mL of water at room temperature to thus separate out a crystalline solid and the resulting suspension was maintained at a temperature of not higher than 10° C. overnight. The resulting crystals were filtered off, washed with 100 mL of water and the resulting wet crystals were dried at 60° C. under reduced pressure to thus give 13.16 g of the title compound as a white crystalline solid (overall yield of these two steps: 86%).

$^1$H-NMR (400 MHz, DMSO-$d_6$): δ 9.10 (d, 1H, J=7.7 Hz), 7.47-7.38 (m, 3H), 6.90 (d, 2H, J=8.2 Hz), 6.46 (d, 2H, J=8.3 Hz), 4.95-4.80 (m, 3H), 4.52 (m, 1H), 2.88 (m, 1H), 2.78 (m, 1H), 1.19 (d, 3H, J=6.2 Hz), 1.12 (d, 3H, J=6.2 Hz); $^{13}$C-NMR (100 MHz, DMSO-$d_6$): δ 170.63, 163.54, 147.33, 136.33, 131.47, 131.12, 129.77, 128.15, 123.76, 113.90, 68.09, 54.57, 36.39, 21.75, 21.61; Melting Point (DSC): 115.3° C.; MS (ESI+, m/z): 395.0 (MH$^+$), 397.1 (MH$^+$).

Example 5

Synthesis of N$^α$-(2,6-dichlorobenzoyl)-4-{1-methyl-6-(N-methylamino-methyl)-quinazoline-2,4[1H,3H]-dion-3-yl}-L-phenylalanine isopropyl ester.hydrochloride through intermediate using formyl group as protective group

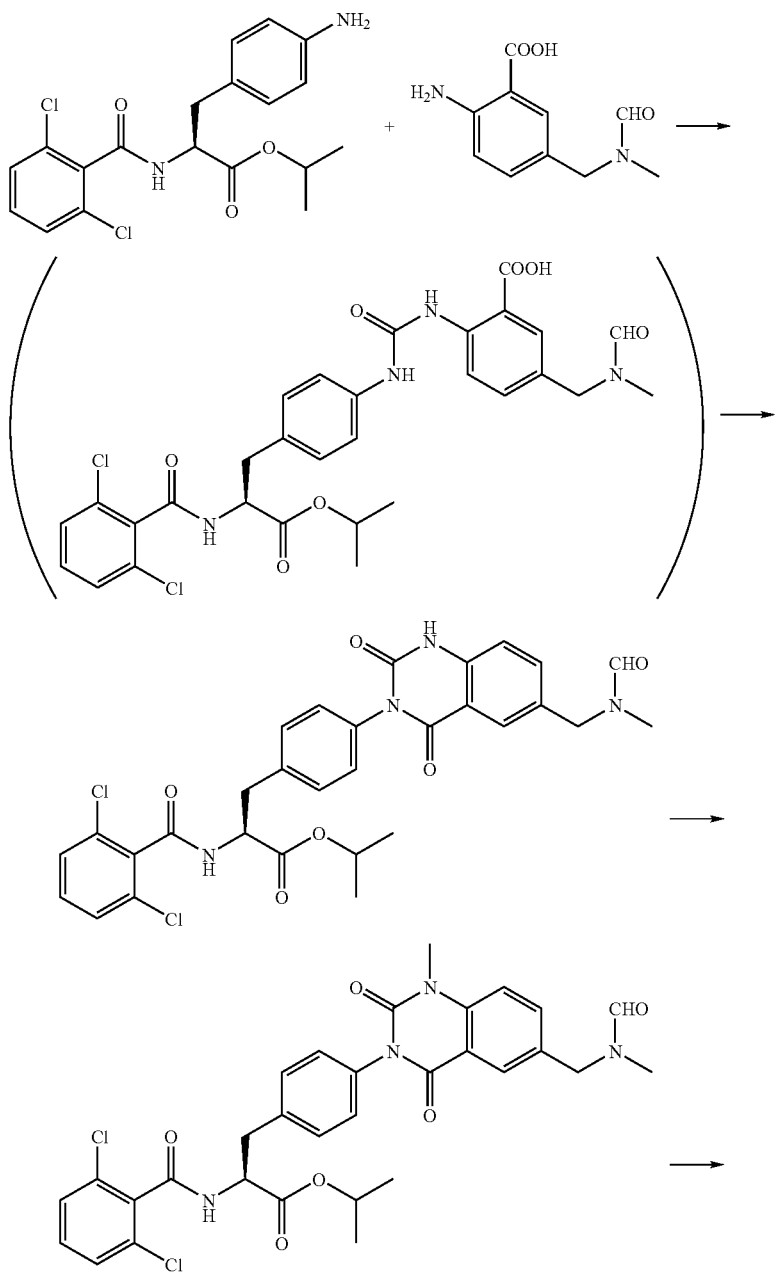

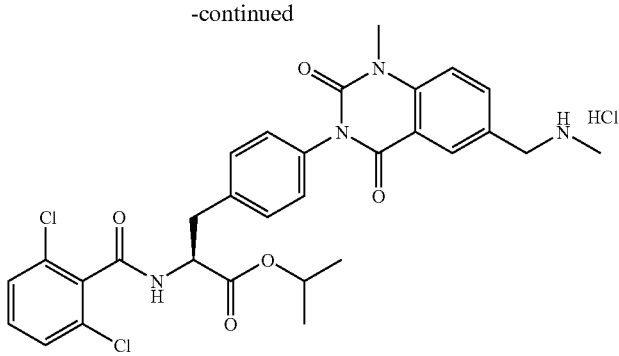

Step 1: Synthesis of N^α-(2,6-dichlorobenzoyl)-4-{6-(N-formyl-N-methylamino-methyl)-quinazoline-2,4[1H,3H]-dion-3-yl}-L-phenylalanine isopropyl ester

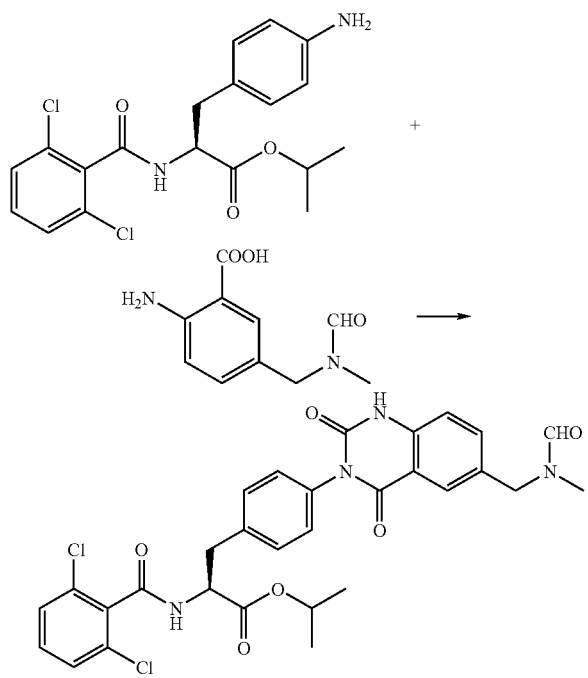

To 7.6 L of N,N-dimethylformamide, there was added 1.74 kg of 1,1'-carbonyl-diimidazole (CDI) in a nitrogen gas stream and the mixture was cooled to 5° C. There was introduced, into this solution, 4.00 kg of 4-amino-N^α-(2,6-dichlorobenzoyl)-L-phenylalanine isopropyl ester in three portions while taking care to prevent any excess generation of heat. Subsequently, the resulting mixture was stirred at a temperature ranging from 5 to 10° C. for 1.5 hours, 2.11 kg of 2-amino-5-(N-formyl-N-methylamino-methyl)-benzoic acid was then added to the mixture, followed by stirring with heating at 60° C. for one hour. After the confirmation of the progress of the urea bond-forming reaction by HPLC, the reaction liquid was cooled to 15° C., 1.99 kg of 1,1'-carbonyl-diimidazole (CDI) was added in three portions while taking care to prevent the occurrence of any foaming and the resulting mixture was stirred at 60° C. After the confirmation of the progress of the quinazoline-dione ring-forming reaction by HPLC, 32 L of 2-propanol was dropwise added to the reaction liquid at 50° C. and then 2 g of seed crystals were added thereto. The resulting suspension containing the product was cooled to 25° C. and an additional 40.01 L of 2-propanol was further dropwise added.

After the suspension was ripened at a temperature ranging from 10 to 15° C. overnight, the crystalline solid thus formed was separated by the filtration using a centrifuge and the resulting cake was washed with 8 L of 2-propanol. The cake was dried at 70° C. under reduced pressure to thus obtain 5.45 kg of the title compound as a white crystalline solid (yield: 88%).

$^1$H-NMR (400 MHz, DMSO-$d_6$): δ 11.53 (bs, 1H), 9.24 (d, 1H, J=7.9 Hz), 8.33 and 8.15 (two s, 1H), 7.86 and 7.81 (two d, 1H, J=1.8 Hz), 7.61 and 7.56 (two dd, 1H, J=8.3, 1.9 Hz), 7.48-7.36 (m, 5H), 7.26-7.18 (m, 3H), 4.95 (septet, 1H, J=6.2 Hz), 4.76 (ddd, 1H, J=9.8, 8.2, 5.4 Hz), 4.50 and 4.48 (two s, 2H), 3.18 (dd, 1H, J=5.2, 14.0 Hz), 3.01 (dd, 1H, J=14.0, 9.9 Hz), 2.83 and 2.62 (two s, 3H), 1.23 (d, 3H, J=6.2 Hz), 1.19 (d, 3H, J=6.2 Hz); $^{13}$C-NMR (100 MHz, DMSO-$d_6$): δ 170.51, 163.67, 162.99, 162.92, 162.21, 150.29, 139.52, 139.25, 137.12, 136.25, 135.14, 134.95, 134.27, 131.61, 131.32, 131.23, 131.14, 129.75, 128.93, 128.13, 126.98, 126.96, 115.92, 115.82, 114.53, 114.48, 68.51, 53.77, 51.52, 46.12, 36.44, 33.71, 28.80, 21.76, 21.68; Melting Point (DSC): 185.8° C.; MS (ESI+): m/z 611 (MH$^+$) and 633.1 (M+Na); (ESI−): m/z 609.1 (M−H$^−$); MS (FAB): m/z 611.0 (MH$^+$); HRMS (FAB): Calculated for $C_{30}H_{29}Cl_2N_4O_6$, m/z 611.1464 (MH$^+$), Found m/z: 611.1461 (MH$^+$).

In this respect, the asymmetric urea derivative which is not isolated in this step can be isolated according to the method disclosed in another Example.

Step 2: Synthesis of N^α-(2,6-dichlorobenzoyl)-4-{1-methyl-6-(N-formyl-N-methylamino-methyl)-quinazoline-2,4[1H,3H]-dion-3-yl}-L-phenylalanine isopropyl ester

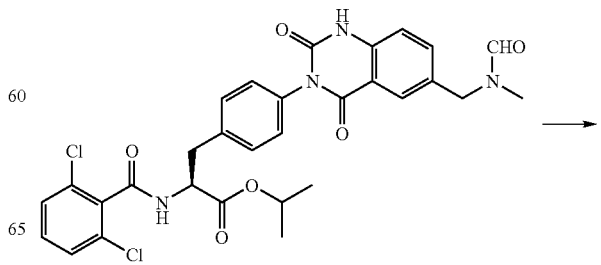

-continued

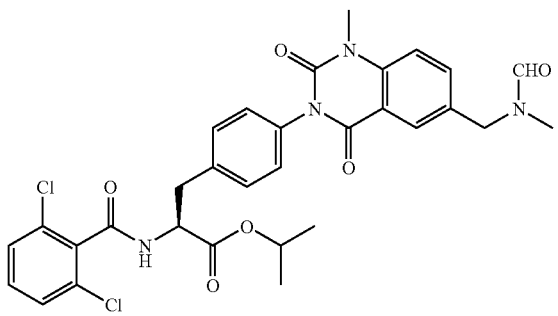

There was added, to 21.26 L of N,N-dimethylformamide (DMF), 5.445 kg of N$^\alpha$-(2,6-dichlorobenzoyl)-4-{6-(N-formyl-N-methylamino-methyl)-quinazoline-2,4[1H,3H]-dion-3-yl}-L-phenylalanine isopropyl ester, the resulting mixture was stirred at 23° C. and in a nitrogen gas stream to dissolve the isopropyl ester compound. Then 2.46 kg of potassium carbonate and 2.491 kg of methyl p-toluene-sulfonate were added to the resulting solution and the mixture was stirred with heating at 55 to 65° C. After the confirmation of the progress of the N-methylation reaction by HPLC, 2.14 kg of acetic acid was added to the mixture and subsequently the mixture was stirred with heating at 50° C. for one hour. To the reaction solution, there was dropwise added 10.9 L of water, followed by the addition of 6 g of seed crystals and stirring of the mixture at 50° C. for 2 hours. To the resulting slurry, there was further added 10.9 L of water, the mixture was cooled to 25° C. and stirred overnight. The precipitates thus obtained were recovered by the filtration using a centrifuge and the resulting cake was washed with 21.8 kg of water. The resulting wet crystals were dried under reduced pressure at 60° C. to thus give 5.235 kg of the title compound as a white crystalline solid (yield: 94%).

$^1$H-NMR (400 MHz, DMSO-d$_6$): δ 9.25 (d, 1H, J=8.0 Hz), 8.36 and 8.16 (two s, 1H), 7.97 and 7.92 (two d, 1H, J=2.2 Hz), 7.73 and 7.67 (two dd, 1H, J=8.6, 2.2 Hz), 7.53 and 7.50 (two d, 1H, J=8.7 Hz), 7.47-7.37 (m, 5H), 7.20 (dd, 2H, J=8.4, 2.4 Hz), 4.95 (septet, 1H, J=6.2 Hz), 4.77 (ddd, 1H, J=9.9, 8.1, 5.2 Hz), 4.55 and 4.53 (two s, 2H), 3.53 and 3.52 (two s, 3H), 3.19 (dd, 1H, J=14.1, 5.2 Hz), 3.02 (dd, 1H, J=14.2, 10.0 Hz), 2.84 and 2.63 (two s, 3H), 1.23 (d, 3H, J=6.2 Hz), 1.19 (d, 3H, J=6.2 Hz); $^{13}$C-NMR (100 MHz, DMSO-d$_6$): δ 170.54, 163.71, 163.02, 162.94, 161.38, 150.57, 140.47, 140.20, 137.20, 136.27, 135.30, 135.13, 134.82, 131.64, 131.61, 131.54, 131.12, 129.84, 128.75, 128.10, 127.34, 127.30, 115.65, 115.59, 115.40, 115.28, 68.54, 53.75, 51.31, 45.97, 36.47, 33.77, 30.93, 30.90, 28.84, 21.75, 21.68; Melting Point (DSC): 118.1° C.; MS (ESI): m/z 625.1 (MH$^+$); MS (FAB): m/z 625.1 (MH$^+$); HRMS (FAB): Calculated for C$_{31}$H$_{31}$Cl$_2$N$_4$O$_6$, m/z 625.1635 (MH$^+$), Found m/z: 625.1621 (MH$^+$).

Step 3: Synthesis of N$^\alpha$-(2,6-dichlorobenzoyl)-4-{1-methyl-6-(N-methylamino-methyl)-quinazoline-2,4[1H,3H]-dion-3-yl}-L-phenylalanine isopropyl ester. hydrochloride

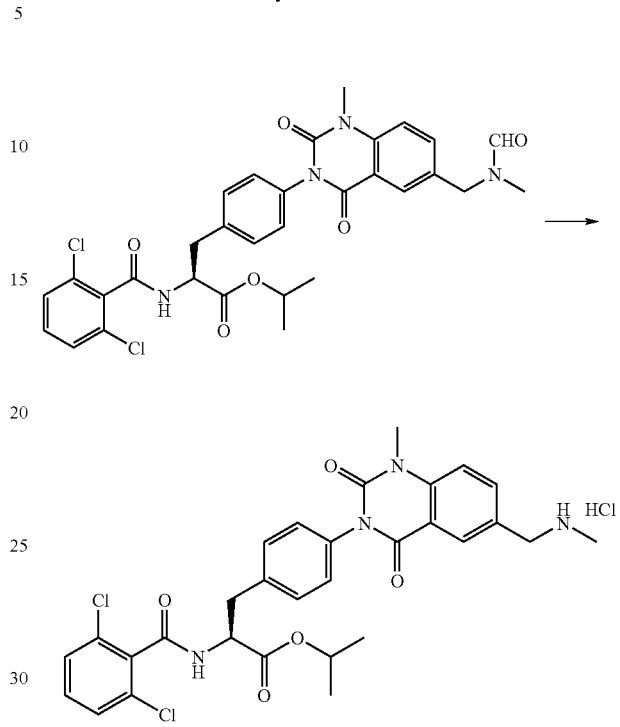

To 61.67 L of 2-propanol, there was added 5.226 kg of N$^\alpha$-(2,6-dichlorobenzoyl)-4-{1-methyl-6-(N-formyl-N-methylamino-methyl)-quinazoline-2,4[1H,3H]-dion-3-yl}-L-phenylalanine isopropyl ester to thus form a suspension and the resulting suspension was cooled to 10° C. and stirred in a nitrogen gas stream. Acetyl chloride (10.00 kg) was dropwise added to this suspension over one hour while taking care to prevent any excess generation of heat, then 37.67 L of isopropyl acetate was added to the suspension and the resulting mixture was heated with stirring at 70° C. for 24 hours. After the confirmation of the progress of the reaction by HPLC, the slurry was cooled to 25° C. and stirred over 19 hours. The resulting precipitates were recovered by the filtration using a centrifuge and the resulting cake was washed with 20.90 L of 2-propanol. The resulting wet crystals were dried under reduced pressure at 75° C. to thus give 5.159 kg of the title compound as a white crystalline solid (yield: 95%).

$^1$H-NMR (400 MHz, DMSO-d$_6$): δ 9.45 (bs, 2H), 9.26 (d, 1H, J=8.0 Hz), 8.23 (d, 1H, J=2.1 Hz), 8.02 (dd, 1H, J=2.0, 8.7 Hz), 7.58 (d, 1H, J=8.8 Hz), 7.38-7.47 (m, 5H), 7.21 (d, 2H, J=8.3 Hz), 4.95 (m, 1H), 4.77 (m, 1H), 4.21 (bs, 2H), 3.55 (s, 3H), 3.19 (dd, 1H, J=5.2, 14.1 Hz), 3.02 (dd, 1H, J=10.0, 14.0 Hz), 2.52 (s, 3H), 1.23 (d, 3H, J=6.2 Hz), 1.19 (d, 3H, J=6.2 Hz); $^{13}$C-NMR (100 MHz, DMSO-d$_6$): δ 170.54, 163.71, 161.26, 150.59, 141.17, 137.45, 137.25, 136.22, 134.75, 131.60, 131.19, 130.09, 129.88, 128.73, 128.13, 126.68, 115.47, 115.27, 68.55, 53.76, 50.18, 36.44, 31.94, 31.05, 21.77, 21.70; Melting Point (DSC): 254-258° C.; MS (ESI): m/z 597.2 (MH$^+$); MS (FAB): m/z 597.1 (MH$^+$); HRMS (FAB): Calculated for C$_{30}$H$_{31}$Cl$_2$N$_4$O$_5$, m/z 597.1672 (MH$^+$), Found m/z: 597.1691 (MH$^+$).

Comparative Example 1

Synthesis of N^α-(2,6-dichlorobenzoyl)-4-{6-(N-formyl-N-methyl-aminomethyl)-quinazoline-2,4[1H,3H]-dion-3-yl}-L-phenylalanine isopropyl ester (Reaction using a substituted anthranilic acid ester)

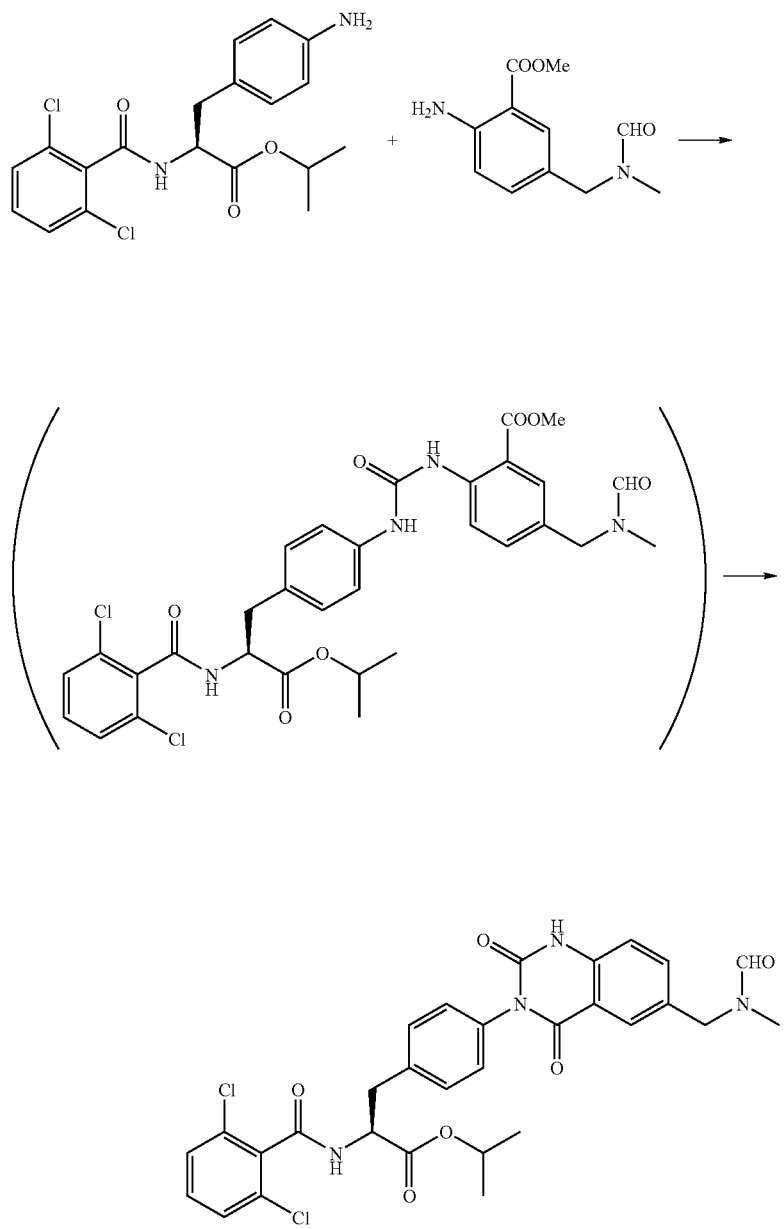

To 3.6 mL of N,N-dimethylformamide, there was added 0.79 g of N,N'-carbonyl-diimidazole (CDI) in a nitrogen gas stream to form a slurry and the latter was cooled to 5° C. To this dissolved liquid, there was added 1.8 g of N^α-(2,6-dichlorobenzoyl)-4-amino-L-phenylalanine isopropyl ester in two portions while taking care to prevent any excess generation of heat. Then the resulting mixture was stirred at 10° C. for one hour, 1.01 g of methyl 2-amino-5-(N-formyl-N-methyl-aminomethyl)-benzoate was added thereto and the mixture was stirred at 60° C. for 6 hours. After confirming the disappearance of the starting material by HPLC, the reaction liquid was cooled to 50° C., 14.4 mL of 2-propanol was added thereto, seed crystals were also added thereto to thus precipitate the desired product. To this slurry, there was dropwise added 18 mL of 2-propanol, the mixture was cooled to 10° C. and stirred overnight.

The solid thus formed was isolated by filtration under reduced pressure, washed with 3.6 mL of 2-propanol, and then dried at 60° C. under reduced pressure to thus give 1.52 g (yield: 55%) of the title compound as a white crystalline solid. The physical properties of the resulting compound were found to be in good agreement with those observed for the compound prepared in the step 1 of Example 5.

Example 6

Synthesis of N^α-(2,6-dichlorobenzoyl)-4-{6-(N-formyl-N-methylamino-methyl)-quinazoline-2,4[1H,3H]-dion-3-yl}-L-phenylalanine isopropyl ester

Step 1: Synthesis of 2-(3-{4-[2(S)-2-(2,6-dichlorobenzoylamino)-2-isopropoxy-carbonyl-ethyl]phenyl}ureido)-5-(N-formyl-N-methylamino-methyl)-benzoic acid

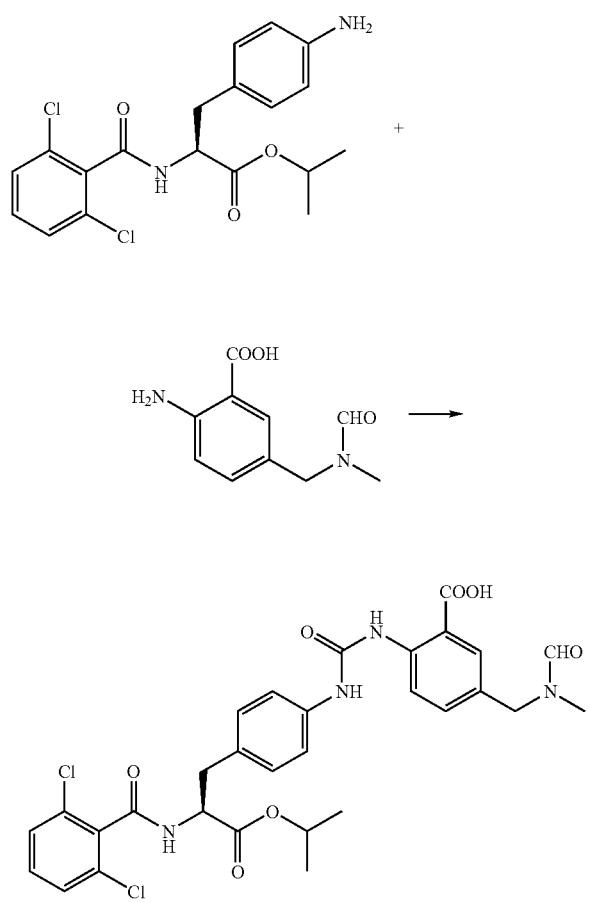

There was suspended, in 3.8 mL of N,N-dimethylformamide, 0.86 g of 1,1'-carbonyl-diimidazole (CDI) and the resulting slurry was cooled to 10° C. There was introduced, into this slurry, 1.90 g of 4-amino-N^α-(2,6-dichlorobenzoyl)-L-phenyl-alanine isopropyl ester, the resulting mixture was stirred at 10° C. for one hour, 1.0 g of 2-amino-5-(N-formyl-N-methyl-aminomethyl)benzoic acid was added to the mixture, followed by stirring at 60° C. for 2 hours. Thereafter, there were added, to the mixture, 7.6 mL of water, 1.0 mL of a 6M aqueous solution of hydrochloric acid and 1.0 mL of a 6M aqueous solution of sodium hydroxide at room temperature. This solution was gradually dropwise added to another egg plant-shaped flask filled with 3.8 mL of water and 1.1 mL of a 6M aqueous solution of hydrochloric acid to thus separate out solid matter and the solid thus formed was separate by suction filtration. After the solid was washed with 10 mL of water, it was dried under reduced pressure at 70° C. for 2 hours to thus give 3.02 g of the title compound as a white crystalline solid.

$^1$H-NMR (400 MHz, DMSO-$d_6$): δ 10.41 and 10.37 (two s, 1H), 9.76 and 9.74 (two s, 1H), 9.17 (d, 1H, J=7.9 Hz), 8.46-8.31 (m, 1H), 8.31 and 8.14 (two s, 1H), 7.84 and 7.82 (two d, 1H, J=2.1 Hz), 7.48-7.37 (m, 6H), 7.19 (d, 2H, J=8.6 Hz), 4.92 (septet, 1H, J=6.2 Hz), 4.69-4.61 (m, 1H), 4.43 and 4.41 (two s, 2H), 3.04 (dd, 1H, J=5.7 and 14.2 Hz), 2.90 (dd, 1H, J=9.2, 14.0 Hz), 2.83 and 2.63 (two s, 3H), 1.21 (d, 3H, J=6.2 Hz), 1.15 (d, 3H, J=6.2 Hz); MS (ESI-): m/z 629.2 (M−H$^-$).

Step 2: Synthesis of N^α-(2,6-dichlorobenzoyl)-4-{6-(N-formyl-N-methylamino-methyl)-quinazoline-2,4[1H,3H]-dion-3-yl}-L-phenylalanine isopropyl ester

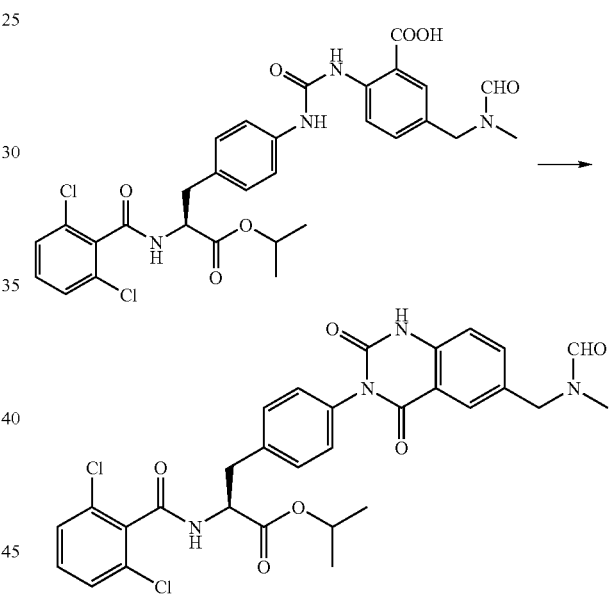

There was added 0.63 mL of N,N-dimethylformamide to 500 mg of 2-(3-{4-[2(S)-2-(2,6-dichlorobenzoylamino)-2-isopropoxy-carbonylethyl]phenyl} ureido)-5-(N-formyl-N-methylamino-methyl)benzoic acid to give a uniform solution, then 287 mg of 1,1'-carbonyl-diimidazole (CDI) was added to the solution, the resulting mixture was heated to 60° C. and stirred for 3 hours. After the reaction solution was cooled to 50° C., 3.15 mL of 2-propanol was added and then seed crystals were added thereto to thus separate out solid. Moreover, 2.52 mL of 2-propanol was dropwise added to the slurry, followed by the cooling of the same to 10° C. and the stirring thereof overnight. The solid thus separated out was removed through filtration under reduced pressure, the resulting cake was washed with 2 mL of 2-propanol and then dried at 70° C. under reduced pressure to thus give 375 mg of the desired product as a white solid. The physical properties of the resulting compound were found to be in good agreement with those observed for the compound prepared in the step 1 of Example 5.

Example 7

Synthesis of 2-amino-5-(N-formyl-N-methylamino-methyl)benzoic acid methyl ester

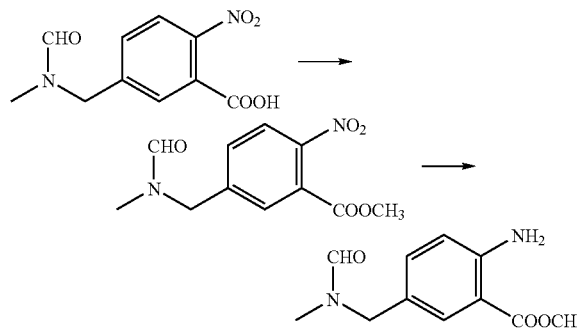

Step 1: Synthesis of 5-(N-formyl-N-methylamino-methyl)-2-nitrobenzoic acid methyl ester There was dissolved, in 6.8 mL of N,N-dimethylformamide, 3.40 g of 5-(N-formyl-N-methylamino-methyl)-2-nitrobenzoic acid, thereafter 3.94 g of potassium carbonate and 1.77 mL of methyl iodide were added to the solution and then the solution was stirred at a temperature ranging from 20 to 30° C. for 4 hours. After the confirmation of the disappearance of the starting material by HPLC, 20.5 mL of water and 34 mL of ethyl acetate were added to the reaction solution. The organic phase was separated from the aqueous phase, followed by the concentration thereof to give 4.47 g of the intended compound as a crude product (oily state).

$^1$H-NMR (400 MHz, DMSO-$d_6$): δ 8.31 and 8.19 (two s, 1H), 8.11 and 8.08 (two d, 1H, J=8.2 Hz), 7.78-7.61 (m, 2H), 4.63 and 4.58 (two s, 2H), 3.86 and 3.85 (two s, 3H), 2.89 and 2.65 (two s, 3H).

Step 2: Synthesis of 2-amino-5-(N-formyl-N-methylamino-methyl)benzoic acid methyl ester There was dissolved, in 34 mL of methanol, 4.47 g of the crude product of 5-(N-formyl-N-methylamino-methyl)-2-nitrobenzoic acid methyl ester, prepare in the step 1, 5% Pd/C (wet product) was added to the solution in an argon gas atmosphere and then hydrogen gas was introduced into the reaction container. The reaction system was stirred at a reaction temperature of 40° C. for 8 hours, the hydrogen gas was replaced with argon gas, 14 mL of methanol was then added to the reaction system and the temperature thereof was raised up to 55° C. The Pd/C catalyst was removed through filtration under reduced pressure, the catalyst was washed with 25 mL of methanol and the resulting filtrate and the wash liquid were maintained at a temperature of 40° C. Water (31 mL) was dropwise added thereto thus separate out solid and the resulting slurry was stirred at 10° C. overnight. The resulting solid was separated from the slurry through filtration under reduced pressure, washed with 7 mL of water and then dried under reduced pressure at 70° C. for 5 hours to give 2.53 g of the title compound as a white solid.

$^1$H-NMR (400 MHz, DMSO-$d_6$): δ 8.26 and 8.10 (two s, 1H), 7.62 and 7.60 (two d, 1H, J=2.2 Hz), 7.17 and 7.14 (two dd, 1H, J=2.2, 8.6 Hz), 6.80 and 6.77 (two d, 1H, J=8.6 Hz), 6.71 and 6.67 (two bs, 2H), 4.28 (s, 2H), 3.80 and 3.79 (two s, 3H), 2.78 and 2.59 (two s, 3H); MS (ESI+): m/z 223.3 (MH$^+$), 245.2 (M+Na).

Example 8

Synthesis of 2-amino-5-(N-tert-butoxycarbonyl-N-methylamino-methyl)benzoic acid methyl ester

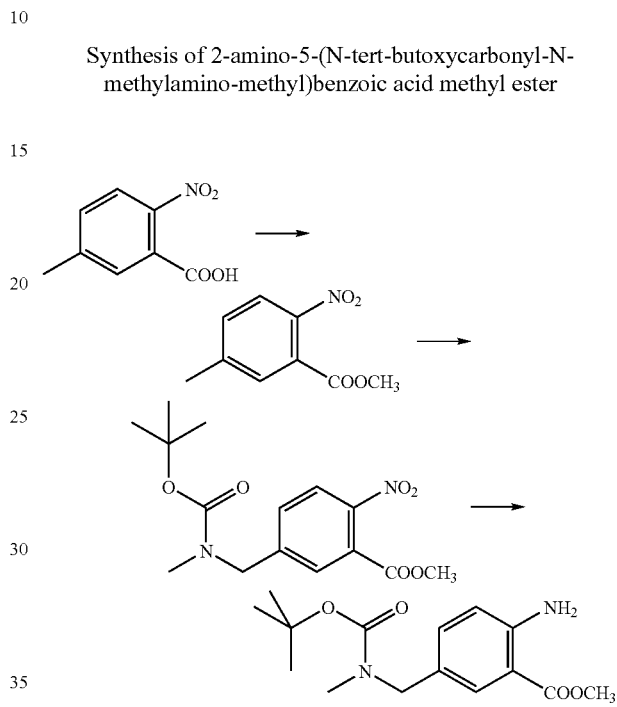

Step 1: Synthesis of 5-methyl-2-nitrobenzoic acid methyl ester

There was dissolved, in 200 mL of N,N-dimethylformamide, 20.0 g of 5-methyl-2-nitrobenzoic acid, 22.9 g of potassium carbonate and then 8.2 mL of methyl iodide were added to the resulting solution and the mixture was stirred at room temperature for 4 hours. To the reaction liquid, there were added 400 mL of water and 200 mL of a 1M hydrochloric acid solution, then extracted with 900 mL of ethyl acetate, the extract was washed with 200 mL of a saturated sodium hydrogen carbonate solution and 200 mL of a saturated common salt solution and the solvent was then distilled off under reduced pressure to thus give 20.6 g of the title compound as a crude product.

MS (ESI+): m/z 196 (MH$^+$).

Step 2: Synthesis of 5-(N-tert-butoxycarbonyl-N-methylamino-methyl)-2-nitrobenzoic acid methyl ester To 1.0 g of the crude product of 5-methyl-2-nitrobenzoic acid methyl ester synthesized in the foregoing step 1, there were added 1.4 g of N-bromosuccinimide, 0.5 g of benzoyl peroxide and 30 mL of benzene, the resulting mixture was refluxed with stirring for 4 hours and the solvent was distilled off under reduced pressure. The resulting residue was dissolved in 30 mL of acetonitrile, this solution was added to 36 mL of a 2M methylamine solution in THF and the mixture was further stirred at room temperature for 10 minutes. The solvent was distilled off under reduced pressure, then ethyl acetate was added, followed by the washing thereof four times with a 1M hydrochloric acid solution. The resulting ethyl acetate phase was washed with a saturated sodium hydrogen carbonate aqueous solution and a saturated common salt solution and the solvent was distilled off under reduced pressure. The crude product thus prepared was dissolved in 30 mL of acetonitrile, 1.1 g of di-tert-butyl-dicarbonate and 1.1 mL of triethylamine were added to the solution and the resulting mixture was stirred at room temperature overnight. The solvent was distilled off under reduced pressure, ethyl acetate was added thereto, the insoluble matter was then removed through filtration and the filtrate thus obtained was concentrated under reduced pressure. The resulting crude product was purified by the silica gel chromatography (hexane:ethyl acetate=90:10→80:20) to thus give 0.71 g of the title compound. MS (ESI+): m/z 325 (MH$^+$).

Step 3: Synthesis of 2-amino-5-(N-tert-butoxycarbonyl-N-methyl-aminomethyl)benzoic acid methyl ester There was dissolved, in 50 mL of methanol, 2.5 g of 5-(N-tert-butoxy-carbonyl-N-methylamino-methyl)-2-nitrobenzoic acid methyl ester prepared in the foregoing step 2, 230 mg of 10% Pd/C was added to the solution and the resulting mixture was stirred at room temperature for 3 hours in a hydrogen gas atmosphere. The reaction liquid was filtered through Celite, washed with methanol and then the solvent was distilled off under reduced pressure to thus give 2.26 g of the title compound.

MS (ESI+): m/z 295 (MH$^+$).

Example 9

Synthesis of N$^\alpha$-(2,6-dichlorobenzoyl)-4-isocyanate-L-phenylalanine methyl ester Step 1: Synthesis of N$^\alpha$-(2,6-dichlorobenzoyl)-4-iodo-L-phenylalanine

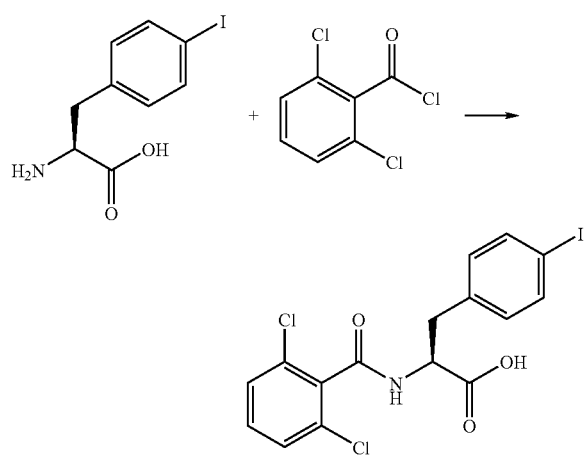

Water (21 mL), acetone (9.80 mL) and a 6M sodium hydroxide aqueous solution (5.20 mL) were added to 7.50 g of 4-iodo-L-phenylalanine and the resulting mixture was stirred at 10° C. to thus give a uniform solution. To this solution, there were alternatively added 4.05 mL of 2,6-dichlorobenzoyl chloride and 4.50 mL of a 6M sodium hydroxide aqueous solution while taking care to maintain the pH value of not less than 13 and the temperature of not higher than 15° C. After confirming the completion of the reaction, 6.50 mL of a 6M hydrochloric acid aqueous solution was added to the reaction system to thus precipitate the desired product. The solid thus separated was isolated through filtration under reduced pressure, washed with 15 mL of water and dried at 70° C. for 4 hours under reduced pressure to thus give 12.42 g of the intended product.

$^1$H-NMR (400 MHz, DMSO-d$_6$): δ 9.06 (d, 1H, J=8.3 Hz), δ 7.63 (d, 2H, J=8.2 Hz), δ 7.48-7.35 (m, 3H), δ 7.11 (d, 2H, J=8.2 Hz), δ 4.68 (ddd, 1H, J=10.0, 8.4, 4.8 Hz), δ 3.11 (dd, 1H, J=14.0, 4.8 Hz), δ 2.87 (dd, 1H, J=14.0, 10.0 Hz); MS (ESI+): m/z 463.9 (MH$^+$) and 485.9 (M+Na), (ESI−): m/z 461.8 (M−H$^-$).

Step 2: Synthesis of N$^\alpha$-(2,6-dichlorobenzoyl)-4-iodo-L-phenylalanine methyl ester

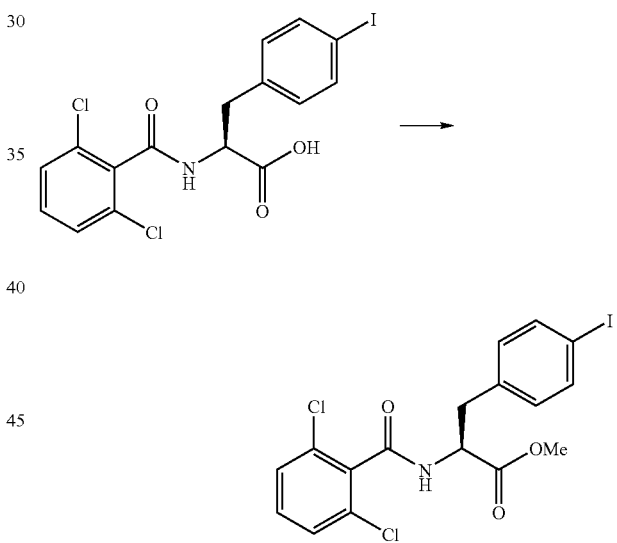

Methanol (40 mL) and 0.98 mL of concentrated sulfuric acid were added to 8.0 g of N$^\alpha$-(2,6-dichlorobenzoyl)-4-iodo-L-phenylalanine and the reaction was carried out for 4 hours while heating the reaction system at 40° C. After confirming the completion of the reaction, the reaction system was cooled to 10° C. and 20 mL of water was dropwise added to separate out solid. The solid thus precipitated was isolated through filtration under reduced pressure, washed with 40 mL of water and then dried at 70° C. under reduced pressure to thus give 7.40 g of the desired product as a solid.

$^1$H-NMR (400 MHz, DMSO-d$_6$): δ 9.18 (d, 1H, J=8.1 Hz), 7.64 (d, 2H, J=8.1 Hz), 7.48-7.35 (m, 3H), 7.11 (d, 2H, J=8.2 Hz), 4.75 (ddd, 1H, J=10.0, 8.1, 4.9 Hz), 3.67 (s, 3H), 3.11 (dd, 1H, J=14.1, 5.1 Hz), 2.90 (dd, 1H, J=14.0, 10.2 Hz); MS (ESI+): m/z 478.0 (MH$^+$), (ESI−): m/z 475.9 (M−H$^-$).

Step 3: Synthesis of 4-carboxyl-N^α-(2,6-dichlorobenzoyl)-L-phenylalanine methyl ester

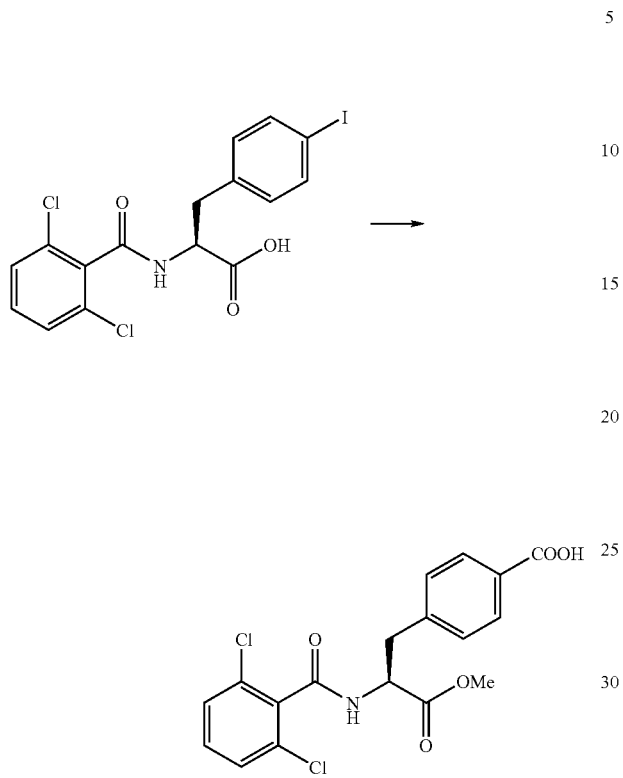

There were blended 0.5 mL of DMF, 122 mg of sodium formate, 206 μl of diisopropyl ethylamine and 113 μl of acetic anhydride in a test tube provided with a screw cap and the mixture was stirred at room temperature for 10 minutes. Then there were added, to the resulting mixture, 288 mg of N^α-(2,6-dichlorobenzoyl)-4-iodo-L-phenylalanine methyl ester, 32 mg of 10% Pd/C, 76 mg of lithium chloride and 0.4 mL of DMF, the resulting mixture was further stirred while raising the temperature up to 80° C., there were further added, to the mixture, 41 mg of sodium formate and 57 μl of acetic anhydride, followed by additional stirring. After confirming the completion of the reaction, the Pd/C was removed through filtration and washed with 0.6 mL of a 6M hydrochloric acid solution, 0.3 mL of water and 1.3 mL of DMF. Water (3.5 mL) was dropwise added to the reaction liquid at room temperature, seed crystals were further added to the reaction liquid to thus separate out solid and the resulting suspension was cooled to 10° C. The resulting precipitates were isolated through filtration under reduced pressure, washed with 3 mL of water and then dried at 60° C. under reduced pressure to thus give 217 mg of a roughly purified product as a solid. Subsequently, the crude product was recrystallized from acetonitrile to thus give 71 mg of the purified desired product.

$^1$H-NMR (400 MHz, DMSO-$d_6$): δ 9.22 (d, 1H, J=8.1 Hz), 7.86 (d, 2H, J=8.4 Hz), 7.48-7.35 (m, 5H), 4.81 (ddd, 1H, J=10.2, 8.3, 5.1 Hz), 3.67 (s, 3H), 3.23 (dd, 1H, J=14.0, 4.9 Hz), 3.02 (dd, 1H, J=14.0, 10.2 Hz); MS (ESI+): m/z 396.1 (MH$^+$), 418.1 (M+Na); MS (ESI−): m/z 394.1 (M−H$^-$).

Step 4: Synthesis of N^α-(2,6-dichlorobenzoyl)-4-isocyanate-L-phenylalanine methyl ester

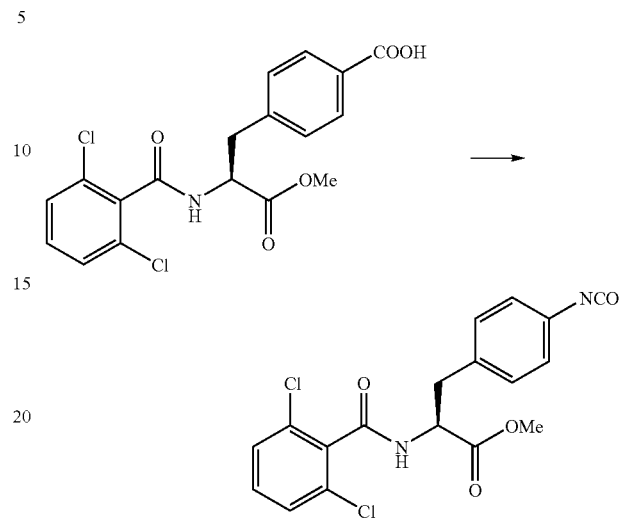

There were added 2 mL of 1,2-dimethoxy-ethane (dehydrated), 54 μl of triethylamine and 55 μl of diphenyl-phosphoryl azide (DPPA) to 100 mg of 4-carboxyl-N^α-(2,6-dichlorobenzoyl)-L-phenylalanine methyl ester and the resulting mixture was stirred at room temperature for one hour. Then the temperature of the mixture was raised to a level ranging from 80 to 90° C., stirred for 3 hours and then the solvent was removed through distillation under reduced pressure. The oily crude product thus obtained was purified by silica gel flash column chromatography (diethyl ether/n-hexane=1/1→pure diethyl ether) and the solvent was distilled off under reduced pressure to thus give the desired product.

$^1$H-NMR (400 MHz, CDCl$_3$): δ 7.35-7.23 (m, 3H), 7.20-7.15 (m, 2H), 7.04-6.98 (m, 2H), 6.31 (bd, 1H, J=7.3 Hz), 5.16 (dt, 1H, J=8.0, 5.8 Hz), 3.76 (s, 3H), 3.27 (dd, 1H, J=14.2, 5.7 Hz), 3.23 (dd, 1H, J=14.2, 5.7 Hz); MS (ESI+): m/z 393.0, 415.0 (M+Na); MS (ESI−): m/z 391.1 (M−H$^-$); IR (KBr), cm$^{-1}$: 2268.1 (s), 1743.5 (m), 1654.8 (m), 1581.5 (m), 1539.1 (m), 1519.8 (m).

Example 10

Synthesis of N^α-(2,6-dichlorobenzoyl)-4-{6-dimethylamino-quinazoline-2,4[1H,3H]-dion-3-yl}-L-phenylalanine methyl ester

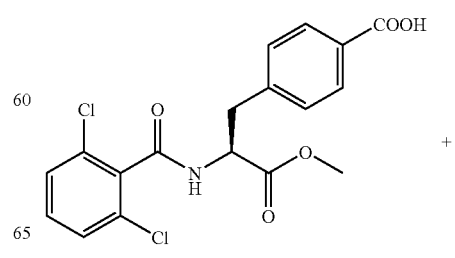 +

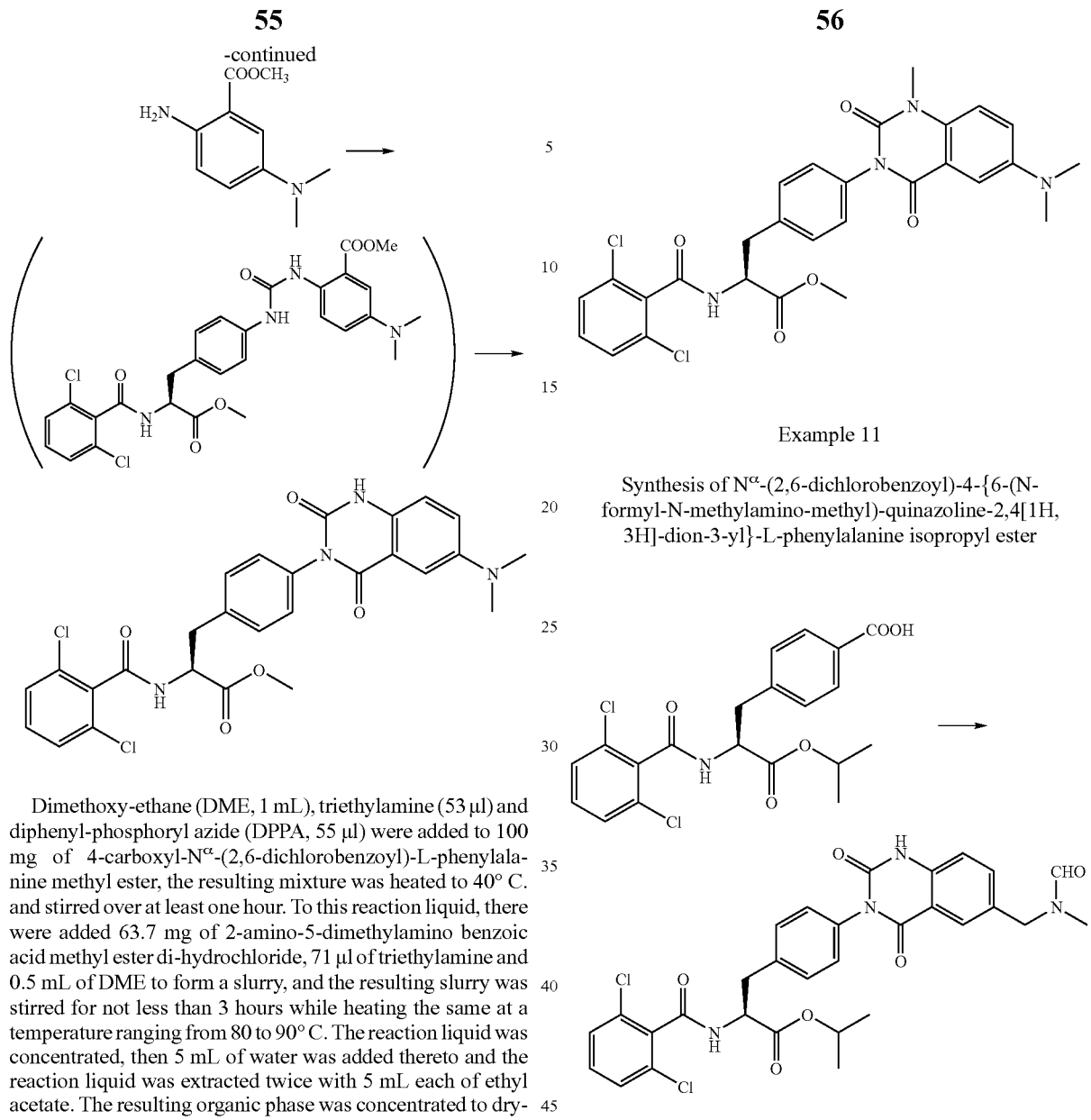

Dimethoxy-ethane (DME, 1 mL), triethylamine (53 µl) and diphenyl-phosphoryl azide (DPPA, 55 µl) were added to 100 mg of 4-carboxyl-$N^\alpha$-(2,6-dichlorobenzoyl)-L-phenylalanine methyl ester, the resulting mixture was heated to 40° C. and stirred over at least one hour. To this reaction liquid, there were added 63.7 mg of 2-amino-5-dimethylamino benzoic acid methyl ester di-hydrochloride, 71 µl of triethylamine and 0.5 mL of DME to form a slurry, and the resulting slurry was stirred for not less than 3 hours while heating the same at a temperature ranging from 80 to 90° C. The reaction liquid was concentrated, then 5 mL of water was added thereto and the reaction liquid was extracted twice with 5 mL each of ethyl acetate. The resulting organic phase was concentrated to dryness, 0.4 mL of N,N-dimethylformamide to give a uniform dispersion, 2 mL of methanol was then added to the dispersion to thus separate solid and the mixture was stirred at 10° C. overnight. The separated solid was recovered through filtration under reduced pressure, washed with 5 mL of methanol and then dried under reduced pressure at 70° C. for 6 hours to thus give 75 mg of the desired compound as a pale yellow solid.

$^1$H-NMR (400 MHz, DMSO-$d_6$): δ 11.22 (s, 1H), 9.28 (d, 1H, J=8.1 Hz), 7.48-7.35 (m, 5H), 7.27 (dd, 1H, J=9.0, 2.8 Hz), 7.21-7.09 (m, 4H), 4.80 (ddd, 1H, J=10.0, 8.1, 4.9 Hz), 3.69 (s, 3H), 3.22 (dd, 1H, J=4.6, 14.2 Hz), 3.02 (dd, 1H, J=10.2, 13.8 Hz), 2.91 (s, 6H); $^{13}$C-NMR (400 MHz, DMSO-$d_6$): δ 171.70, 163.99, 162.75, 150.18, 146.83, 137.15, 136.34, 134.80, 131.78, 131.36, 131.15, 129.84, 129.18, 128.32, 122.05, 116.48, 115.03, 108.50, 53.70, 52.29, 40.93, 36.36; MS (ESI+): m/z 555.1 (MH$^+$) and 577.2 (M+Na); MS (ESI−): m/z 553.2 (M−H$^−$).

In this connection, the compound prepared herein can be subjected to N-methylation according to the method disclosed in Patent Document 2 (WO 2004/74264) to thus derive a compound represented by the following structural formula:

Example 11

Synthesis of $N^\alpha$-(2,6-dichlorobenzoyl)-4-{6-(N-formyl-N-methylamino-methyl)-quinazoline-2,4[1H, 3H]-dion-3-yl}-L-phenylalanine isopropyl ester Acetonitrile (80 mL), triethylamine (4.93 mL) and diphenyl-phosphoryl azide (DPPA, 1.52 mL) were added to 3.0 g of 4-carboxyl-$N^\alpha$-(2,6-dichlorobenzoyl)-L-phenyl-alanine isopropyl ester and the resulting mixture was stirred for one hour while heating it to 60° C. There was added, to this reaction liquid, 1.47 g of 2-amino-5-(N-formyl-N-methylamino-methyl)benzoic acid and then the mixture was stirred for not less than 12 hours while heating the same at 90° C. Subsequently, 2.29 g of 1,1'-carbonyl-diimidazole (CDI) was added to the mixture, followed by the stirring of the same for not less than 1.5 hours. After the completion of the reaction, the reaction liquid was concentrated, followed by the addition of 500 mL of ethyl acetate and 500 mL of a 1M hydrochloric acid solution and the separation through extraction. The organic phase thus obtained was in order washed with a mixed liquid containing 500 mL of water and 100 mL of a saturated sodium bicarbonate solution, 300 mL of a saturated sodium bicarbonate solution, and then 300 mL of a saturated sodium chloride aqueous solution, and then dried over anhydrous sodium sulfate. Thereafter, the organic phase was concentrated to dryness, the resulting slurry was washed with diethyl ether, the solid obtained was isolated through filtration under reduced pressure and then washed with diethyl ether. Then the solid was dried under reduced pressure to thus obtain 3.25 g of the intended product as a white solid. The physical properties of the resulting compound were found to be in good agreement with those observed for the same compound prepared in the foregoing synthesis Example.

Example 12

Synthesis of N$^\alpha$-(2,6-dichlorobenzoyl)-4-{6-(N-tert-butoxy-carbonyl-N-methylamino-methyl)-quinazoline-2,4[1H,3H]-dion-3-yl}-L-phenylalanine isopropyl ester

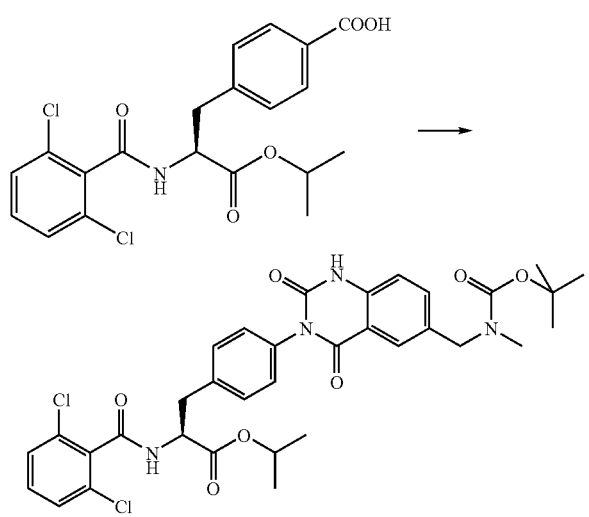

There were added, to 250 mg of N$^\alpha$-(2,6-dichlorobenzoyl)-4-carboxyl-L-phenyl-alanine isopropyl ester, 20 mL of acetonitrile, 411 μl of triethylamine and 127 μl of diphenyl-phosphoryl azide (DPPA), and the resulting mixture was stirred for one hour while heating the same to 60° C. To the reaction liquid, there was added 165 mg of 2-amino-5-(N-tert-butoxy-carbonyl-N-methylamino-methyl)benzoic acid and then the mixture was stirred for 2 hours, while heating the same to 90° C. Then 96 mg of 1,1'-carbonyl-diimidazole (CDI) was added, followed by the stirring of the same overnight. After the completion of the reaction, the reaction liquid was subjected to isolation and purification according to the reversed phase column chromatography to thus obtain 229 mg of the intended product as a solid. MS (ESI): m/z 683 (MH$^+$).

Example 13

Synthesis of 5-(N-formyl-N-methylamino-methyl) isatoic anhydride

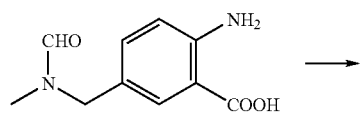

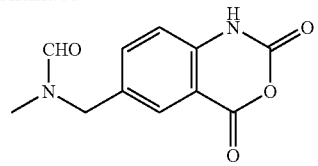

There was suspended, in 15.2 mL of N,N-dimethylformamide, 3.82 g of 1,1'-carbonyl-diimidazole (CDI) and the resulting suspension was cooled to 5° C. To this slurry, there was added 4.0 g of 2-amino-5-(N-formyl-N-methylamino-methyl)benzoic acid in two portions, followed by the stirring of the same for one hour. After the confirmation of the disappearance of the starting material by HPLC, seed crystals were added to the slurry while dropwise adding 40.3 mL of a 1M hydrochloric acid aqueous solution to separate out solid and the resulting solid was isolated through filtration under reduced pressure. After washing the solid with 120 mL of water, it was dried at 70° C. for 13 hours under reduced pressure to thus give 3.20 g of the title compound as a white solid.

$^1$H-NMR (400 MHz, DMSO-d$_6$): δ 11.82 (bs, 1H), 8.32 and 8.15 (two s, 1H), 7.84 and 7.78 (two d, 1H, J=1.7 Hz), 7.65 and 7.60 (two dd, 1H, J=2.0, 8.4 Hz), 7.17 and 7.15 (two d, 1H, J=8.4 Hz), 4.49 and 4.47 (two s, 2H), 2.84 and 2.62 (two s, 3H); MS (ESI+): m/z 235 (MH$^+$), (ESI−): m/z 233.1 (M−H$^-$).

Example 14

Synthesis of 5-dimethylamino isatoic anhydride

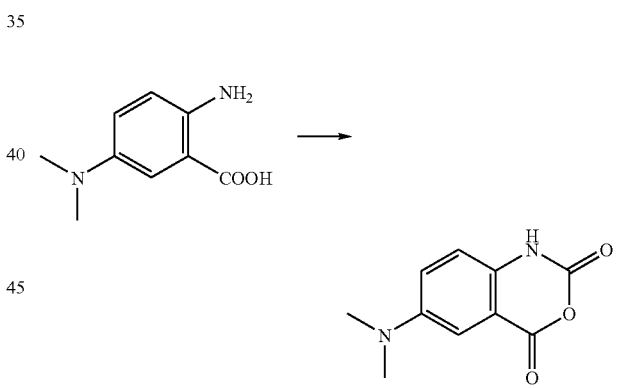

There was suspended, in 0.76 mL of N,N-dimethylformamide, 144 mg of 1,1'-carbonyl-diimidazole (CDI) and the resulting suspension was cooled to 5° C. To this slurry, there was added 200 mg of 2-amino-5-dimethylamino-benzoic acid hydrochloride, followed by the stirring of the same for one hour or longer, the further addition of 0.76 mL of N,N-dimethylformamide and 66 mg of 1,1'-carbonyl-diimidazole (CDI) and the stirring thereof for additional one hour. The solid separated from the suspension was isolated through filtration under reduced pressure, washed with 2 mL of methanol and then dried at 60° C. under reduced pressure to thus give 91 mg of the desired product as a yellow solid.

$^1$H-NMR (400 MHz, DMSO-d$_6$): δ 11.42 (bs, 1H), δ 7.28 (dd, 1H, J=9.1, 3.0 Hz), 7.05 (d, 1H, J=8.7 Hz), 7.04 (d, 1H, J=3.2 Hz), 2.91 (s, 6H); MS (ESI+): m/z 207.2 (M+H$^+$) and 248.2 (M+MeCN) and 270.2 (M+MeCN+Na); (ESI−): m/z 205.1 (M−H$^-$)

Example 15

Synthesis of N$^\alpha$-(2,6-dichlorobenzoyl)-4-{6-(N-formyl-N-methylamino-methyl)-quinazoline-2,4[1H,3H]-dion-3-yl}-L-phenylalanine isopropyl ester (Method 1: Continuous method carried out without isolating an amide intermediate)

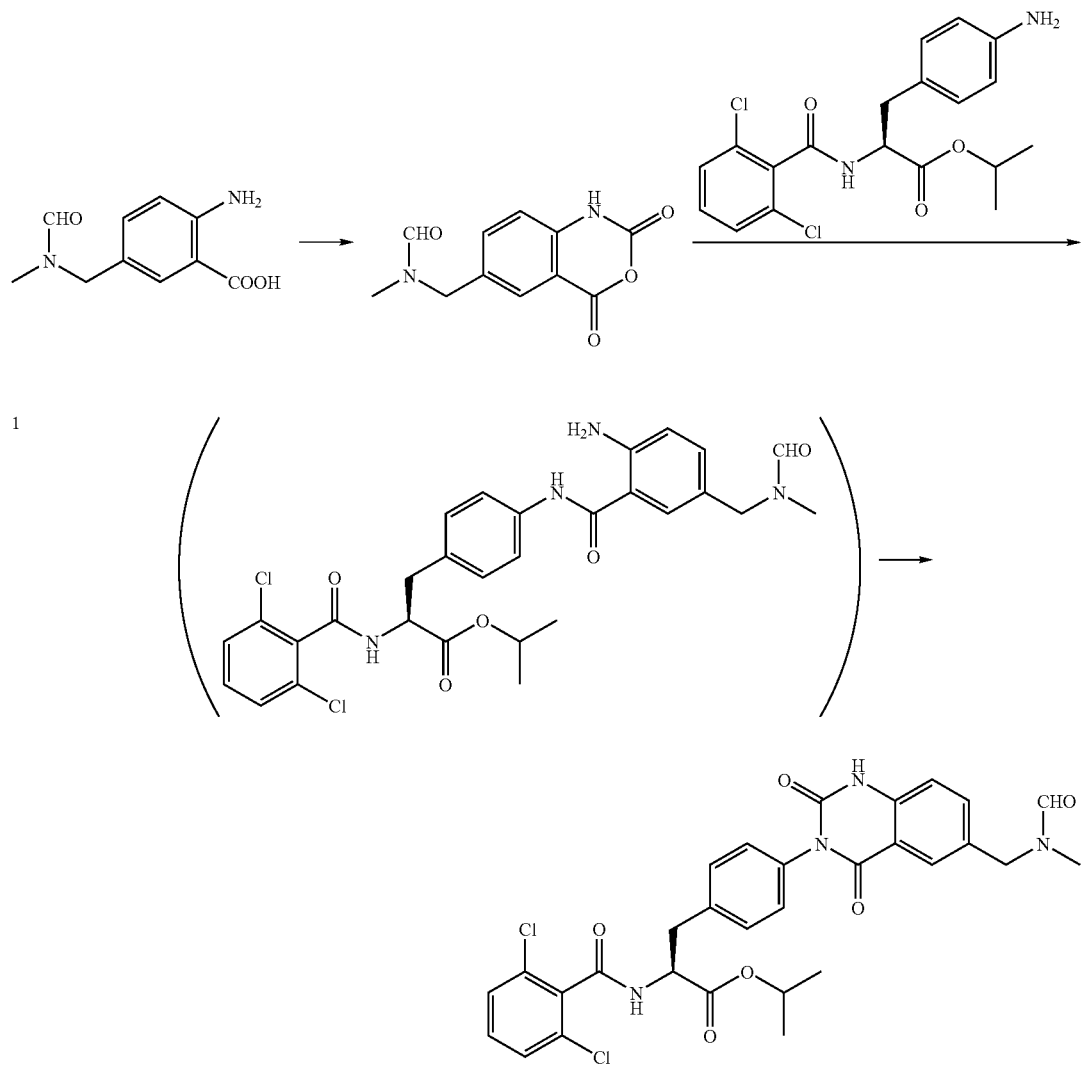

There was suspended, in 7.6 mL of N,N-dimethylformamide, 1.64 g of 1,1'-carbonyl-diimidazole (CDI) and the suspension was cooled to 10° C. To this suspension, there was added 2.0 g of 2-amino-5-(N-formyl-N-methylamino-methyl)benzoic acid and the mixture was stirred at 10° C. After the confirmation of the formation of isatoic anhydride by HPLC, 3.80 g of 4-amino-N$^\alpha$-(2,6-dichlorobenzoyl)-L-phenylalanine isopropyl ester to thus carry out amidation at 60° C. After the confirmation of the completion of the reaction by HPLC, the reaction system was cooled to 25° C., 1.96 g of 1,1'-carbonyl-diimidazole (CDI) was added thereto and the mixture was again heated to 60° C. After the elapse of 2 hours and the confirmation of the completion of the reaction by HPLC, the reaction system was cooled to a temperature ranging from 50 to 40° C., seed crystals were added thereto while dropwise adding 30.4 mL of 2-propanol to thus precipitate the intended product. Further, additional 38.0 mL of 2-propanol was dropwise added to the reaction system, the resulting mixture was stirred at 9° C. overnight, the solid separated out was isolated through filtration under reduced pressure and washed with 11.4 mL of 2-propanol.

Thereafter, the solid was dried at 60° C. for 3 hours to thus give 3.51 g of the title compound as a white crystalline solid. The physical properties of the resulting compound were found to be in good agreement with those observed for the same compound prepared in the foregoing synthesis Example.

In this respect, the amide intermediate which is not isolated in this step can likewise be isolated according to a method separately disclosed in another Example.

Example 16

Synthesis of N^α-(2,6-dichlorobenzoyl)-4-{6-dimethylamino-quinazoline-2,4[1H,3H]-dion-3-yl}-L-phenylalanine methyl ester (Method 1: Continuous method carried out without isolating an amide intermediate)

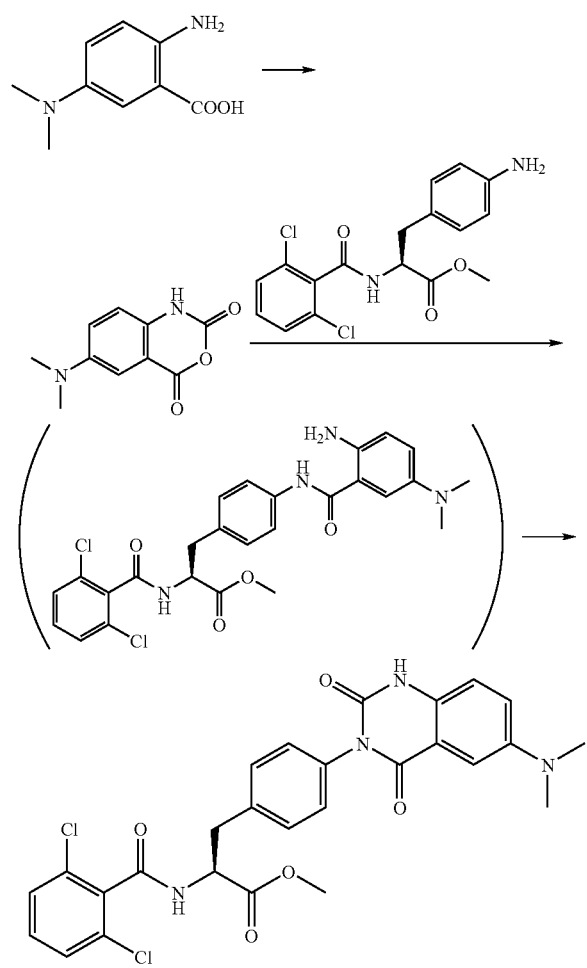

There was suspended, in 32 mL of N,N-dimethylformamide, 1.89 g of 1,1'-carbonyl-diimidazole (CDI) and the suspension was cooled to 10° C. To this slurry, there was added 1.96 g of 2-amino-5-dimethylamino-benzoic acid and it was then stirred at a temperature ranging from 10 to 25° C. for 2 hours. Then 4.00 g of N^α-(2,6-dichlorobenzoyl)-4-amino-L-phenylalanine methyl ester was added to the mixture and the latter was stirred at 60° C. for 2 hours. To this solution, there was added 2.16 g of 1,1'-carbonyl-diimidazole (CDI), the mixture was stirred at 60° C. overnight, and seed crystals were added to the mixture at a temperature ranging from 60 to 10° C., while dropwise adding 160 mL of methanol thereto to thus separate out solid. The resulting slurry was stirred at 10° C. overnight, the solid was isolated through filtration under reduced pressure, washed with 16 mL of methanol and then dried at 70° C. for 5 hours under reduced pressure to thus give 1.84 g of the intended compound as a pale yellow solid. The physical properties of the resulting compound were found to be in good agreement with those observed for the same compound prepared in the foregoing synthesis Example.

Example 17

Synthesis of N^α-(2,6-dichlorobenzoyl)-4-{6-(N-formyl-N-methylamino-methyl)-quinazoline-2,4[1H,3H]-dion-3-yl}-L-phenylalanine isopropyl ester (Method 2 in which an amide intermediate is isolated)

Step 1: Synthesis of 4-{2-amino-5-(N-formyl-N-methylamino-methyl)-benzoylamino}-N^α-(2,6-dichlorobenzoyl)-L-phenylalanine isopropyl ester

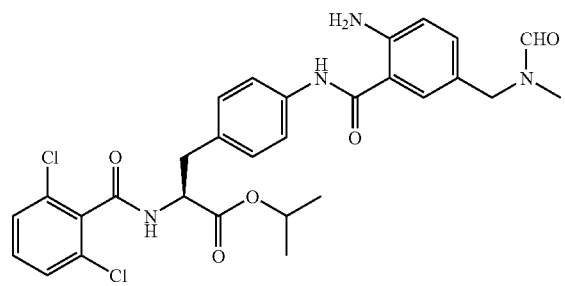

There was suspended, in 7.6 mL of N,N-dimethylformamide, 1.67 g of 1,1'-carbonyl-diimidazole (CDI) and the suspension was cooled to 5° C. To this slurry, there was added 2.0 g of 2-amino-5-(N-formyl-N-methylamino-methyl)-benzoic acid to thus carry out a reaction for forming an isatoic anhydride derivative at 5° C. After the confirmation of the completion of the reaction by HPLC, 3.80 g of 4-amino-N^α-(2,6-dichlorobenzoyl)-L-phenylalanine isopropyl ester was added to the reaction system to thus carry out amidation at 60° C. overnight. After the confirmation of the completion of the reaction by HPLC, the reaction system was cooled to a temperature ranging from 25 to 50° C. followed by the addition of 3 mL of water. This solution was slowly dropwise added to another egg plant-shaped flask to which 29 mL of water had previously been added to thus form a solid material and then the separated solid was isolated through filtration under reduced pressure. After washing the solid with 20 mL of water, it was dried under reduced pressure to thus give 5.50 g of a crude product of the intended compound. To this crude product, there was added 5.5 mL of acetonitrile to obtain a uniform dispersion, 137.5 mL of 2-propanol and seed crystals were added thereto to precipitate a solid material and the slurry was stirred at 20° C. for 2 hours. The solid thus separated was isolated through filtration under reduced pressure, washed with 20 mL of 2-propanol and then dried under reduced pressure to thus give 2.60 g of the intended product as a white crystalline solid.

$^1$H-NMR (400 MHz, DMSO-$d_6$): δ 9.97 and 9.95 (two s, 1H), 9.19 (d, 1H, J=8.0 Hz), 8.27 and 8.10 (two s, 1H), 7.65-7.35 (m, 6H), 7.29-7.22 (m, 2H), 7.14-7.03 (m, 1H), 6.79-6.71 (m, 1H), 6.35 and 6.27 (two bs, 2H), 4.92 (septet, 1H, J=6.2 Hz), 4.72-4.63 (m, 1H), 4.32 and 4.29 (two s, 2H), 3.07 (dd, 1H, J=14.0, 5.7 Hz), 2.94 (dd, 1H, J=14.0, 9.2 Hz), 2.81 and 2.64 (two s, 3H), 1.21 (d, 3H, J=6.4 Hz), 1.16 (d, 3H, J=6.4 Hz); MS (ESI+): m/z 585.0 (MH+), (ESI−): m/z 583.2 (M−H−).

Step 2: Synthesis of N$^\alpha$-(2,6-dichlorobenzoyl)-4-{6-(N-formyl-N-methylamino-methyl)quinazoline-2,4 [1H,3H]-dion-3-yl}-L-phenylalanine isopropyl ester

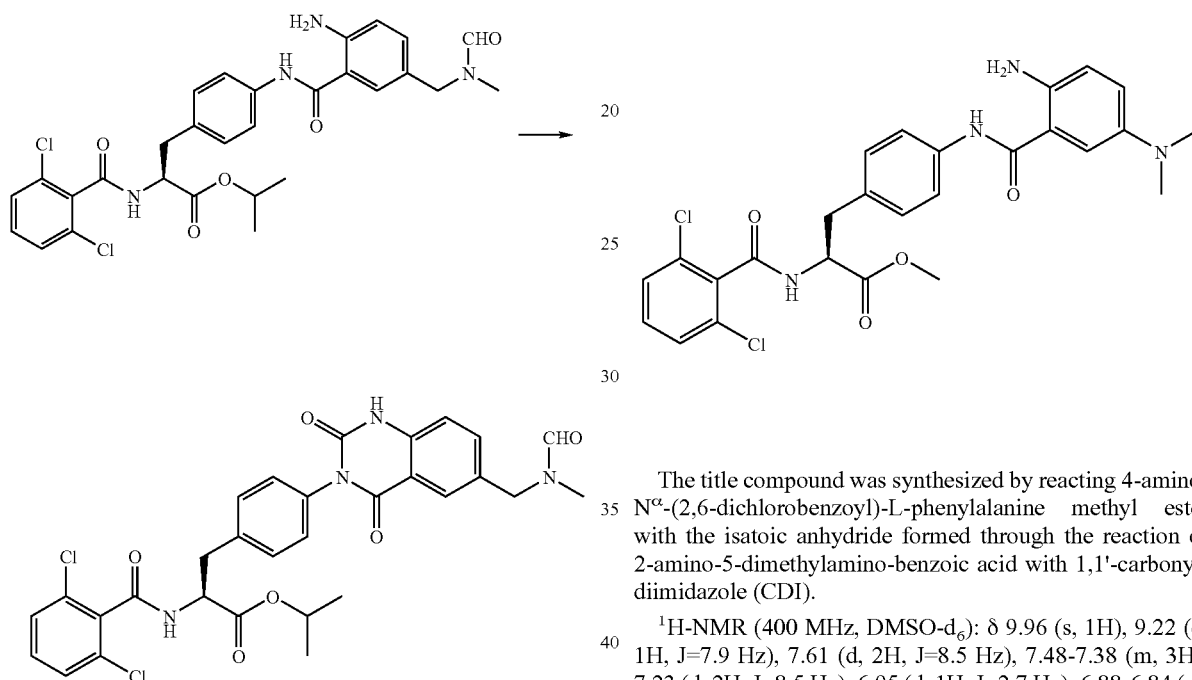

There was added 1.34 mL of N,N-dimethylformamide to 1.0 g of 4-{2-amino-5-(N-formyl-N-methylamino-methyl)-benzoylamino}-N$^\alpha$-(2,6-dichlorobenzoyl)-L-phenyl-alanine isopropyl ester to thus form a uniform dispersion, then 0.34 g of 1,1′-carbonyl-diimidazole (CDI) was added to the dispersion and the resulting mixture was heated at 60° C. with stirring for not less than one hour.

After the mixture was cooled to 50° C., 6.7 mL of 2-propanol was added and seed crystals were added to separate out a solid material. Further, 5.36 mL of 2-propanol was dropwise added to the slurry thus obtained and then cooled to 10° C. with stirring overnight. The separated solid was isolated through filtration under reduced pressure, washed with 2 mL of 2-propanol and then dried under reduced pressure at 70° C. to thus give 0.85 g of the title compound as a white solid. The physical properties of the resulting compound were found to be in good agreement with those observed for the same compound prepared in the foregoing synthesis Example.

Example 18

Synthesis of 4-{2-amino-6-dimethylamino-benzoylamino}-N$^\alpha$-(2,6-dichlorobenzoyl)-L-phenylalanine methyl ester (Method 2 in which an amide intermediate is isolated)

Step 1: Synthesis of 4-{2-amino-5-dimethylamino-benzoylamino}-N$^\alpha$-(2,6-dichloro-benzoyl)-L-phenylalanine methyl ester

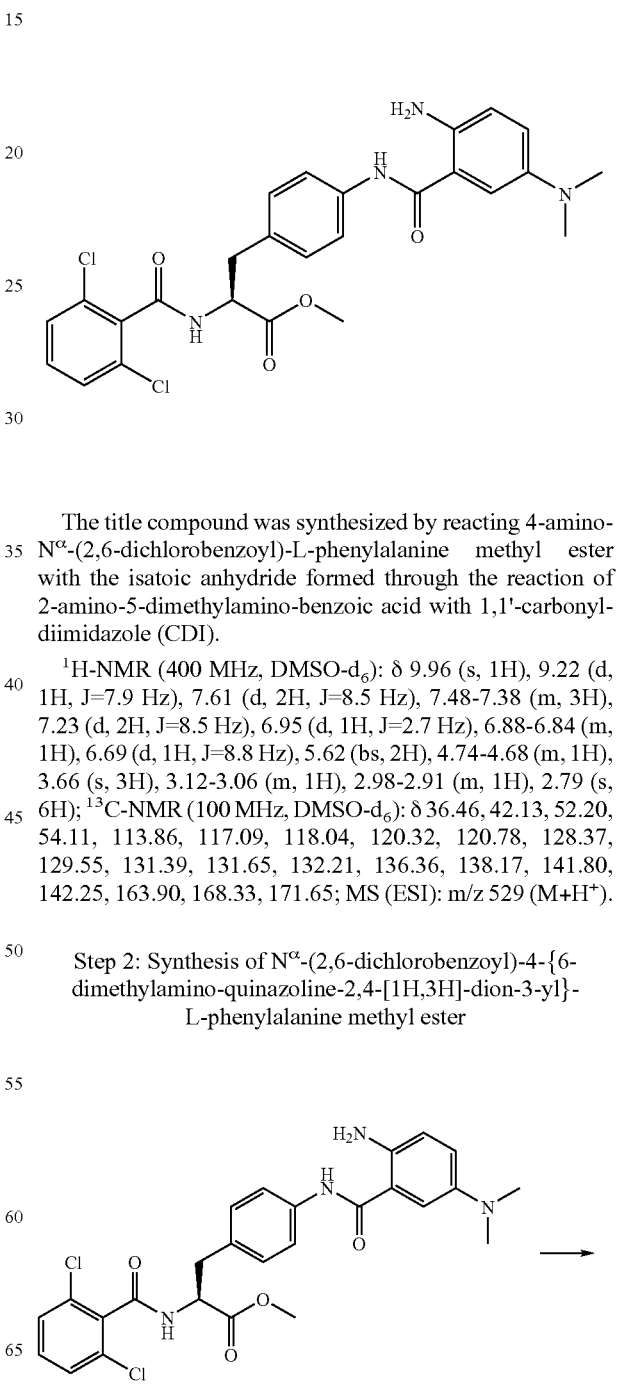

The title compound was synthesized by reacting 4-amino-N$^\alpha$-(2,6-dichlorobenzoyl)-L-phenylalanine methyl ester with the isatoic anhydride formed through the reaction of 2-amino-5-dimethylamino-benzoic acid with 1,1′-carbonyl-diimidazole (CDI).

$^1$H-NMR (400 MHz, DMSO-d$_6$): δ 9.96 (s, 1H), 9.22 (d, 1H, J=7.9 Hz), 7.61 (d, 2H, J=8.5 Hz), 7.48-7.38 (m, 3H), 7.23 (d, 2H, J=8.5 Hz), 6.95 (d, 1H, J=2.7 Hz), 6.88-6.84 (m, 1H), 6.69 (d, 1H, J=8.8 Hz), 5.62 (bs, 2H), 4.74-4.68 (m, 1H), 3.66 (s, 3H), 3.12-3.06 (m, 1H), 2.98-2.91 (m, 1H), 2.79 (s, 6H); $^{13}$C-NMR (100 MHz, DMSO-d$_6$): δ 36.46, 42.13, 52.20, 54.11, 113.86, 117.09, 118.04, 120.32, 120.78, 128.37, 129.55, 131.39, 131.65, 132.21, 136.36, 138.17, 141.80, 142.25, 163.90, 168.33, 171.65; MS (ESI): m/z 529 (M+H+).

Step 2: Synthesis of N$^\alpha$-(2,6-dichlorobenzoyl)-4-{6-dimethylamino-quinazoline-2,4-[1H,3H]-dion-3-yl}-L-phenylalanine methyl ester

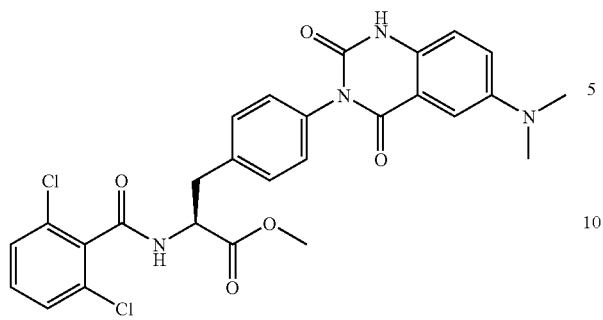

There was suspended, in 480 mL of acetonitrile, 47.1 g of 4-{2-amino-5-di-methylamino-benzoylamino}-N^α-(2,6-dichlorobenzoyl)-L-phenylalanine methyl ester synthesized in the foregoing step 1, then 15.9 g of 1,1'-carbonyl-diimidazole (CDI) was added to the suspension and then the mixture was heated at a temperature ranging from 55 to 60° C. for 2.5 hours with stirring. After the completion of the reaction, the mixture was cooled to 5° C. and the resulting crystals were filtered off to thus give 35.6 g of primary crystals. The filtrate and the wash liquid were concentrated to half, then 200 mL of water was added thereto to thus separate out crystals, the resulting slurry was filtered and the resulting crystals were dried to thus give 6.35 g of secondary crystals. The physical properties of the resulting compound were found to be in good agreement with those observed for the same compound prepared in the foregoing synthesis Example.

Example 19

Synthesis of 2-ethoxy-6-(N-formyl-N-methylamino-methyl)-3,1-benzoxazin-4-one

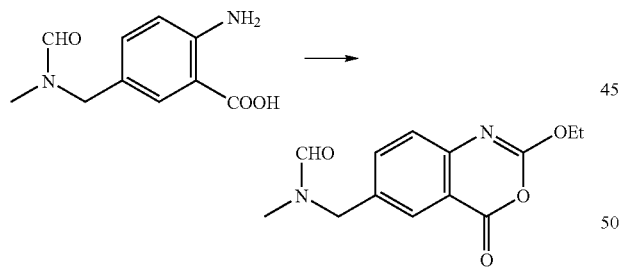

To 6.0 g of 2-amino-5-(N-formyl-N-methylamino-methyl)-benzoic acid, there was added 30 mL of pyridine and then 11.1 mL of ethyl chloroformate was dropwise added to the mixture while ice-cooling the same. After the elapse of a night, 20 mL of water was dropwise added to the mixture to separate out a solid material, the solid was then isolated through filtration under reduced pressure and washed with 20 mL of water. Then the solid thus separated was dried under reduced pressure to give 3.97 g of the intended compound as a white solid.

$^1$H-NMR (400 MHz, CDCl$_3$): δ 8.33 and 8.19 (two s, 1H), 7.98 and 7.96 (two bs, 1H), 7.65 and 7.57 (two dd, 1H, J=2.2, 8.4 Hz), 7.44 and 7.40 (two d, 1H, J=8.2 Hz), 4.59 and 4.47 (two s, 2H), 4.56-4.49 (m, 2H), 2.90 and 2.79 (two s, 3H), 1.50-1.43 (m, 3H); MS (ESI+): m/z 263 (MH$^+$) and 285.1 (M+Na).

Example 20

Synthesis of 6-dimethylamino-2-ethoxy-3,1-benzoxazin-4-one

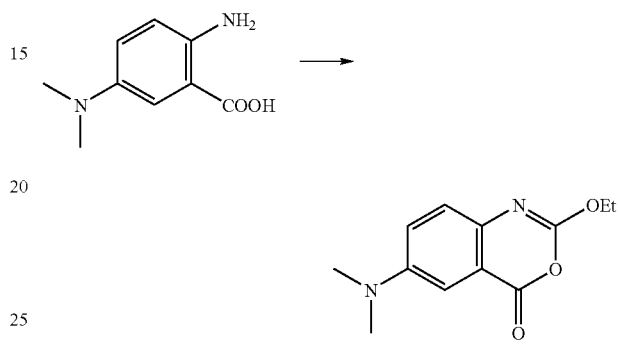

To 2.0 g of 2-amino-5-dimethylamino-benzoic acid, there was added 10 mL of acetonitrile and 4.49 mL of pyridine and the solution was heated to 20° C. To this solution, there was gradually added 3.19 mL of ethyl chloroformate and then stirred for not less than one hour. After the confirmation of the completion of the reaction, 20 mL of water was dropwise added to the solution while allowing the separation of a solid material and the mixture was cooled to 10° C. After the separation of the solid thus separated through filtration under reduced pressure, it was washed with 20 mL of water and then dried under reduced pressure at 70° C. to thus give 2.35 g of the intended product as a yellow solid.

$^1$H-NMR (400 MHz, DMSO-d$_6$): δ 7.31 (m, 2H), 7.12-7.07 (m, 1H), 4.40 (q, 2H, J=7.1 Hz), 2.96 (s, 6H), 1.35 (t, 3H, J=7.2 Hz); MS (ESI+): m/z 235.1 (M+H$^+$), 276.2 (M+MeCN) and 298.2 (M+MeCN+Na).

Example 21

Synthesis of N$^α$-(2,6-dichlorobenzoyl)-4-{1-methyl-5-(N-formyl-N-methyl-aminomethyl)-quinazoline-2,4[1H,3H]-dion-3-yl}-L-phenylalanine isopropyl ester Step 1: Synthesis of N$^α$-(2,6-dichlorobenzoyl)-4-{2-ethoxycarbonylamino-5-(N-formyl-N-methyl-aminomethyl)-benzoylamino}-L-phenylalanine isopropyl ester

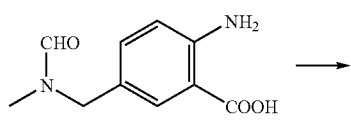

-continued

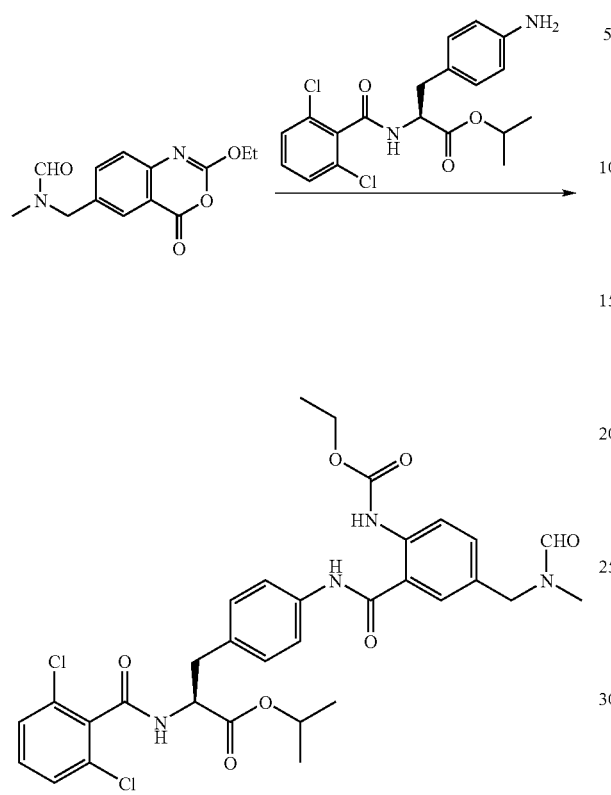

Step 2: Synthesis of N^α-(2,6-dichlorobenzoyl)-4-{1-methyl-6-(N-formyl-N-methyl-aminomethyl)-quinazoline-2,4[1H,3H]-dion-3-yl}-L-phenylalanine isopropyl ester

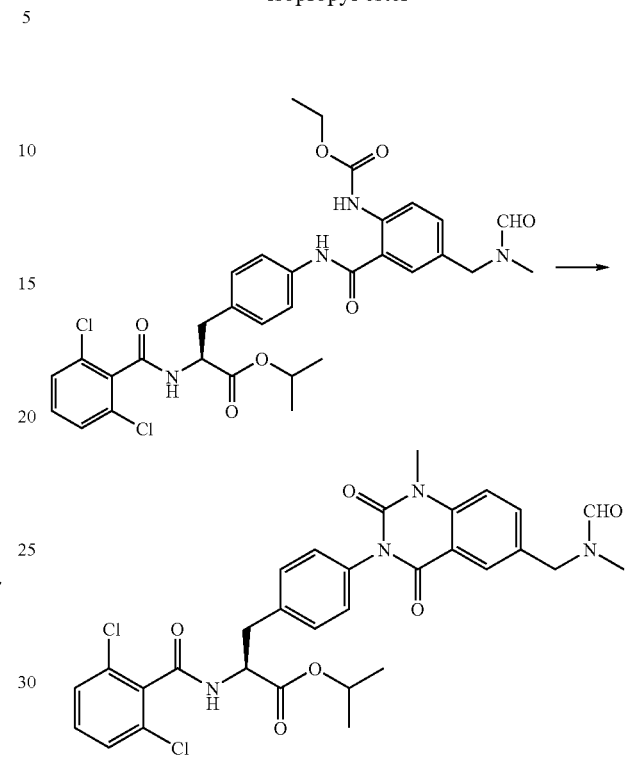

To 2.0 g of 2-amino-5-(N-formyl-N-methylamino-methyl)-benzoic acid, there were added 10 mL of acetonitrile and 3.9 mL of pyridine to form a slurry and the latter was cooled to 10° C. To this slurry, there was dropwise added 2.76 mL of ethyl chloro-formate over 5 minutes and then stirred for one hour. After the confirmation of the disappearance of the starting material by HPLC, 1.46 mL of 2-propanol was added to the reaction liquid so that the unreacted ethyl chloroformate was thus decomposed at 25° C. To this reaction liquid, there was added 3.80 g of 4-amino-N^α-(2,6-dichlorobenzoyl)-L-phenylalanine isopropyl ester and the resulting mixture was stirred overnight. Subsequently, 30 mL of 2-propanol was dropwise added to the mixture, followed by the stirring of the mixture at 10° C. for 3 hours. The solid separated was isolated through filtration under reduced pressure, washed with 10 mL of 2-propanol and then dried at 60° C. for 18 hours under reduced pressure to thus give 4.35 g of the intended product as a white crystalline solid.

$^1$H-NMR (400 MHz, DMSO-$d_6$): δ 10.42 (s, 1H), 10.11 and 10.02 (two s, 1H), 9.20 (d, 1H, J=7.9 Hz), 8.31 and 8.15 (two s, 1H), 8.06 and 8.02 (two d, 1H, J=8.4 Hz), 7.72 and 7.66 (two d, 1H, J=1.7 Hz), 7.63-7.58 (m, 2H), 7.49-7.35 (m, 4H), 7.32-7.26 (m, 2H), 4.93 (septet, 1H, J=6.4 Hz), 4.73-4.65 (m, 1H), 4.47 and 4.46 (two s, 2H), 4.11 and 4.11 (two q, 2H, J=7.2 Hz), 3.10 (dd, 1H, J=14.1, 5.9 Hz), 2.96 (dd, 1H, J=9.2, 14.0 Hz), 2.86 and 2.67 (two s, 3H), 1.22 and 1.21 (two t, 3H, J=7.2 Hz), 1.22 (d, 3H, J=6.0 Hz), 1.17 (d, 3H, J=6.4 Hz); MS (ESI+): m/z 657.1 (MH$^+$), (ESI−): m/z 655.2.

To 17.1 g of N^α-(2,6-dichlorobenzoyl)-4-{2-ethoxycarbonylamino-5-(N-formyl-N-methyl-aminomethyl)-benzoylamino}-L-phenylalanine isopropyl ester prepared in the foregoing step 1, there were added 68 mL of N,N-dimethylformamide, 6.8 mL of 2-propanol and 7.55 g of potassium carbonate, and then 5.89 mL of methyl p-toluene-sulfonate was added to the resulting mixture, followed by the stirring of the mixture at room temperature overnight. After confirming the completion of the reaction by HPLC, 6.25 mL of acetic acid was added to quench the mixture and then 84 mL of water was dropwise added thereto to separate out a solid material. The separated solid was isolated through filtration under reduced pressure, washed with 82 mL of water and then dried under reduced pressure to thus give 15.80 g of the intended compound as a white crystalline solid. The physical properties of the 4-amino-N^α-(2,6-dichlorobenzoyl)-L-phenylalanine methyl ester and 12 mL of N,N-dimethylformamide, and the resulting mixture was stirred overnight. Subsequently, 48 mL of methanol was dropwise added, the resulting mixture was stirred at 10° C. overnight and then the solid separated from the mixture was isolated through filtration under reduced pressure. The solid was then washed with 8 mL of methanol and dried at 70° C. for 5 hours under reduced pressure to thus give 5.50 g of the title compound as a pale yellow solid.

$^1$H-NMR (400 MHz, DMSO-$d_6$): δ 10.29 (s, 1H), 9.42 (bs, 1H), 9.24 (d, 1H, J=7.9 Hz), 7.73 (bs, 1H), 7.62 (d, 2H, J=8.4 Hz), 7.48-7.44 (m, 2H), 7.41 (dd, 1H, J=9.5, 6.2 Hz), 7.27 (d, 2H, J=8.4 Hz), 7.01 (d, 1H, J=2.7 Hz), 6.93 (dd, 1H, J=9.1, 2.9 Hz), 4.71 (ddd, 1H, J=9.2, 8.1, 5.7 Hz), 4.05 (q, 2H, J=7.0 Hz), 3.66 (s, 3H), 3.10 (dd, 1H, J=14.0, 5.6 Hz), 2.96 (dd, 1H, J=14.0, 9.2 Hz), 2.93 (s, 6H), 1.18 (t, 3H, J=7.2 Hz); MS (ESI+): m/z 601.2 (MH+) and 623.2 (M+Na), (ESI−): m/z 599.1 (M−H−).

Step 2: Synthesis of N$^\alpha$-(2,6-dichlorobenzoyl)-4-{6-dimethylamino-1-methyl-quinazoline-2,4[1H,3H]-dion-3-yl}-L-phenylalanine methyl ester

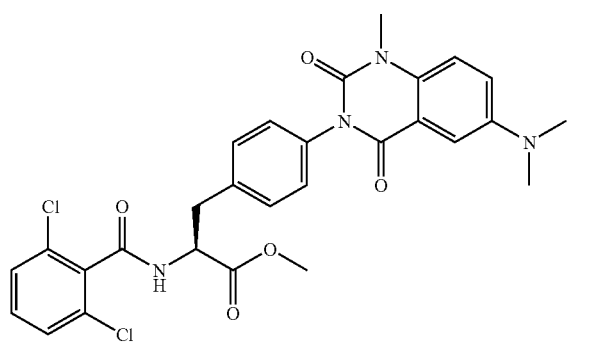

To 2.0 g of N$^\alpha$-(2,6-dichlorobenzoyl)-4-{2-ethoxycarbonylamino-5-dimethyl-amino-benzoylamino}-L-phenylalanine methyl ester prepared in the foregoing step 1, there were added 16 mL of N,N-dimethylformamide, 0.8 mL of methanol and 0.91 g of potassium carbonate, followed by the stirring of the resulting mixture at 25° C. overnight. To this reaction liquid, there was added 0.75 mL of methyl p-toluenesulfonate for subjecting the methyl ester to alkylation at a temperature ranging from 25 to 40° C. After confirming the disappearance of the starting material by HPLC, 0.75 mL of acetic acid was added to quench the reaction liquid and then 16 mL of water was dropwise added thereto to separate out a solid material. Further, 8 mL of a 1/1 N,N-dimethylformamide/water mixed liquid was added to the resulting mixture, followed by the stirring of the mixture at 25° C. Then the solid thus separated was isolated through filtration under reduced pressure and then washed with 8 mL of water. Thereafter, the isolated solid was dried at 70° C. for 4 hours under reduced pressure to thus give 1.77 g of the intended compound as a pale yellow solid.

$^1$H-NMR (400 MHz, DMSO-d$_6$): δ 9.28 (d, 1H, J=8.1 Hz), 7.48-7.36 (m, 6H), 7.31 (dd, 1H, J=3.0, 9.0 Hz), 7.24 (d, 1H, J=3.0 Hz), 7.20-7.15 (m, 2H), 4.18 (ddd, 1H, J=10.2, 8.1, 4.8 Hz), 3.69 (s, 3H), 3.49 (s, 3H), 3.22 (dd, 1H, J=14.1, 4.8 Hz), 3.02 (dd, 1H, J=14.2, 10.5 Hz), 2.94 (s, 6H); MS (ESI+): m/z 569.2 (MH+) and 591.1 (M+Na), (ESI−): m/z 567.2 (M−H−). resulting compound were found to be in good agreement with those observed for the same compound prepared in the foregoing synthetic Example.

In this connection, this compound could be subjected to de-formylation according to the method detailed in the step 3 of Example 5 to thus convert it into N$^\alpha$-(2,6-di-chlorobenzoyl)-4-{1-methyl-6-(N-methyl-aminomethyl)-quinazoline-2,4[1H,3H]-dion-3-yl}-L-phenylalanine isopropyl ester.hydrochloride.

Example 22

Synthesis of N$^\alpha$-(2,6-dichlorobenzoyl)-4-{1-methyl-6-dimethylamino-quinazoline-2,4[1H,3H]-dion-3-yl}-L-phenylalanine isopropyl ester Step 1: Synthesis of N$^\alpha$-(2,6-dichlorobenzoyl)-4-{2-ethoxycarbonylamino-5-dimethyl-amino-benzoylamino}-L-phenylalanine methyl ester

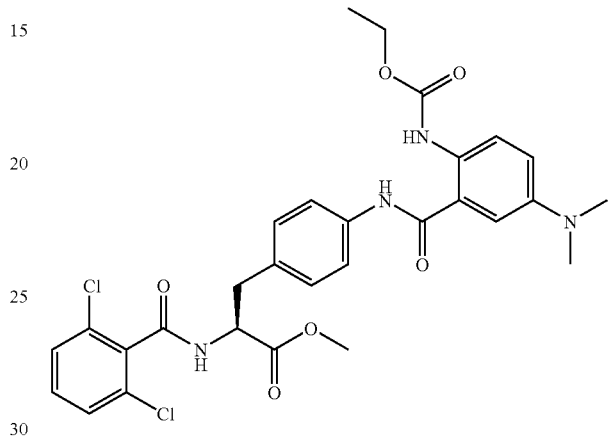

To 1.96 g of 2-amino-5-dimethylamino-benzoic acid, there were added 12 mL of acetonitrile and 5.29 mL of pyridine to form a suspension and then the resulting suspension was cooled to 4° C. To this suspension there was dropwise added 4.17 mL of ethyl chloroformate over 5 minutes and then the mixture was stirred at 25° C. for one hour. After confirming the disappearance of the starting material by HPLC, 0.7 mL of ethanol was added to the mixture to thus decompose the excess ethyl chloroformate and the mixture was further stirred for additional one hour. To this reaction liquid there were added 4.0 g of

What is claimed is:

1. A method for preparing a compound represented by the following formula (1) or a pharmaceutically acceptable salt thereof, comprising:

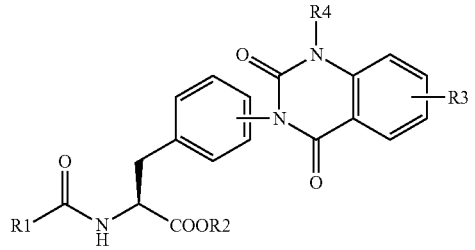

wherein R1 represents either a phenyl group which may have a substituent or a pyridyl group which may have a substituent; R2 represents an alkyl group which may have a substituent; R3 represents an alkyl group substituted with a di-alkylamino group, an alkyl group substituted with a mono-alkylamino group or an alkyl group substituted with an amino group; and R4 represents a hydrogen atom, an alkyl group or a benzyl group which may have a substituent;

(a) reacting a compound represented by the following formula (2) or a chemically acceptable salt thereof:

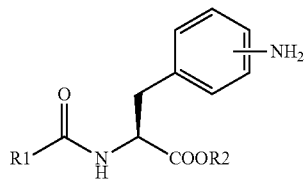

(2)

wherein R1 and R2 are the same as those defined above, with a carbonyl group-introducing reagent and a compound represented by the following formula (3) or a chemically acceptable salt thereof:

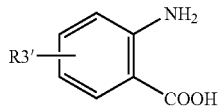

(3)

wherein R3' represents an alkyl group substituted with a dialkylamino group, an alkyl group substituted with a mono-alkylamino group which may have a protective group or an alkyl group substituted with an amino group which may have a protective group, to thus form a compound represented by the following formula (4) or a chemically acceptable salt thereof:

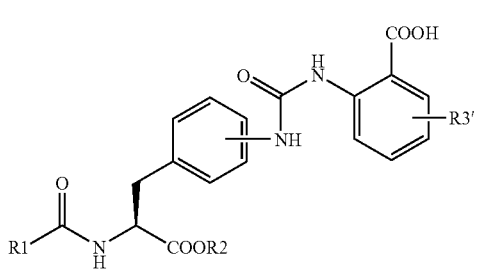

(4)

wherein R1, R2 and R3' are the same as those defined above;

(b) converting the compound of Formula (4) into a quinazoline-dione compound represented by the following formula (5) or a pharmaceutically acceptable salt thereof, in the presence of a carboxyl group-activating agent:

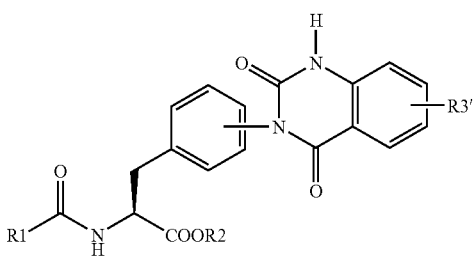

(5)

wherein R1 to R3' are the same as those defined above; and (c) if desired, substituting an N-alkyl group for the hydrogen atom bonded to the nitrogen atom present in the quinazoline-dione ring of the compound of Formula (5) using an N-alkylation agent and then deprotecting the resulting product, when the substituent R3' is protected.

2. The method as set forth in claim 1, wherein R3 appearing in Formula (1) is a methylamino-methyl group, an ethylamino-methyl group or a dimethylamino-methyl group; R3' appearing in Formulas (3) to (5) is a methyl group substituted with a methylamino group having a protective group, a methyl group substituted with an ethylamino group having a protective group, a dimethylamino-methyl group or a diethylamino-methyl group.

3. The method as set forth in claim 1, wherein, in Formulas (1) to (5), R1 is a 2,6-dichlorophenyl group, a 2-chloro-6-methylphenyl group, a 2-chloro-6-fluorophenyl group, a 2,6-difluorophenyl group or a 2-fluoro-6-methylphenyl group; R4 represents either a methyl group or an ethyl group; and the quinazoline-dione substituent present on the benzene ring of the phenylalanine moiety is present at p-position of the benzene ring.

4. The method as set forth in claim 1, wherein the carbonyl group-introducing reagent is 1,1'-carbonyl-diimidazole, 1,1'-carbonyl-ditriazole, or a chloroformate ester.

5. The method as set forth in claim 1, wherein the carboxyl group-activating agent is 1,1'-carbonyl-diimidazole, a chloroformate ester, an alkylsulfonic acid chloride, N,N'-dicyclohexyl-carbodiimide (DCC) or 1-ethyl-3-(3-dimethylaminopropyl)-carbodiimide.

6. The method as set forth in claim 1, wherein the N-alkylation agent is methyl p-toluene-sulfonate, methyl methanesulfonate, methyl iodide, methyl bromide, or methyl chloride.

7. The method as set forth in claim 1, wherein the compound of Formula (2) is first reacted with the carbonyl group-introducing reagent and then the resulting product is reacted with the compound of Formula (3).

8. The method as set forth in claim 1, wherein the compound of formula (4) is not isolated.

9. The method as set forth in claim 1, wherein a compound of Formula (2) in which R1 of Formula (2) is a 2,6-dichlorophenyl group and R2 is an isopropyl group, is reacted with 1,1'-carbonyl-diimidazole as a carbonyl group-introducing reagent and a compound of Formula (3) in which R3' is an N-formyl-N-methyl-aminomethyl group to thus form 2-(3-{4-[2(S)-2-(2,6-dichlorobenzoylamino)-2-isopropoxycarbonylethyl)-phenyl}ureido)-5-(N-formyl-N-methyl-aminomethyl)-benzoic acid of Formula (4) in which R1 is a 2,6-dichlorophenyl group, R2 is an isopropyl group, and R3' is an N-formyl-N-methyl-aminomethyl group; then the resulting compound is reacted with 1,1'-carbonyl-diimidazole as a carboxyl group-activating agent to thus convert the former into $N^\alpha$-(2,6-dichlorobenzoyl)-4-{6-(N-formyl-N-methyl-aminomethyl)-quinazoline-2,4[1H,3H]-dion-3-yl}-L-phenylalanine isopropyl ester of Formula (5) in which R1 is a 2,6-dichlorophenyl group, R2 is an isopropyl group and R3' is an N-formyl-N-methyl-aminomethyl group; subsequently N-alkylation of the resulting product is carried out using methyl p-toluene-sulfonate to thus convert the product into N$^\alpha$-(2,6-dichlorobenzoyl)-4-{1-methyl-6-(N-formyl-N-methylamino-methyl)-quinazoline-2,4[1H,3H]-dion-3-yl}-L-phenylalanine isopropyl ester; and finally the N-alkylated product is treated with hydrogen chloride to thus deprotect the formyl group thereof to thus give N$^\alpha$-(2,6-dichlorobenzoyl)-4-[1-methyl-6-(N-methylamino-methyl)-quinazoline-2,4[1H,3H]-dion-3-yl}-L-phenylalanine isopropyl ester of Formula (1) or a hydrochloride thereof, in which R1 is a 2,6-dichlorophenyl group, R2 is an isopropyl group, R3' is an N-methyl-aminomethyl group and R4 is a methyl group.

10. The method as set forth in claim 1, wherein R1 is a phenyl group which may have a substituent or a pyridyl group which may have a substituent, wherein the substituent is selected from the group consisting of halogen atoms, alkyl groups, halogenoalkyl groups, alkoxy groups, halogenoalkoxy groups, alkylthio groups, nitro group, alkyl-sulfonylamino groups, and a tetrazolyl group.

11. The method as set forth in claim 1, wherein R1 is an unsubstituted phenyl group.

12. The method as set forth in claim 1, wherein R1 is an unsubstituted pyridyl group.

13. The method as set forth in claim 10, wherein R1 is an substituted phenyl group.

14. The method as set forth in claim 10, wherein R1 is an substituted pyridyl group.

15. The method as set forth in claim 1, wherein R2 represents an alkyl group which may have a substituent selected from the group consisting of substituted or unsubstituted lower alkyl-carbonyloxy groups, substituted or unsubstituted lower alkoxy-carbonyloxy groups, substituted or unsubstituted amino groups, lower alkoxy groups, halogen atoms, substituted or unsubstituted aryl groups, substituted or unsubstituted heteroaryl groups and substituted or unsubstituted carbamoyl groups.

16. The method as set forth in claim 1, wherein R2 represents an unsubstitued alkyl group.

17. The method as set forth in claim 1, wherein R2 represents an substitued alkyl group.

18. The method as set forth in claim 1, wherein R4 represents a hydrogen atom, an alkyl group or a benzyl group which may have a substituent selected from the group consisting of alkyl groups, alkoxy groups and halogen atoms.

19. The method as set forth in claim 18, wherein R4 represents a hydrogen atom.

20. The method as set forth in claim 18, wherein R4 represents an alkyl group.

21. The method as set forth in claim 18, wherein R4 represents a benzyl group which may have a substituent selected from the group consisting of alkyl groups, alkoxy groups and halogen atoms.

* * * * *